United States Patent [19]
Weininger et al.

[11] Patent Number: 5,871,902
[45] Date of Patent: Feb. 16, 1999

[54] SEQUENCE-SPECIFIC DETECTION OF NUCLEIC ACID HYBRIDS USING A DNA-BINDING MOLECULE OR ASSEMBLY CAPABLE OF DISCRIMINATING PERFECT HYBRIDS FROM NON-PERFECT HYBRIDS

[75] Inventors: Susan Weininger; Arthur M. Weininger, both of Seattle, Wash.

[73] Assignee: The Gene Pool, Inc., Seattle, Wash.

[21] Appl. No.: 353,476

[22] Filed: Dec. 9, 1994

[51] Int. Cl.[6] .............................. C12Q 1/70; C12Q 1/68; C07H 21/04
[52] U.S. Cl. .................... 435/5; 435/6; 436/94; 536/24.3
[58] Field of Search ................. 536/24.3, 23.1; 435/5, 6, 810; 436/94

[56] References Cited

U.S. PATENT DOCUMENTS

| | | | |
|---|---|---|---|
| 4,556,643 | 12/1985 | Paau et al. | 436/501 |
| 4,623,627 | 11/1986 | Huang et al. | 435/240 |
| 4,683,195 | 7/1987 | Mullis et al. | 435/6 |
| 4,724,202 | 2/1988 | Dattagupta et al. | 435/6 |
| 4,751,177 | 6/1988 | Stabinsky | 435/6 |
| 4,775,619 | 10/1988 | Urdea | 435/6 |
| 4,777,129 | 10/1988 | Dattagupta et al. | 435/6 |
| 4,794,075 | 12/1988 | Ford et al. | 435/6 |
| 4,868,105 | 9/1989 | Urdea et al. | 435/6 |
| 4,882,269 | 11/1989 | Schneider et al. | 435/6 |
| 4,948,882 | 8/1990 | Ruth | 536/27 |
| 4,960,691 | 10/1990 | Gordon et al. | 435/6 |

(List continued on next page.)

FOREIGN PATENT DOCUMENTS

| | | |
|---|---|---|
| 0146039 | 6/1985 | European Pat. Off. . |
| 0147665 | 7/1985 | European Pat. Off. . |
| 0357336 | 3/1990 | European Pat. Off. . |
| 0450594 | 10/1991 | European Pat. Off. . |
| 0453301 | 10/1991 | European Pat. Off. . |
| 8703622 | 6/1987 | WIPO . |
| 8806601 | 9/1988 | WIPO . |
| 9106679 | 5/1991 | WIPO . |
| 9220698 | 11/1992 | WIPO . |
| 9300446 | 1/1993 | WIPO . |
| 9315226 | 8/1993 | WIPO . |
| 9320233 | 10/1993 | WIPO . |
| 9417087 | 8/1994 | WIPO . |

OTHER PUBLICATIONS

Matthews et al, *Analyt. Biochem.* 169, 1–25 (1988).
Bülow et al, *Nucleic Acids Res.* 14(9), 3973 (1986).
Keller, G.H., M.M. Manak (1989) DNA Probes, Stockton Press, pp. v–xiii, 192–210, 215–230.
Ptashne, M., A.D. Johnson, C.O. Pabo (1982) "A Genetic Switch in a Bacterial Virus" *Scientific American* 247(5):128–140.
Ghosh, S. et al. (1990) "Cloning of the p50 DNA Binding Subunit of NF–KB: Homology to rel and dorsal" *Cell* 62:1019–1029.

(List continued on next page.)

*Primary Examiner*—Kenneth R. Horlick
*Attorney, Agent, or Firm*—Saliwanchik, Lloyd & Saliwanchik

[57] ABSTRACT

This invention is a novel method for detecting and localizing specific nucleic acid sequences in a sample with a high degree of sensitivity and specificity. The method and novel compositions used in the method involve the use of Probe Nucleic Acids, the production of nucleic acid binding regions and the use of nucleic acid Target Binding Assemblies to detect and localize specific Target Nucleic Acids. The detection and localization of the Target Nucleic Acid is accomplished even in the presence of nucleic acids which have similar sequences. The method provides for a high degree of amplification of the signal produced by each specific binding event. In particular, methods and compositions are presented for the detection of HIV and HPV DNA in samples. These methods and compositions find use in diagnosis of disease, genetic monitoring, forensics, and analysis of nucleic acid mixtures. Some of the novel compositions used in the detection method are useful in preventing or treating pathogenic conditions.

40 Claims, 27 Drawing Sheets

U.S. PATENT DOCUMENTS

| | | |
|---|---|---|
| 5,096,815 | 3/1992 | Ladner et al. . |
| 5,118,605 | 6/1992 | Urdea .......................................... 435/6 |
| 5,122,600 | 6/1992 | Kawaguchi et al. ...................... 536/27 |
| 5,124,246 | 6/1992 | Urdea et al. ................................. 435/6 |
| 5,198,346 | 3/1993 | Ladner et al. . |
| 5,200,314 | 4/1993 | Urdea ......................................... 435/6 |
| 5,215,882 | 6/1993 | Bahl et al. ................................... 435/6 |
| 5,215,899 | 6/1993 | Dattagupta .................................. 435/6 |
| 5,290,677 | 3/1994 | Robertson et al. .......................... 435/5 |
| 5,306,614 | 4/1994 | Alizon et al. ............................... 435/5 |
| 5,306,619 | 4/1994 | Edwards et al. ............................ 435/6 |
| 5,310,650 | 5/1994 | McMahon et al. .......................... 435/6 |
| 5,314,809 | 5/1994 | Erlich et al. ........................... 435/91.2 |
| 5,324,829 | 6/1994 | Bahl et al. . |
| 5,459,039 | 10/1995 | Modrich et al. ............................. 435/6 |
| 5,556,750 | 9/1996 | Modrich et al. ............................. 435/6 |
| 5,593,834 | 1/1997 | Lane et al. .................................. 435/6 |
| 5,679,522 | 10/1997 | Modrich et al. ............................. 435/6 |

OTHER PUBLICATIONS

Baldwin, A.S. Jr. et al. (1991) "Induction of NF–κB DNA–Binding Activity during the G –to–G₁ Transition in Mouse Fibroblasts" Molecular and Cellular Biology 11(10):4943–4951.

Rosin, H. (1994) "Bad Blood" in The New Republic, Jun. 27, p. 12.

Taylor, I. (1994). "Johnson & Johnson leads race for over–the–counter HIV test" Newark Star Ledger, Jul. 24.

Haugen, T.H. et al. (1987) "Trans–activation of an upstream early gene promoter of bovine papilloma virus–1 by a product of the viral E2 gene" The EMBO Journal 6(1):145–152.

Spalholz, B:A, et al. (1987) "Bovine Papillomavirus Transcriptional Regulation: Localization of the E2–Responsive Elements of the Long Control Region" Journal of Virology 61(7):2128–2137.

Spalholz, B.A. Y.–C., Yang, P.M. Howley (1985) "Transactivation of a Bovine Papilloma Virus Transcriptional Regulatory Element by the E2 Gene Product" Cell 42:183–191.

Jones, K.A., P.A. Luciw, N. Duchange (1988) "Structural arrangements of transcription control domains within the 5'–untranslated leader regions of the HIV–1 and HIV–2 promoters" Genes & Development 1101–1114.

Wu, F.K., J.A. Garcia, D. Harrish, R.B. Gaynor (1988) "Purification of the human immunodeficiency virus type 1 enhancer and TAR binding proteins EBP–1 and UBP–1" The EMBO Journal 7(7):2117–2129.

Sodroski, J. et al. (1985) "Location of the Trans–Activating Region on the Genome of Human T–Cell Lymphotropic Virus Type III" Science 229:74–77.

Arya, S.K. et al. (1985) "Trans–Activator Gene of Human T–Lymphotropic Virus Type III (HTLV–III)" Science 229:69–72.

Berg, J.M. (1986) "Potential Metal–Binding Domains in Nucleic Acid Binding Proteins" Science 232:485–487.

Lambert, P.F., B.A. Spalholz, P.M. Howley (1987) "A Transcriptional Repressor Encoded by BPV–1 Shares a Common Caboxy–Terminal Domain with the E2 Transactivator" Cell 50:69–78.

Lenardo, M.J. et al. (1989) "The involvement of the NF–κB in β–Interferon Gene Regulation Reveals Its Role as Widely Inducible Mediator of Signal Transduction" Cell 57:287–294.

Hiscott, J. et al. (1989) "Induction of Human Interferon Gene Expression is Associated with Nuclear Factor that Interacts with the NF–κB Site of the Human Immunodeficiency Virus Enhancer" Journal of Virology 63(6):2557–2566.

Perkins, N.D. et al. (1993) "A cooperative interaction between NF–κB and Sp1 is eequired for HIV–1 enhancer activation" The EMBO Journal 12(9):3551–3558.

Franzoso, G. et al. (1993) "The oncoprotein Bcl–3 can facilitate NF–κB–mediated transactivation by removing inhibiting p50 homodimers from select κB sites" The EMBO Journal 12(10):3893–3901.

Kim, Y. et al. (1993) "Crystal structure of a yeast TBP/ TATA–box complex" Nature 365:512–521.

Kadonaga, J.T. et al. (1987) "Isolation of cDNA Encoding Transcription Factor Sp1 and Functional Analysis of the DNA Binding Domain" Cell 51:1079–1090.

Courey, A.J., R. Tijan (1988) "Analysis of Sp1 In Vivo Reveals Multiple Transcriptional Domains, Including a Novel Glutamine–Rich Activation Motif" Cell 55:887–898.

Urban, M.B., R. Schreck, P.A. Baeuerle (1991) "NF–κB contacts DNA by a heterodimer of the p50 and p65 subunit" The EMBO Journal 10(7):1817–1825.

Kunsch, C., S.M. Ruben, C.A. Rosen (1992) "Selection of Optimal κB/Rel DNA–Binding Motifs: Interaction of Both Subunits of NF–κB with DNA is Required for Transcriptional Activation" Mollecular and Cellular Biology 12(10):4412–4421.

Ikeda, T., K. Honjo, Y. Hirota, T. Onodera (1993) "Isolation of the chicken NF–κB p65 subunit–encoding cDNA and characterization of its products" Gene133:237–242.

Matthews, J.R. et al. (1993) "Rate of cysteine$_{62}$ in DNA recognition by the P50 subunit of NF–κB" Nucleic Acids Research 21(8):1727–1734.

Beg, A.A. et al. (1992) IκB interacts with the nuclear localization sequences of the subunits of NF–κB: a mechanism for cytoplasmic retention Genes & Development 6:1899–1913.

Jones, K.A., J.T. Kadonaga, P.A. Luciw, R. Tijan (1986) "Activation of the AIDS Retrovirus Promoter by the Cellular Transcription Factor, Sp1" Science 232:755–759.

Mukaida, N., Y. Mahe, K. Matsushima (1990) "Cooperative Interaction of Nuclear Factor–κB–and cis–Regulatory Enhancer Binding Protein–like Factor Binding Elements in Activating the Interleukin–8 Gene by Pro–inflammatory Cytokines" The Journal of Biological Chemistry 265(34):21128–21133.

McBride, A.A., R. Schlegel, P.M. Howley (1988) "The carboxy–terminal domain shared by the bovine papillomavirus E2 transactivator and repressor proteins contains a specific DNA binding activity" The EMBO Journal 7(2):533–539.

Henkel, T. et al. (1992) "Intramolecular Masking of the Nuclear Location Signal and Dimerization Domain in the Precursor for the p50 NF–κB Subunit" Cell 68:1121–1133.

Matsusaka, T. et al. (1993) "Transcription factors NF–IL6 and NF–κB synergistically activate transcription of the inflammatory cytokines, interleukin 6 and interleukin 8" Proc. Natl. Acad. Sci. USA 90:10193–10197.

Margolis, D.M., A.B. Rabson, S.E. Straus, J.M. Ostrove (1992) Transactivation of the HIV–1 LTR by HSV–1 Immediate–Early Gens' Virology 186:788–791.

Grimm, S., P.A. Baeuerle (1993) "The inducible transcription factor NF–κB: structure–function relationship of its protein subunits" Biochem. J.

American Society of Clinical Pathologists (1989) "The Abbott IMx" Laboratory Medicine 20(1):47–49.

Harrison, S.C., A.K. Aggarwal (1990) "DNA Recognition by Proteins with the Helix–Turn–Helix Motif" Annu. Rev. Biochem. 59:933–969.

Anderson, W.F., D.H. Ohlendorf, Y. Takeda, B.W. Matthews (1981) "Structure of the cro repressor fram bacteriophage λ and its interaction with DNA" Nature 290:754–758.

Baker, C.C., P.M. Howley (1987) "Differential promoter utilization by the bovine papillomavirus in transformed cells and productively infected wart tissues" The EMBO Journal 6(4):1027–1035.

Baker, C.C. et al. (1987) "Structural and Transcriptional Analysis of Human Papillomavirus Type 16 Sequences in Cervical Carcinoma Cell Lines" Journal of Virology 61(4):962–971.

Phelps, W.C., P.M. Howley (1987) "Transcriptional trans–Activation by the Human Papillomavirus Type 16 E2 Gene Product" Journal of Virology 61(5):1630–1638.

Schwarz, E. et al. (1985) "Structure and transcription of human papillomavirus sequences in cervical carcinoma cells" Nature 314:111–114.

Yee, C. et al. (1985) "Presence and Expression of Human Papillomavirus Sequences in Human Cervical Carcinoma Cell Lines" Am. J. Pathol. 119:361–366.

McBride, A.A., H. Romanczuk, P.M. Howley (1991) "The Papillomavirus E2 Regulatory Proteins" The Journal of Biological Chemistry 266(28):18411–18414.

Kerr, L.D. et al. (1993) "Association between protp–oncoprotein Rel and TATA–binding protein mediates transcriptional activation by NF–κB" Nature 365:412–419.

Kim, J.L., D.B. Nikolov, S.K. Burley (1993) "Co–crystal structure of TBP recognizing the minor groove of a TATA element" Nature 365:520–527.

Kim, Y., J.H. Geiger, S. Hahn, P.B. Sigler (1993) "Crystal structure of a yeast TBP/TATA–box complex" Nature 365:512–517.

Northrop, J.P. et al. (1994) "NF–AT components define a family of transcription factors targeted in T–cell activation" Nature 369:497–502.

Kadonaga, J.T., K.R. Carner, F.R. Masiarz, R. Tjian (1987) "Isolation of cDNA Encoding Transcription Factor Sp1 and Functional Analysis of the DNA Binding Domain" Cell 51:1079–1090.

Perkins, N.D. et al. (1993) "A cooperative interaction between NF–κB and Sp1 is required for HIV–1 enhancer activation" The EMBO Journal 12(9):3551–3558.

Gill, G., E. Pascal, Z.H. Tseng, R. Tjian (1994) "A glutamine–rich hydrophobic patch in transcription factor Sp1 contacts the dTAF$_{II}$110 component of the Drosophila TFIID complex and mediates transcriptional activation" Proc. Natl. Acad. Sci. USA 91:192–196.

Ptashne, M. (1989) "How Gene Activators Work" Scientific American, Jan. 40–47.

Hochschild, A., M. Ptashne (1986) "Cooperative Binding of a λ Repressors to Sites Separated by Integral Turns of the DNA Helix" Cell 44:681–687.

Antoni, B.A. et al. (1994) "NF–κ B–Dependent and –Independent pathways of HIV Activation in a Chronically Infected T Cell Line" Virology 202:684–694.

Musso, T. et al. (1994) "LPS–inducible nuclear factor in human monocytes that binds the negative regulatory element of the HIV LTR" Journal of Leukocyte Biology 56:21–26.

Koken, S.E.C. et al. (1992) "Natural Variants of the HIV–1 Long Terminal Repeat: Analysis of Promoters with Duplicated DNA Regulatory Motifs" Virology 191:968–972.

Harrich, D. J. Garcia, R. Mitsuyasu, R. Gaynor (1990) "TAR independent activation of the human immunodeficiency virus in phorbol ester stimulated T lymphocytes" The EMB Journal 9:4417–4423.

Tong–Starksen, S.E., P.A. Luciw, B.M. Perlin (1987) "Human immunodeficiency virus long terminal repeat responds to T–cell activation signals" Proc. Natl. Acad. Sci. USA 84:6845–6849.

Danheiser, S.L. (1994) "bDNA Assay Allows Monitoring of Virus Loan in HIV and HCV" Genetic Engineering News 14(18):1,27.

Hoffmann, A. et al. (1990) "Highly conserved core domain and unique N terminus with presumptive regulatory motifs in a human TATA factor (TFIID)" Nature 346:387–396.

Peterson, M.G., N. Tanese, B.F. Pugh, R. Tjian (1990) "Functional Domains and Upstream Activation Properties of Cloned Human TATA Binding Protein" Science 1624–1630.

Zabel, U. et al. (1993) "Nuclear uptake control of NF–κB by MAD–3, an IκB protein present in the nucleus" The EMBO Journal 12(1):201–211.

Nikolov, D.B. et al. (1992) "Crystal structure of TFIID TATA–box binding protein" Nature 360:40–46.

Hegde, R.S., S.R. Grossman, L.A. Laimins, P.B. Sigler (1992) "Crystal structure at 1.7A of the bovine papillomavirus–1 E2 DNA–binding domain bound to its DNA target" Nature 359:505–512.

SEQ. ID: 37:
```
         1234567890123456789012345678901234567890
CTACAAGGACTTTCCGCTGGGACTTTCCAGGAGGCGTGGCCTGGGCGGACTGGGGAGTGGCGTCCC
++++++++++++++++++++++++++++++++                       =============
    NF-kB              NF-kB        SP1           SP1       SP1
```

HIV Test Kit PNA1 (+++ from above), SEQ.ID:38:

*CTACAAGGACTTTCCGCTGGGGACTTTCCAGGAGG*

HIV Test Kit PNA2 (=== from above), SEQ. ID:39:

CGGGACTGGGGAGTGGCGTCCC###

The sticky end sequence in PNA2 is complimentary to one of the ends of the operator DNA formed from:

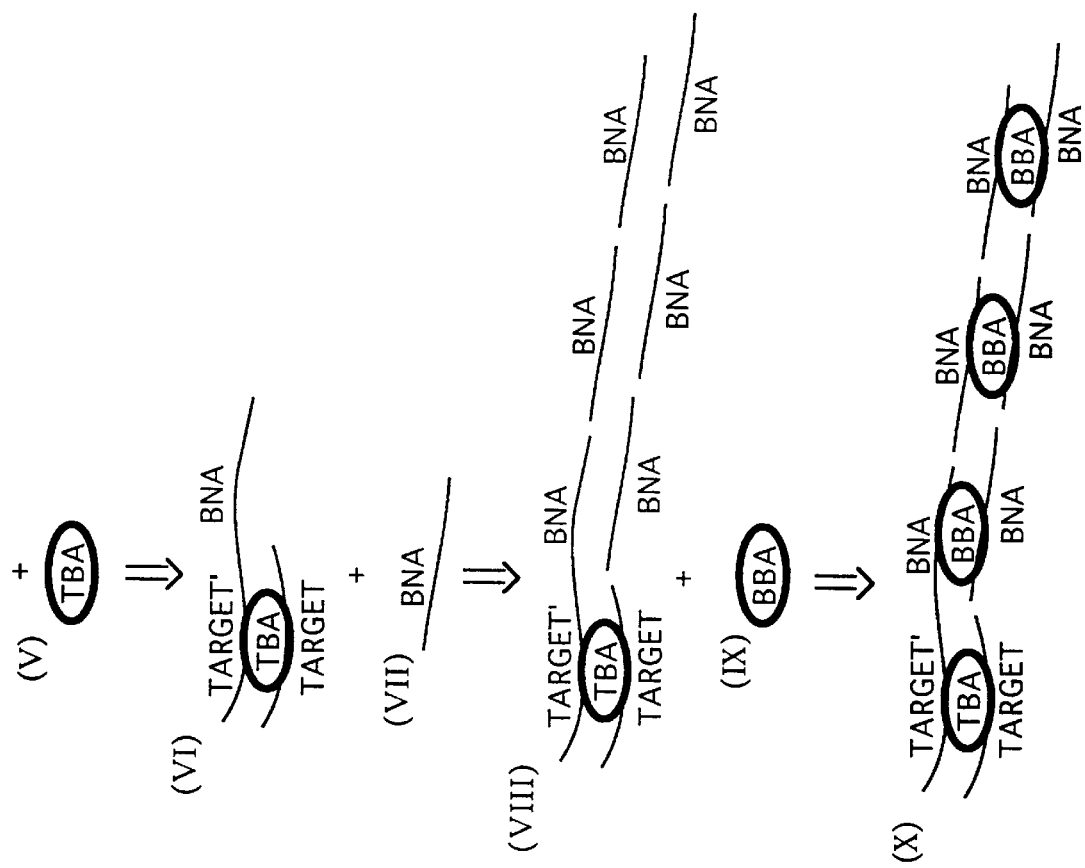

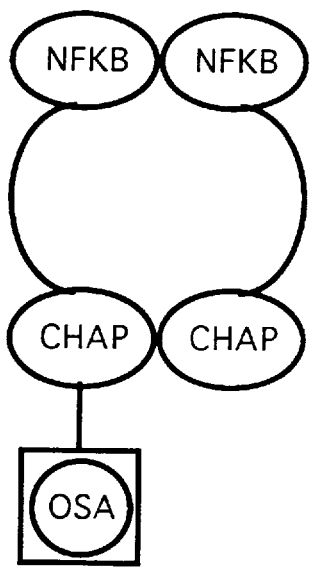
HIV-DETECT I
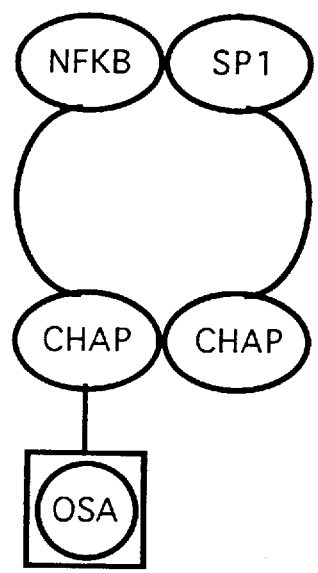
HIV-DETECT II
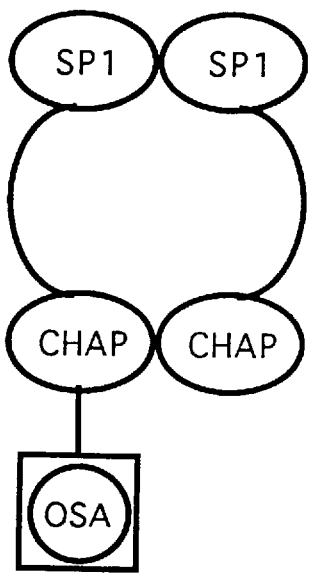
HIV-DETECT III
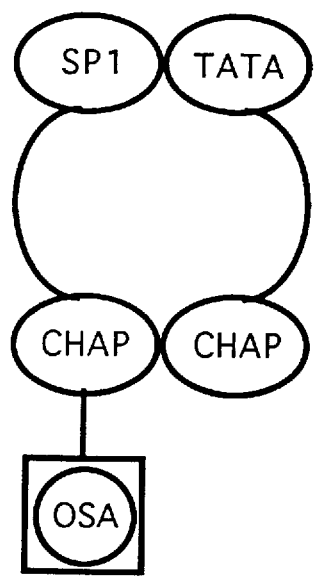
HIV-DETECT IV
FIG. 10

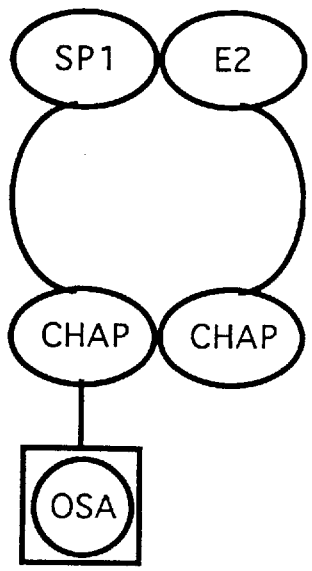
HPV-DETECT I
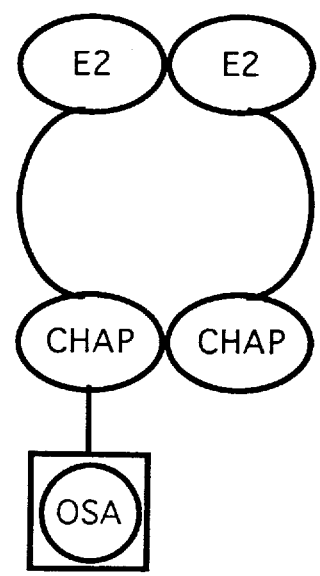
HPV-DETECT II
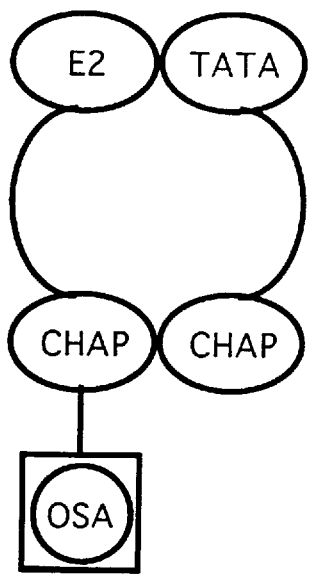
HPV-DETECT III
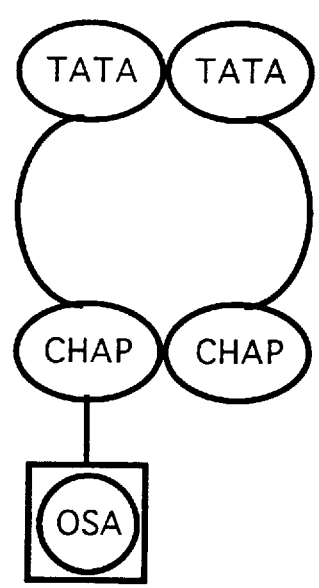
HPV-DETECT IV
FIG. 11

SEQUENCE-SPECIFIC DETECTION OF NUCLEIC ACID HYBRIDS USING A DNA-BINDING MOLECULE OR ASSEMBLY CAPABLE OF DISCRIMINATING PERFECT HYBRIDS FROM NON-PERFECT HYBRIDS

BACKGROUND OF THE INVENTION

1. Field of the Invention

This invention provides a method and compositions for use in binding, detecting, and amplifying the detection of specific Target Nucleic Acid sequences in a sample with fidelity and accuracy, even in the presence of closely related but different nucleic acids. The binding involves the chaperoning and assembly of specific molecules into Target Binding Assemblies which specifically bind Target Binding Regions formed by the hybridization of Probe Nucleic Acids and Target Nucleic Acid sequences. The amplifying involves the chaperoning and assembly of specific molecules into Booster Binding Assemblies which specifically bind Booster Binding Regions formed by the hybridization of Booster Nucleic Acids with Probe Nucleic Acids, Target Nucleic Acids, or other Booster Nucleic Acids. A method, and compositions, involving Hairpin Nucleic Acids is also provided to enable control of the size of specifically or non-specifically elongated Booster Nucleic Acids and Booster Binding Assemblies used in the amplification. The detecting involves providing one or more detectable labels, including radioactive, light- or fluorescent-emitting, enzymatic, or other detectable or signal-generating molecules, in association with the Probe Nucleic Acid, the Target Binding Assembly, the Booster Nucleic Acid, the Booster Binding Assembly, or the Hairpin Nucleic Acid. Therapeutic and prophylactic uses of the Target Binding Assemblies and compositions for such use are also provided.

2. Background and Description of Related Art

There are an increasing number of cases in which it is important to be able to detect nucleic acids containing a specific sequence, hereinafter named Target Nucleic Acids (TNAs), in a sample. It is desirable to be able to detect the TNAs with the smallest number of processing steps, with the simplest components and to the exclusion of other similar but different nucleic acids, hereinafter named Cousin Nucleic Acids (CNAs). It is desirable to be able to detect specific TNAs to the exclusion of any and all CNAs in the detection sample without the necessity of amplification or other post-detection processing.

There are numerous methods which use immobilized or tagged nucleic acids as probes for TNAs. However, using known methods, it is difficult to discriminate between a TNA bound to the Probe Nucleic Acid (PNA) as opposed to a CNA bound to the PNA. For example, one or more base mismatches between the PNA and a CNA can still result in a CNA-PNA hybridization which is almost indistinguishable from a TNA-PNA hybridization. Thus, hybridization alone is not an optimal indicator that a PNA has hybridized to its unique and complementary TNA.

There are many situations in which a PNA would be used to try to determine whether a TNA was present in a sample which may contain CNAs. Hybridization of the PNA to any CNA in this situation would limit the diagnostic value that the PNA might have for the detection of a TNA, absent additional verification. Furthermore, it is desirable to be able to detect and localize TNAs with low copy numbers in samples which may contain many copies of CNAs, without the necessity of creating additional copies of the TNA. It would also be desirable to be able to confirm the presence of CNAs, independent of the TNAs, without the necessity of separating the CNAs and TNAs in the sample.

Furthermore, it would be desirable to be able to amplify the signal of even a low frequency hybridization of a particular TNA-PNA. For this purpose, a method of polymerizing multiple copies of a label, hereinafter referred to as a Booster Nucleic Acid (BNA) onto the TNA-PNA would be desirable.

The instant invention provides methods and compositions for achieving the foregoing desired objectives. As revealed by the following review, the instant compositions and methods have not been reported or suggested in the art. A general and comprehensive review of the state of art of nucleic acid detection is provided in Keller, H., M. M. Manak (1989) *DNA Probes,* Stockton Press.

A method has been reported for detecting base pair mismatches by chemical means in order to determine whether a PNA has hybridized to a CNA rather than to a TNA. In U.S. Pat. No. 4,794,075 to Ford et al., a method for distinguishing fragments of DNA which contain single base mismatches from their perfectly paired homologs is discussed. Single stranded regions within a duplex fragment are modified with carbodiimide, which reacts with unpaired guanine (G) and thymine (T) residues in DNA. Linear duplex DNA molecules do not react, while DNA molecules with single base mismatches react quantitatively. Following reaction with carbodiimide, the DNA molecules are fractionated on high percentage polyacrylamide gels such that modified and unmodified fragments can be distinguished. Ford et al. applied this technique in order to locate and purify DNA sequence differences responsible for phenotype variation and inherited disease. Although this method is useful for following variations in genetic material, it has a large number of steps, it requires costly components, and it does not offer a direct means of determining whether a PNA has hybridized to the TNA exclusive of CNAs in the sample.

There have been some attempts to assure that at least a portion of the hybridization between the PNA and another nucleic acid is complementary. One method involves the monitoring of transcription products which are produced if the PNA hybridizes to a nucleic acid sufficiently to be transcribed from a promoter site contained in the probe. U.S. Pat. No. 5,215,899 to Dattagupta discloses how specific nucleic acid sequences are amplified through the use of a hairpin probe which, upon hybridization with and ligation to a target sequence, is capable of being transcribed. The probe comprises a single stranded self-complementary sequence which, under hybridizing conditions, forms a hairpin structure having a functional promoter region, and further compromises a single stranded probe sequence extending from the 3' end of the hairpin sequence. Upon hybridization with a target sequence complementary to the probe sequence and ligation of the 3' end of the hybridized target sequence to the 5' end of the hairpin probe, the target sequence is rendered transcribable in the presence of a suitable RNA polymerase and appropriate ribonucleoside triphosphate (rNTPs). Amplification is accomplished by hybridizing the desired TNA sequence with the probe, ligating the TNA to the PNA, adding the RNA polymerase and the rNTPs to the separated hybrids, and allowing transcription to proceed until a desired amount of RNA transcription product has accumulated. That method generally and specifically involves the use of hairpin DNA formed with a single stranded unpaired end to anneal a target sequence. When the target sequence is bound, the production of RNA transcription products is enabled. Thus, the method involves the detection of secondary transcription products rather than the use of a nucleic acid binding assembly to directly immobilize and/or localize a target sequence. A CNA could easily bind to the probe, and the lack of complementarity would not necessarily interfere with the formation of a CNA-PNA hybrid which could then support the production of unwanted transcription products.

A CNA bound to the PNA might be detected if the lack of complementarity interferes with the susceptibility of the hybrid CNA-PNA pair to be cut by a restriction endonuclease. In U.S. Pat. No. 5,118,605 to Urdea and U.S. Pat. No. 4,775,619 to Urdea, novel methods for assaying a nucleic acid analyte were provided, which employ polynucleotides having oligonucleotide sequences substantially homologous to a sequence of interest in the analyte, where the presence or absence of hybridization at a predetermined stringency provides for the release of a label from a support. Various techniques are employed for binding a label to a support, whereupon cleavage of either a single or double strand, a label may be released from a support, and the release of the label can be detected as indicative of the presence of particular polynucleotide sequence in a sample. However, this technique has the shortcoming that a CNA-PNA pair could be cut by the restriction endonuclease, even if there is a mismatch, so long as the mismatch was outside of the endonuclease recognition region. This would lead to failure of the assay to identify a CNA-PNA hybrid.

Another method uses a branched DNA probe to detect nucleic acids. U.S. Pat. No. 5,124,246 to Urdea et al. discloses linear or branched oligonucleotide multimers useful as amplifiers in biochemical assays which comprise (1) at least one first single-stranded oligonucleotide unit (PNA) that is complementary to a single-stranded oligonucleotide sequence of interest (TNA), and (2) a multiplicity of second single-stranded, oligonucleotide units that are complementary to a single-stranded labeled oligonucleotide. Although amplified sandwich nucleic acid hybridizations and immunoassays using the multimers are described, the method has the limitation that PNA-CNA hybridization could occur and would result in production of unwanted signal.

In addition to methods for identification of TNAs, methods have been disclosed for the amplification of this DNA. In U.S. Pat. No. 5,200,314 to Urdea, an analyte polynucleotide strand having an analyte sequence (TNA) is detected within a sample containing polynucleotides by contacting the analyte polynucleotide with a capture probe (PNA) under hybridizing conditions, where the capture probe has a first binding partner specific for the TNA, and a second binding sequence specific for a solid phase third binding partner. The resulting duplex is then immobilized by specific binding between the binding partners, and non-bound polynucleotides are separated from the bound species. The analyte polynucleotide is optionally displaced from the solid phase, then amplified by PCR. The PCR primers each have a polynucleotide region capable of hybridizing to a region of the analyte polynucleotide, and at least one of the primers further has an additional binding partner capable of binding a solid-phase binding partner. The amplified product is then separated from the reaction mixture by specific binding between the binding partners, and the amplified product is detected. Although it is possible to confirm (by PCR) that a particular nucleic acid has hybridized the PNA, confirmation is expensive and involves multiple steps.

As for reports that involve the interaction of a double stranded nucleic acid and a DNA-binding protein, a method has been described whereby a sequence of immobilized DNA which contains binding sites for a single protein is used to purify that protein. U.S. Pat. No. 5,122,600 to Kawaguchi et al. discloses a DNA-immobilized microsphere comprising DNA chains having base sequences which specifically bind a particular protein, and a carrier having a particle size of not more than 50 $\mu$m and not less than 0.01 $\mu$m which does not adsorb any protein, said carrier and said DNA chains being bound to each other by a chemical bond, and a process for purifying a protein using said microsphere. As this is a purification method for a protein, it does not disclose a method of detection of a TNA nor a method whereby more than one protein is bound to a double stranded nucleic acid for the purposes of detection and localization of specific TNA sequences.

In EP 0 453 301, a method for detecting a polynucleotide target sequence in a sample was described, wherein sequences in a TNA are detected by hybridizing a first and a second PNA to the TNA Each of said first and second PNAs contained a pre-formed duplex sequence, or a duplex that is formed through chain extension, capable of binding a nucleotide sequence specific binding protein. A method for binding a nucleotide specific binding protein to a duplex formed between a TNA and a PNA only upon formation of a perfect duplex between the PNA and TNA is neither disclosed nor suggested.

In U.S. Pat. No. 4,556,643, a method was disclosed for the non-radioactive detection of specific nucleotide sequences in a sample which involved hybridization of a probe containing DNA binding protein specific sequences. However, this disclosure neither taught nor suggested a method for binding a nucleotide specific binding protein to a duplex formed between a TNA and a PNA only upon formation of a perfect duplex between sequences present in the PNA and sequences present in the TNA.

BRIEF SUMMARY OF THE INVENTION

Disclosed are methods by which specific Target Nucleic Acid (TNA) sequences are detected through the use of Probe Nucleic Acids (PNAs) which, upon hybridization with TNAs, are capable of binding Target Binding Assemblies (TBAs). Each TBA binds at least one specific region of the PNA-TNA hybrid pair, the Target Binding Region (TBR). The TBA is comprised of one or more molecules, one or more of which can bind to TBR sequences in a specific and sequence dependent manner. The TBA may comprise one or more piloting sequences, called "PILOTS" or "Asymmetry Sequences," which assemble, or prevent assembly of, TBA components into specific geometric and DNA binding orientations. The PILOTS may assemble specific DNA recognition units or other pilots to which specific DNA recognition units are attached into the TBAs in a predetermined fashion. The TBA may also contain one or more molecules which anchor or localize the TBA. Novel TBAs having unique discriminating characteristics which surprisingly render the TBAs useful not only as diagnostic tools but also as prophylactic or therapeutic compounds, are also disclosed. Disclosed are methods and compositions for utilization of the PNAs, TBRs, TBAs, and TBA PILOTS, including their utilization as components of diagnostic and forensic test kits and the utilization of the novel TBAs as prophylactic or therapeutic agents.

The PNAs, in addition to TNA-specific sequences, may also contain one or more sequences, ½ BBRs, capable of hybridizing with complementary ½ BBRs in Booster Nucleic Acids (BNAs). Through hybridization of added BNAs to the starter ½ BBRs present in the PNAs, extensions of the PNAs are made in the form of PNA-BNA and then BNA-BNA hybrids. These extensions can contain one or more Booster Binding Regions (BBRs). Each BBR is capable of binding a Booster Binding Assembly (BBA). The BBA is comprised of molecules, one or more of which can bind to a BBR in a specific and sequence dependent manner. The BBA may comprise one or more piloting sequences, called "PILOTS" or "Asymmetry Sequences," which assemble, or prevent assembly of, TBA components into specific geometric and DNA binding orientations. The PILOTS may assemble specific DNA recognition units or other pilots to which specific DNA recognition units are attached into the BBAs in a predetermined fashion. The BBA may contain molecules which anchor or localize the BBA or which allow for detection of the bound BBAs and thereby of the TBA-TNA-PNA complexes to which they, in turn, are bound. Disclosed are methods and compositions for utilization of the ½ BBRs, BNAs, BBRs, BBAs, and BBA PILOTS, including their utilization as components of diagnostic and forensic test kits.

Methods and compositions are disclosed for the use of Hairpin Nucleic Acids (HNAs) as capping structures. The HNAs contain a self-hybridizing region and a single stranded ½ BBR which, under hybridizing conditions, can hybridize directly to the ½ BBRs in the PNAs or the ½ BBRs in BNAs already bound to the PNAs to terminate the extension of BNAs onto the PNA or onto other BNAs.

Methods and compositions are disclosed for test procedures and the production of a test kit containing PNAs, TBAs, TBRs, BNAs, BBRs, BBAs and HNAs for the detection, localization and differentiation of specific nucleic acid sequences, including nucleic acid sequences which are found in human cells, in the Human Immunodeficiency Virus (HIV), Human Papillomavirus (HPV), and in other nucleic acid containing systems including viruses and bacteria.

BRIEF DESCRIPTION OF THE DRAWINGS

The following illustrations are contained in FIG. 1.

Figure 1:
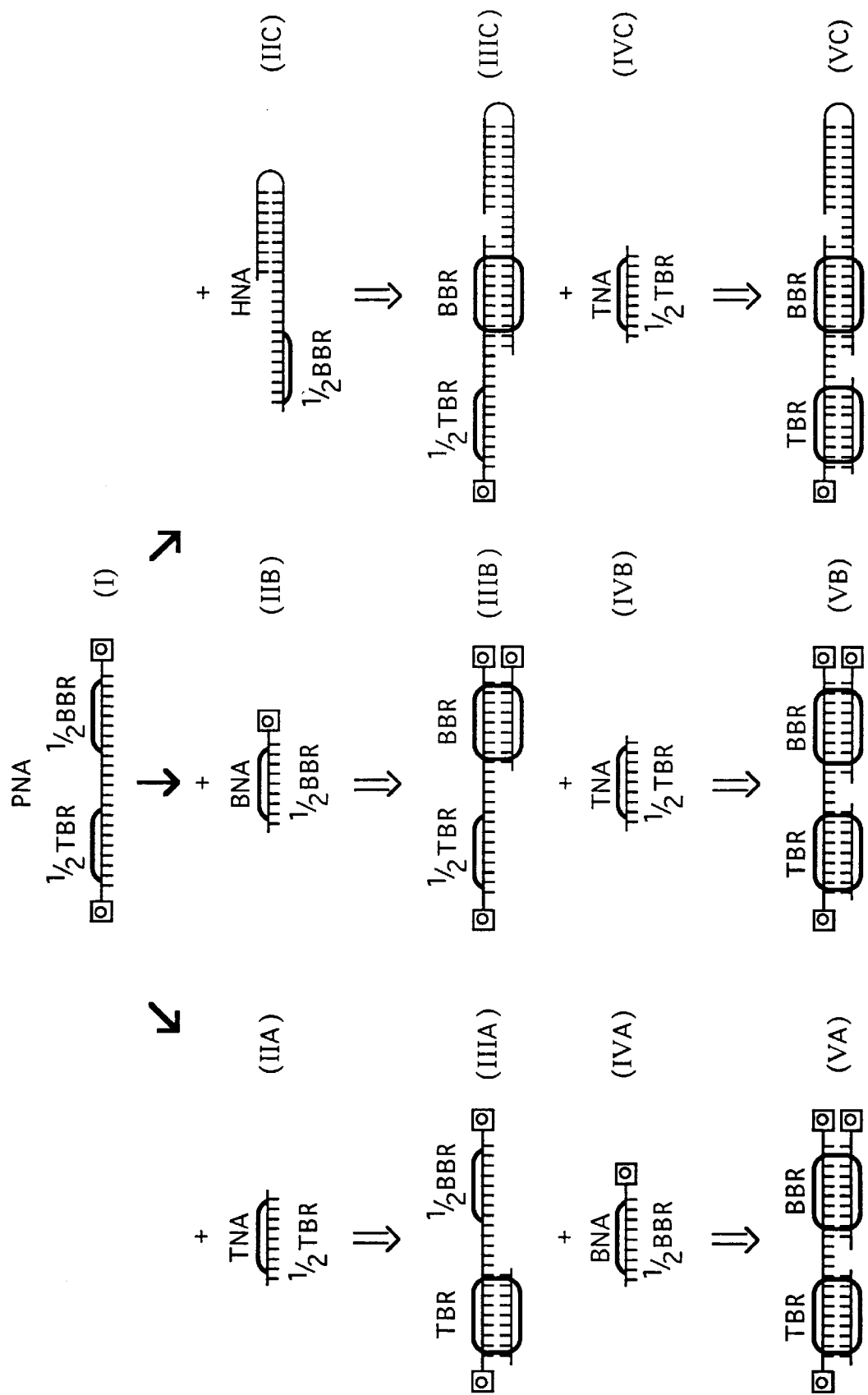
FIG. 1-I is a PNA containing a ½ TBR, which is a single-stranded sequence which is complementary to a TNA and a ½ BBR sequence. (IIa) is a TNA to which is added the components of FIG. 1-I, and, under hybridizing conditions, binds the PNA to form the components of (IIIa), a PNA-TNA hybrid containing at least one TBR. (IVa) is a BNA which is added to the components of FIG. 1-IIIa and, under hybridizing conditions, binds the ½ BBR of FIG. 1-IIIa to form a PNA-BNA hybrid containing a BBR shown in (Va).

(IIb) is a BNA which is added the components of FIG. 1-I, and which, under hybridizing conditions, binds the PNA to form the components of (IIIb), a PNA-TNA hybrid containing a BBR. (IVb) is a TNA to which is added the components of FIG. 1-IIIb and which, under hybridizing conditions, binds the ½ TBR of FIG. 1-IIIb to form a PNA-BNA hybrid containing a TBR shown in FIG. 1-Vb.

(IIc) is a HNA which is added to the components of FIG. 1-I and which, under hybridizing conditions, binds the PNA to form the components of (IIIc), a PNA-HNA hybrid containing a BBR. (IVc) is a TNA which is added to the components of FIG. 1-IIIc and which, under hybridizing conditions, binds the ½ TBR of FIG. 1-IIIc to form a PNA-BNA hybrid containing a BBR shown in FIG. 1-Vc.

The hybrids which form the TBRs and BBRs are useful in the present invention. The PNAs and BNAs, as indicated in FIG. 1, may contain no attached support and/or indicator (OSA), or an attached support or other means of localization, including, but not limited to, attachment to beads, polymers, and surfaces, and/or indicators.

Figure 2A:
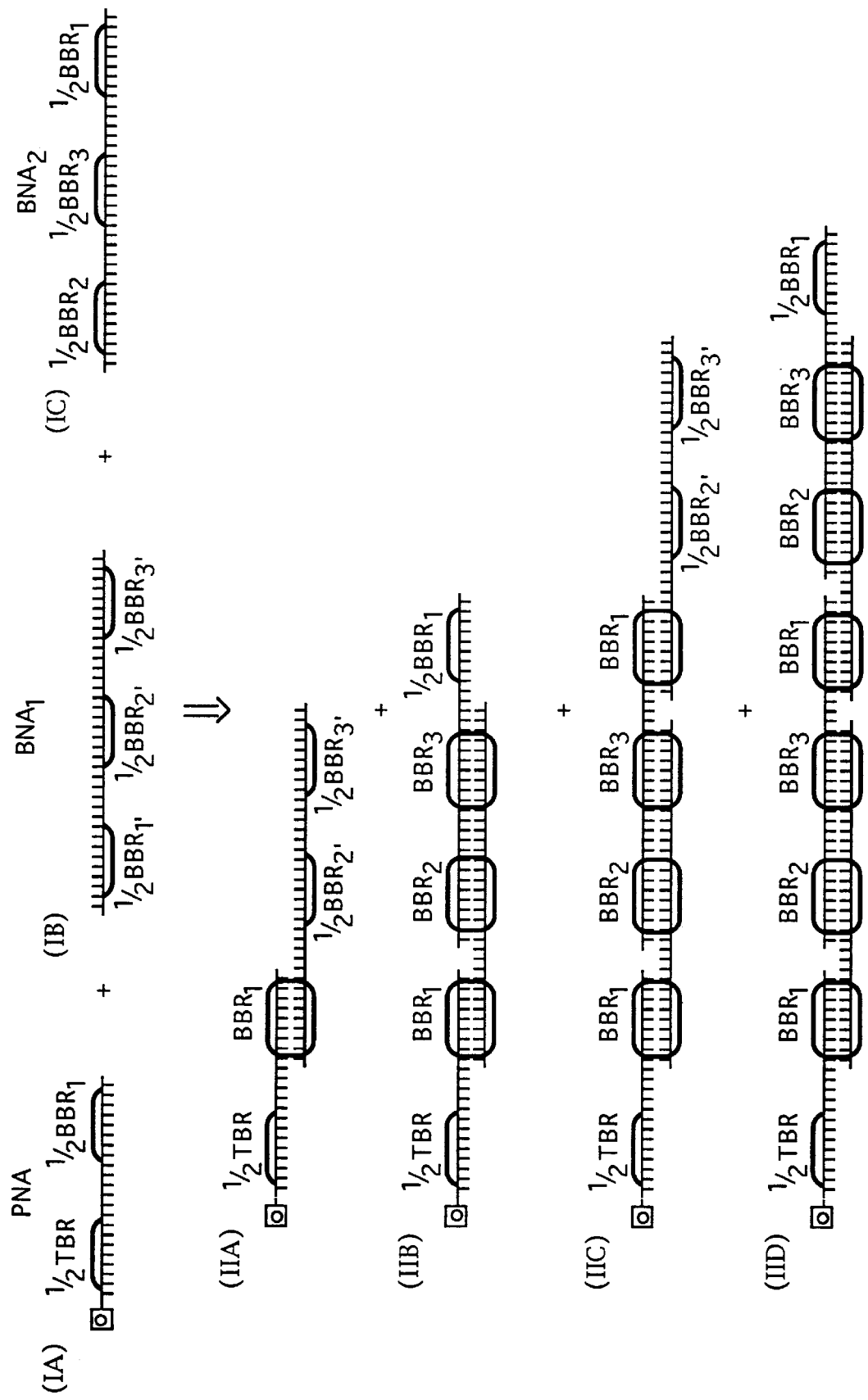
Figure 2B:
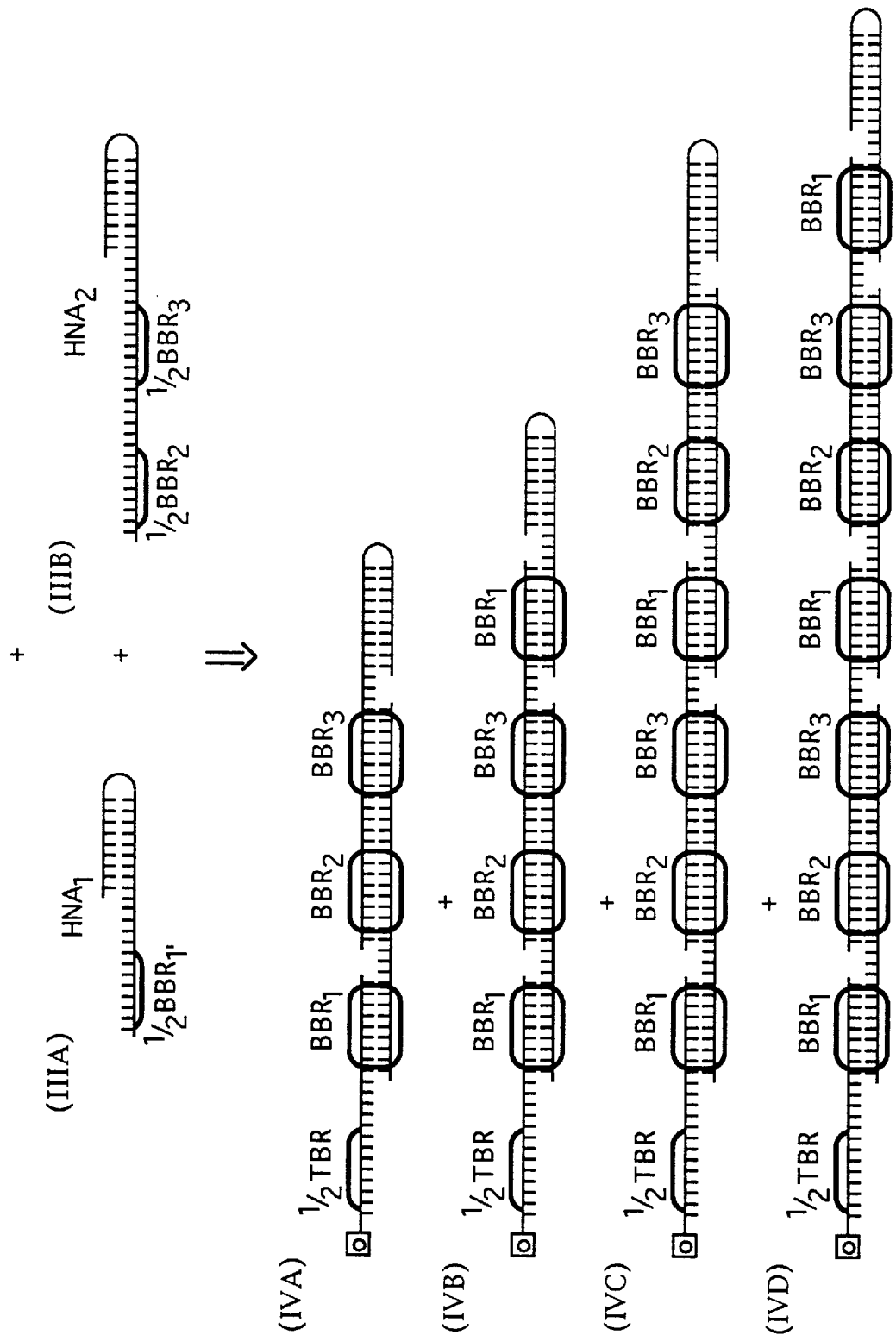

FIGS. 2A–B is a diagram of strategies for polymerization of BNAs onto PNAs and capping by HNAs.

Figure 2C:
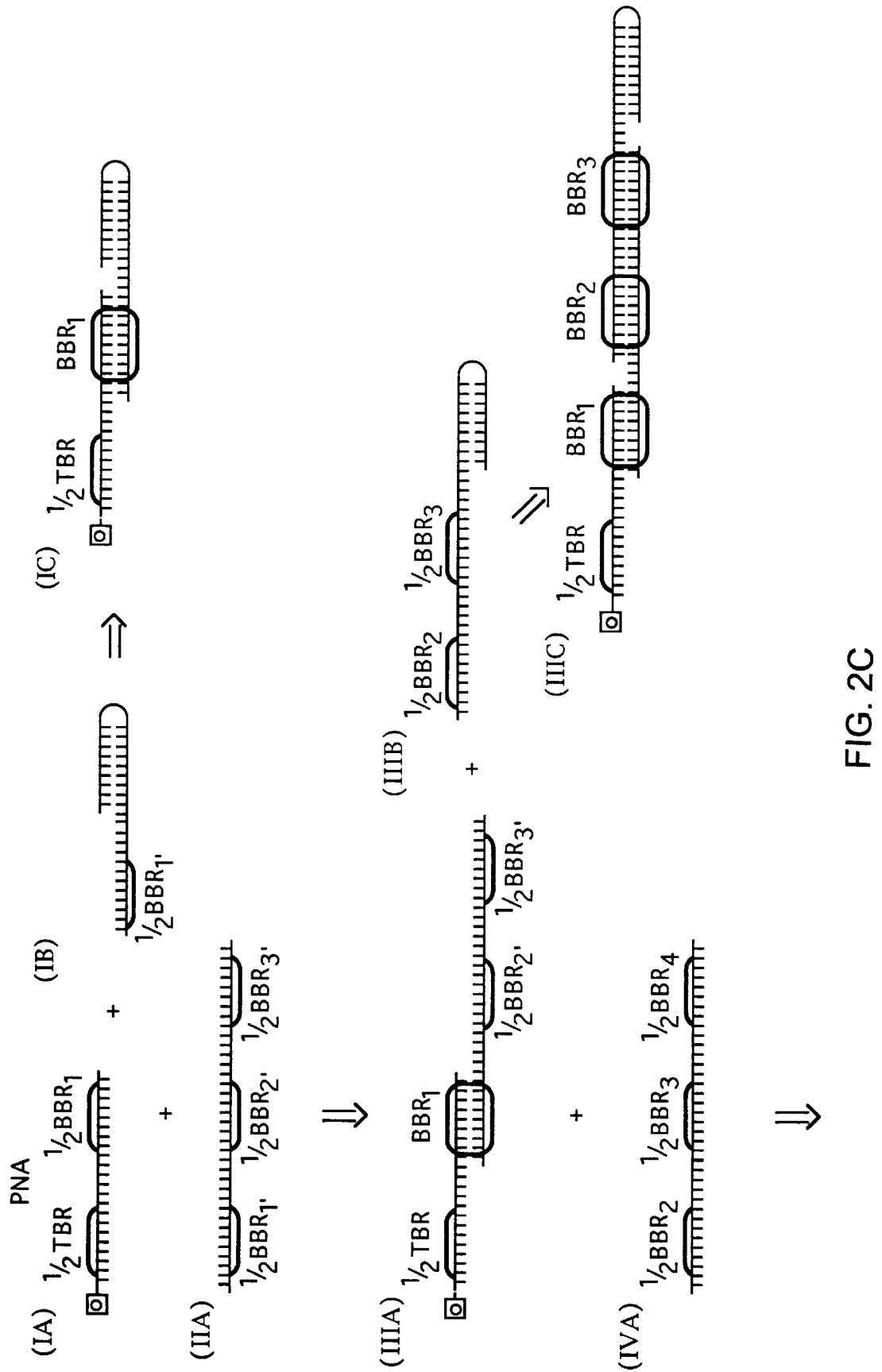
Figure 2D:
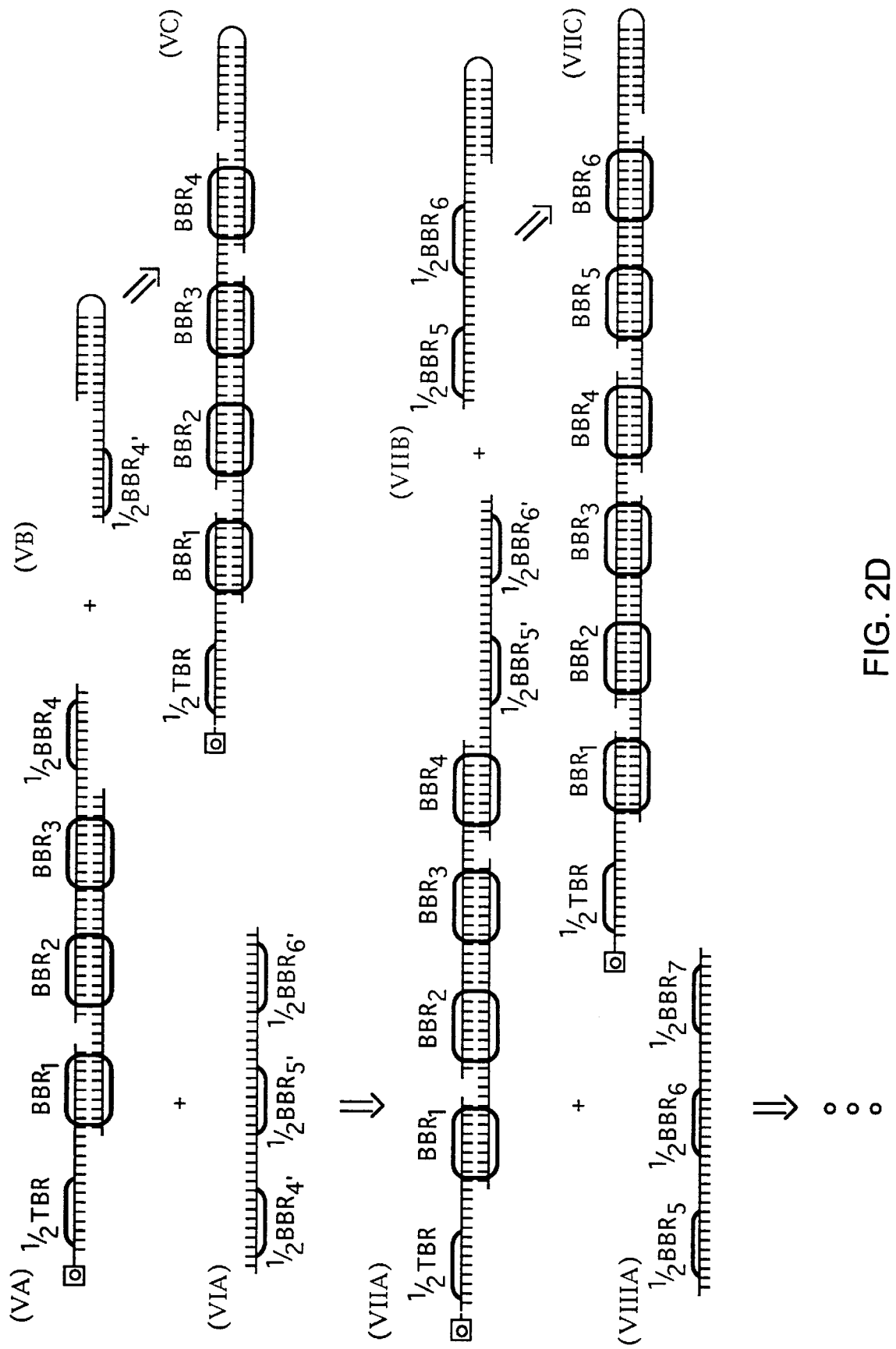

FIGS. 2C–D is a diagram of additional strategies for amplifying PNA-TNA signals via polymerization of BNAs and capping by HNAs.

Figure 3A:
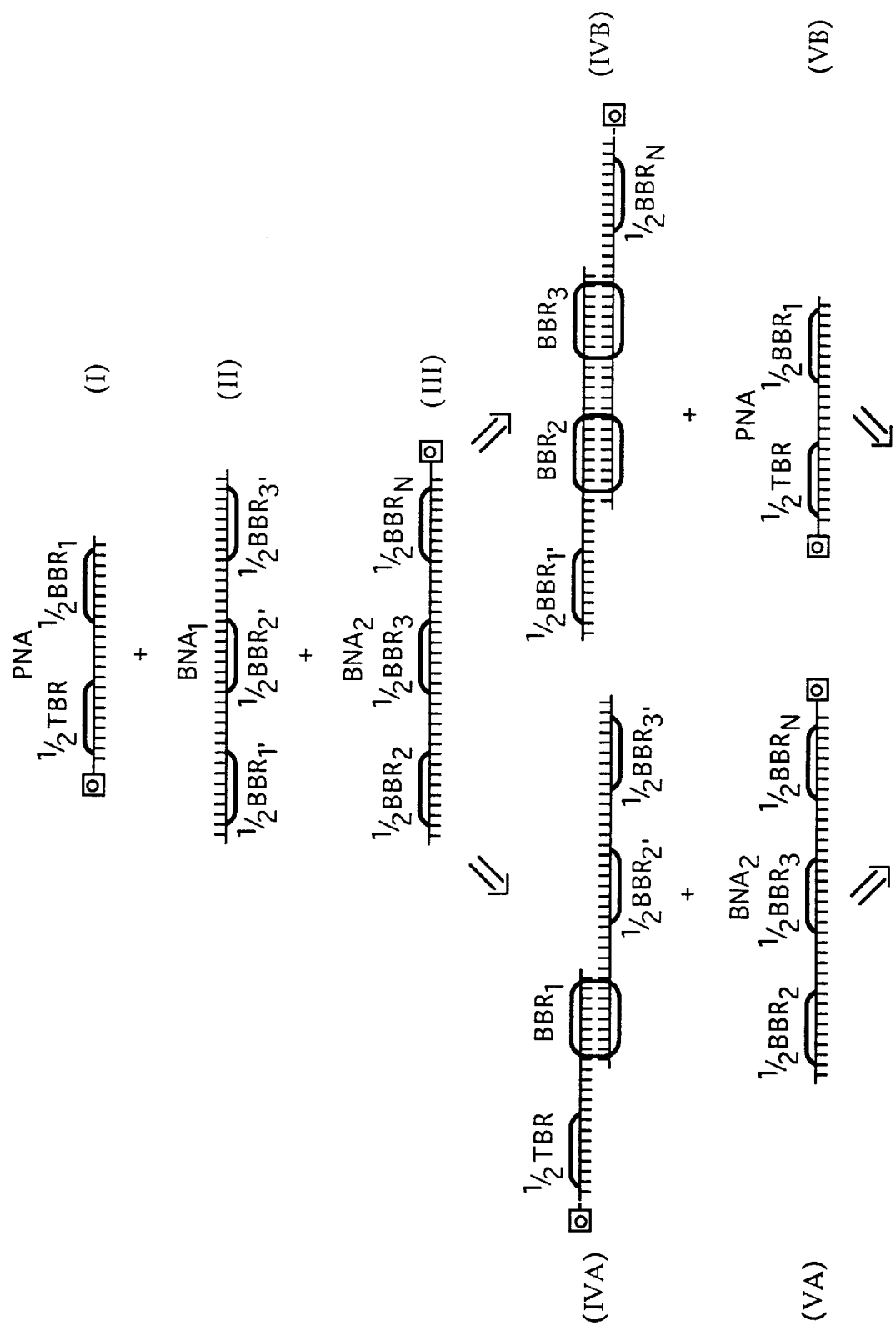
Figure 3B:
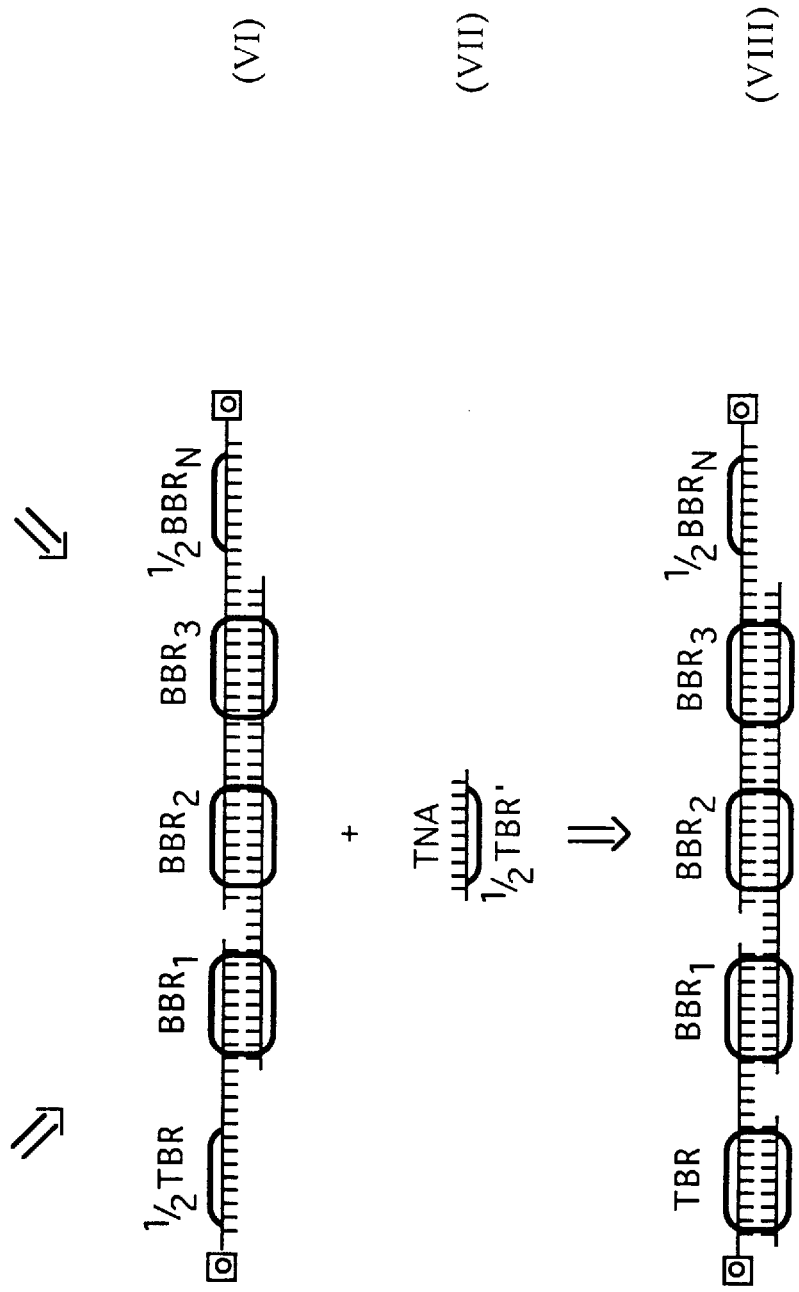

FIGS. 3A–B is a diagram showing the use of BNAs containing multiple ½ BBRs per BNA.

Figure 4A:
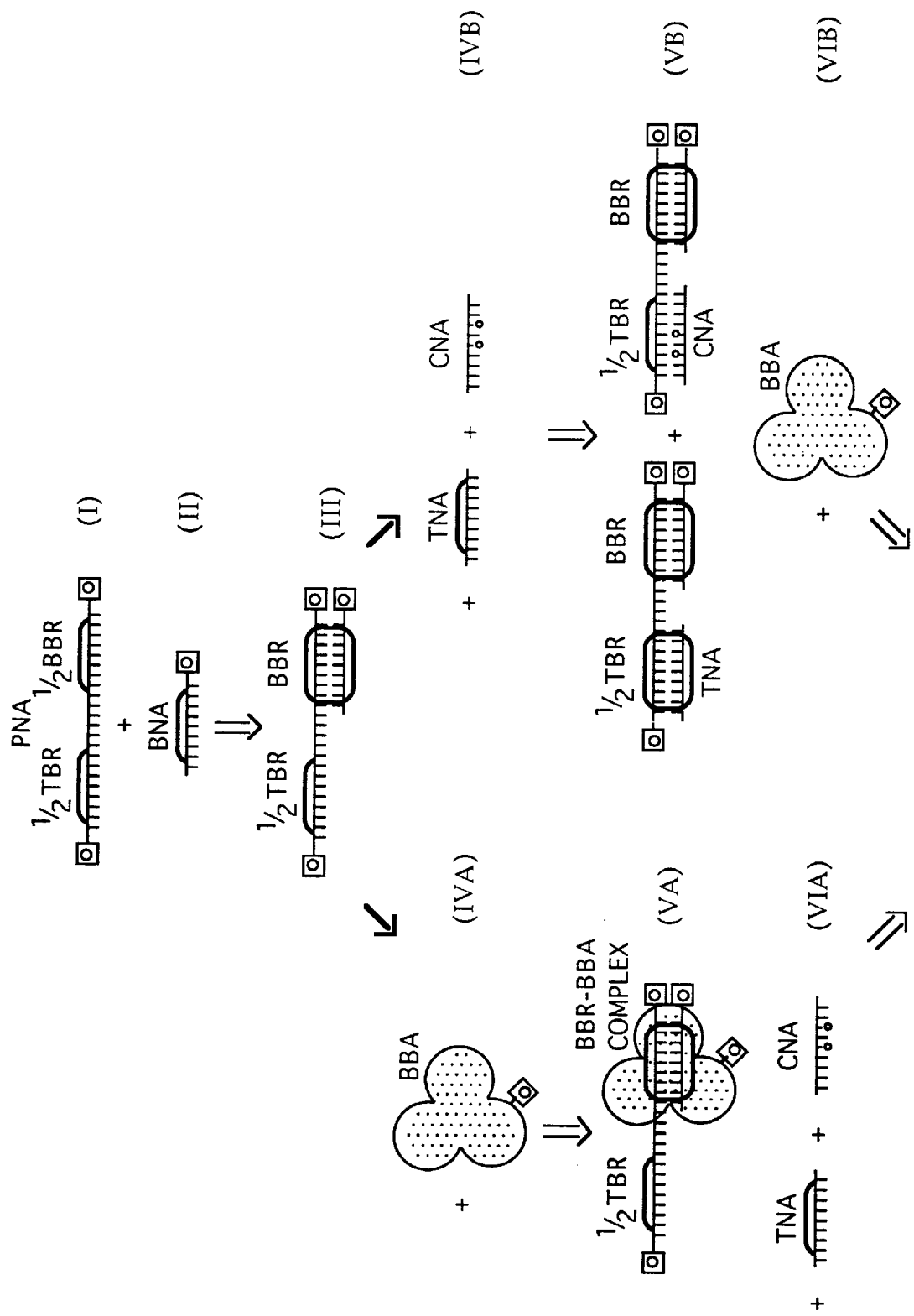
Figure 4B:
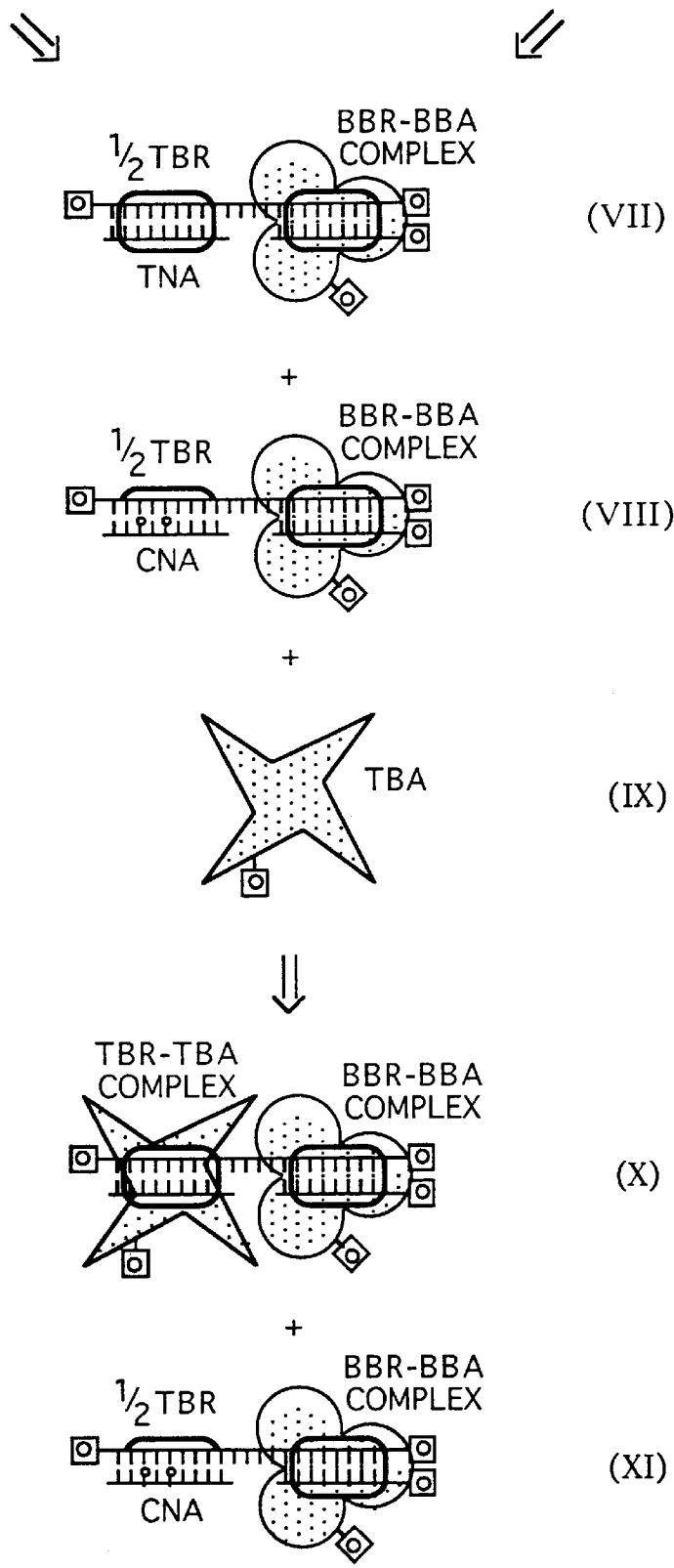

FIGS. 4A–B is a diagram showing the binding of TBAs and BBAs to TBRs and BBRs, and the ability of the TBA to discriminate between TNAs and CNAs. According to this embodiment, if the TBA is immobilized, either on a bead, microtiter plate surface, or any other such surface, only complexes such as complex X would be retained and detected, while complexes such as complex XI would not.

Figure 4C:
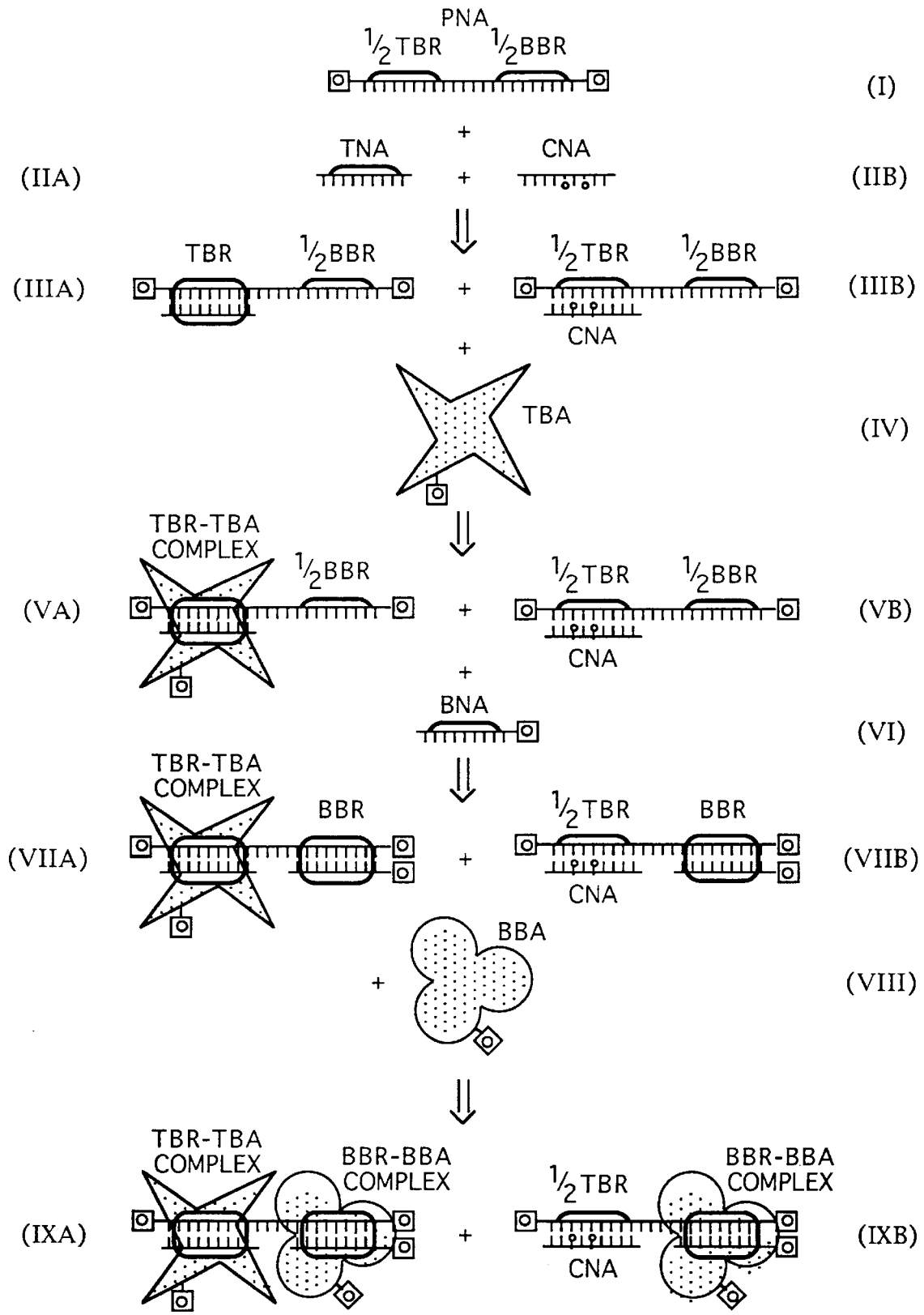

FIG. 4C is a diagram exemplifying events similar to those shown in FIG. 4a but in a slightly different order of occurrence.

Figure 5:
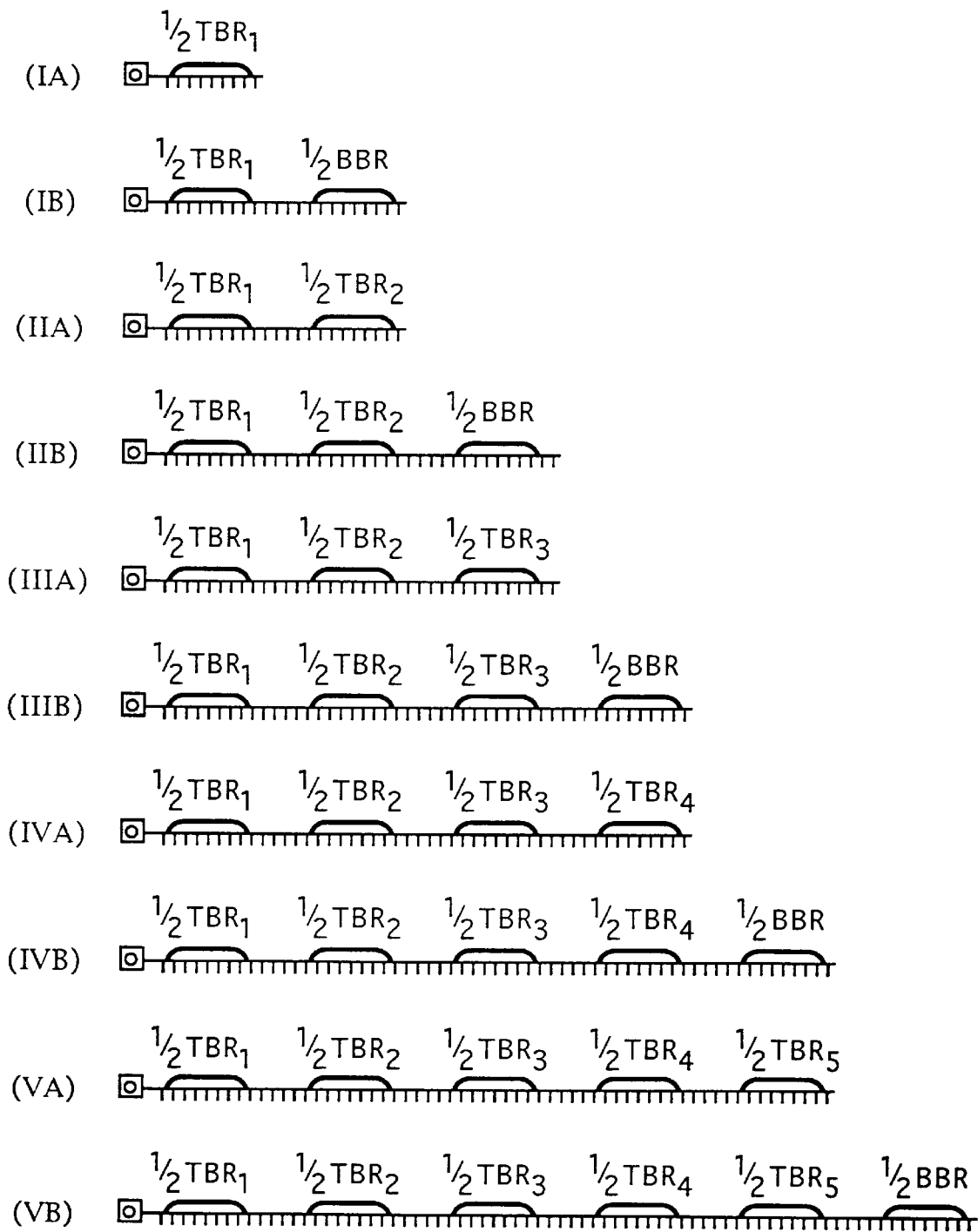

FIG. 5 is a diagram exemplifying PNAs containing between one ½ TBR and no ½ BBR to PNAs containing up to five ½ TBRs and one ½ BBR. The (a) and (b) members of each numeral (I, II, III, IV, V) form a set which, upon hybridization to a TNA, provide TBRs either with ((a) members) or without ((b) members) an available ½ BBR for amplification via hybridization to BNAs having complementary ½ BBRs.

Figure 6A:
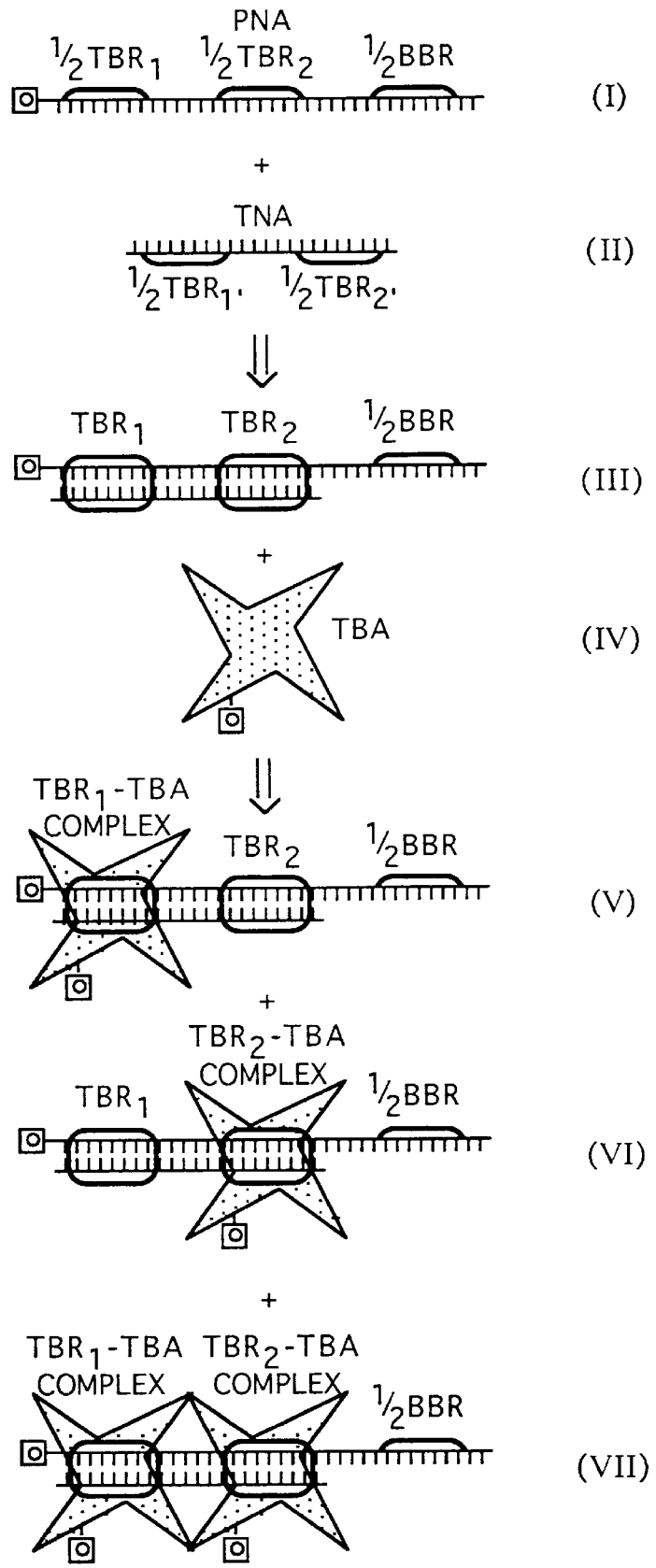

FIG. 6A is a diagram exemplifying a particular TNA having two ½ TBRs which, upon binding an appropriate PNA, forms two closely associated TBRs capable of binding two TBAs. A ½ BBR is also provided for amplification.

Figure 6B:
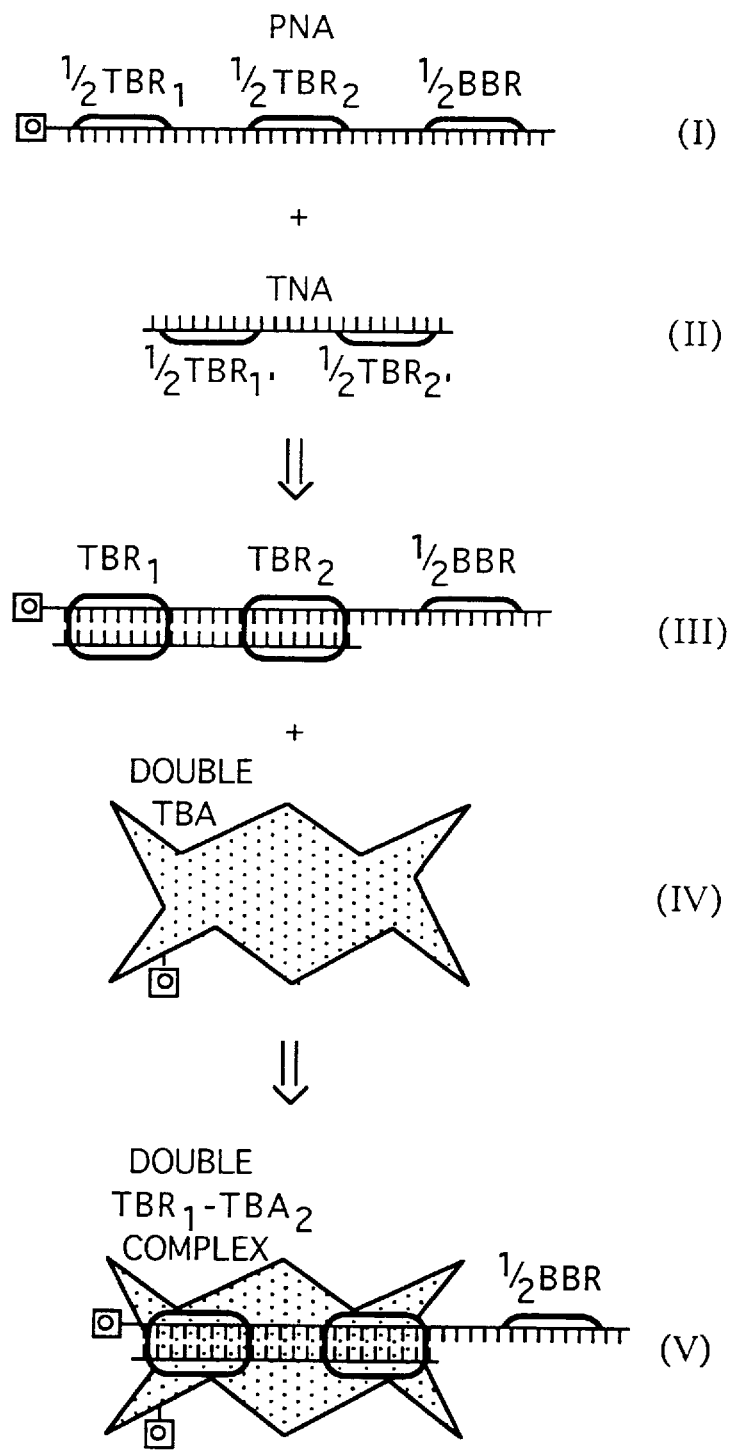

FIG. 6B is a diagram showing the same events as in FIG. 6a except here, a double TBA is used so that discrimination between single TBRs that occur in normal cellular samples may be discriminated from abnormal, double TBRs.

Figure 6C:
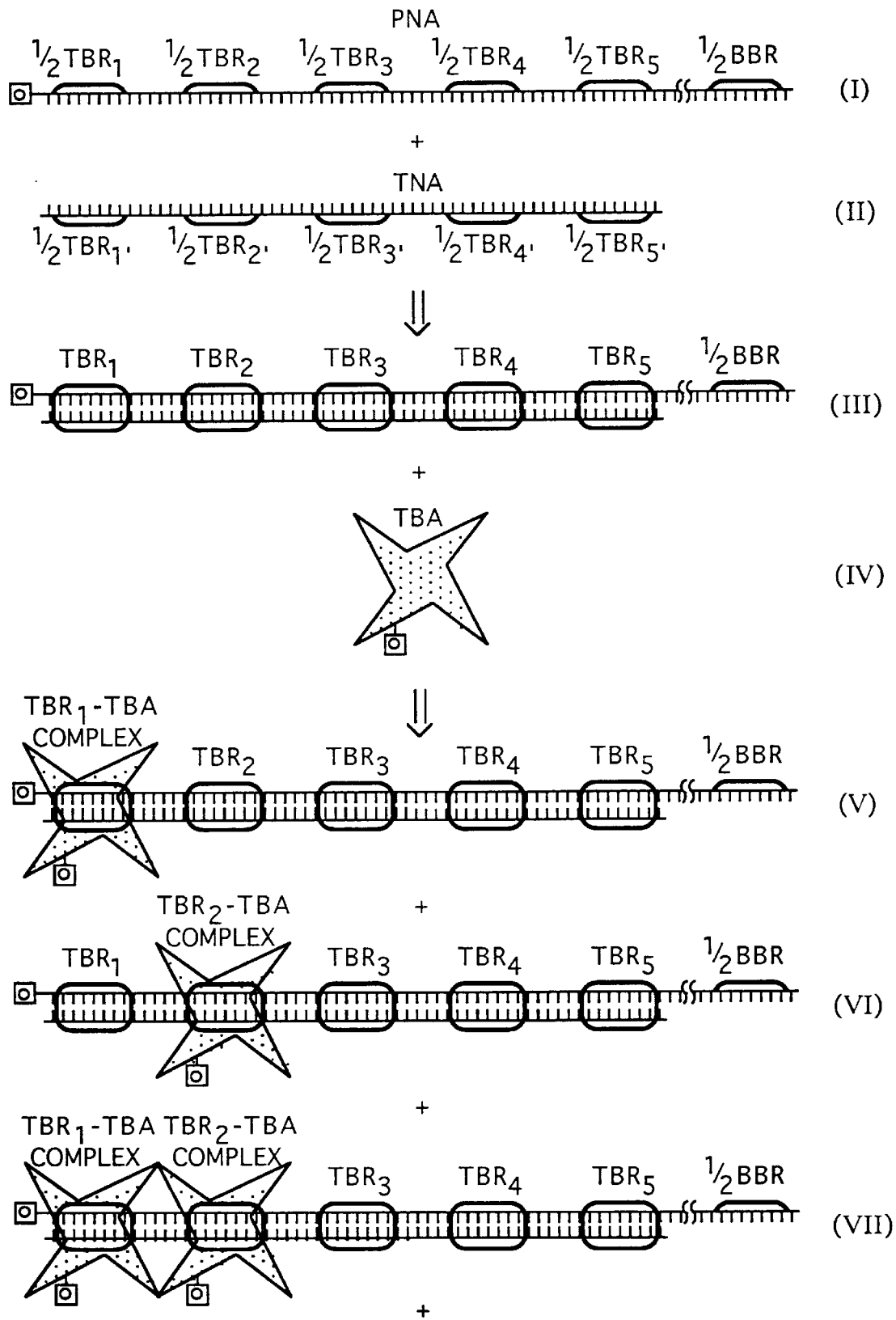
Figure 6D:
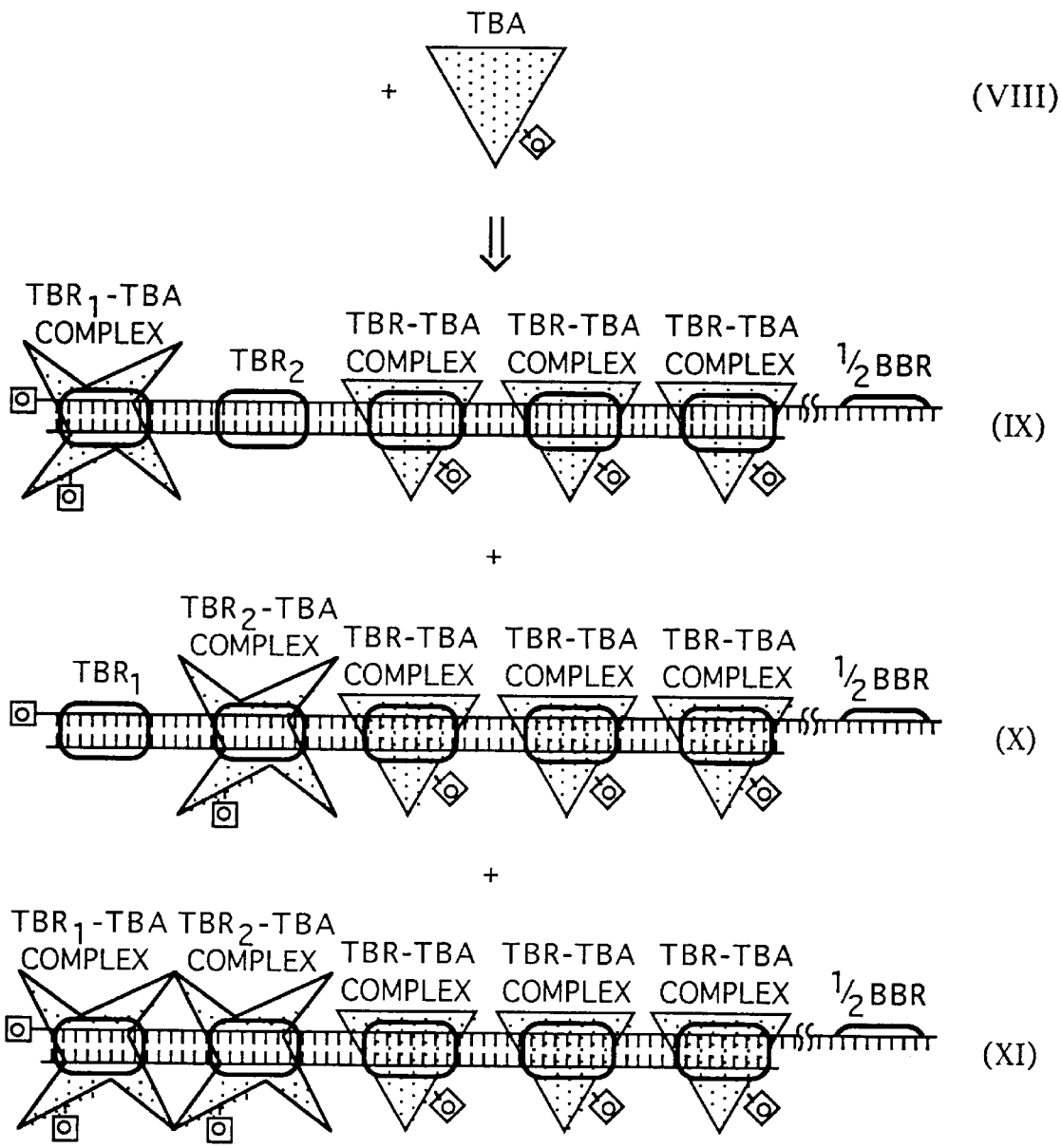

FIGS. 6C–D is a diagram showing the same scenario as in FIG. 6a except that here, five TBRs are identified in the TNA. Each TBR maybe bound to a TBA same or different, and each TBA may be differentially labeled, allowing for confirmation that all five sites are present in the TNA.

Figure 6E:
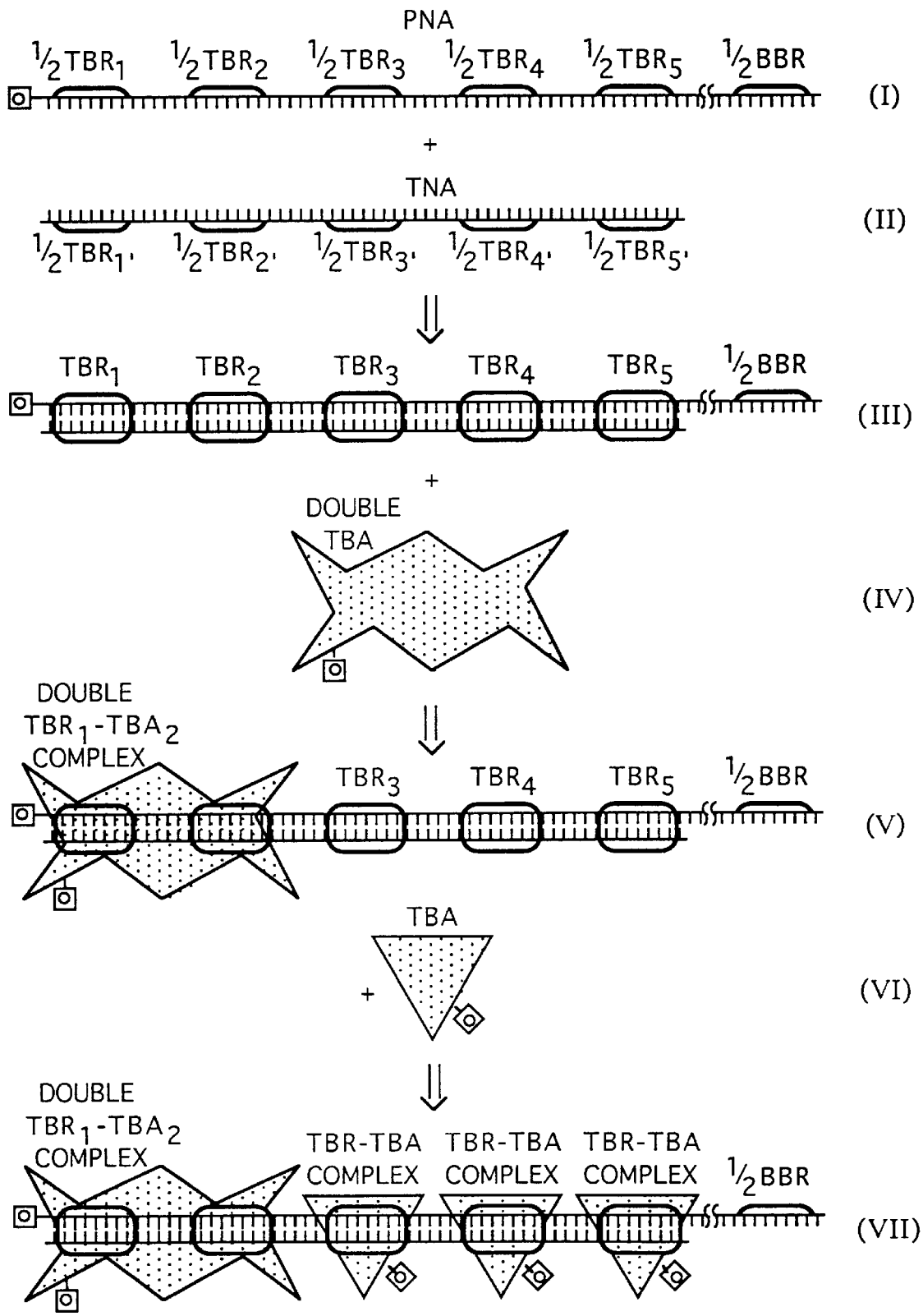

FIG. 6E is a diagram of the same events as in FIG. 6c except here, a double TBA is shown, extending what is shown in FIG. 6b to the use of the double TBA. An example of the TNA shown in item II in FIGS. 6a, 6b, 6c and 6d is HIV single stranded DNA or RNA.

FIG. 7 shows the HIV LTR as a TNA, and two PNAs, and a strategy for detection of the TNA using the PNAs.

Figure 8A:
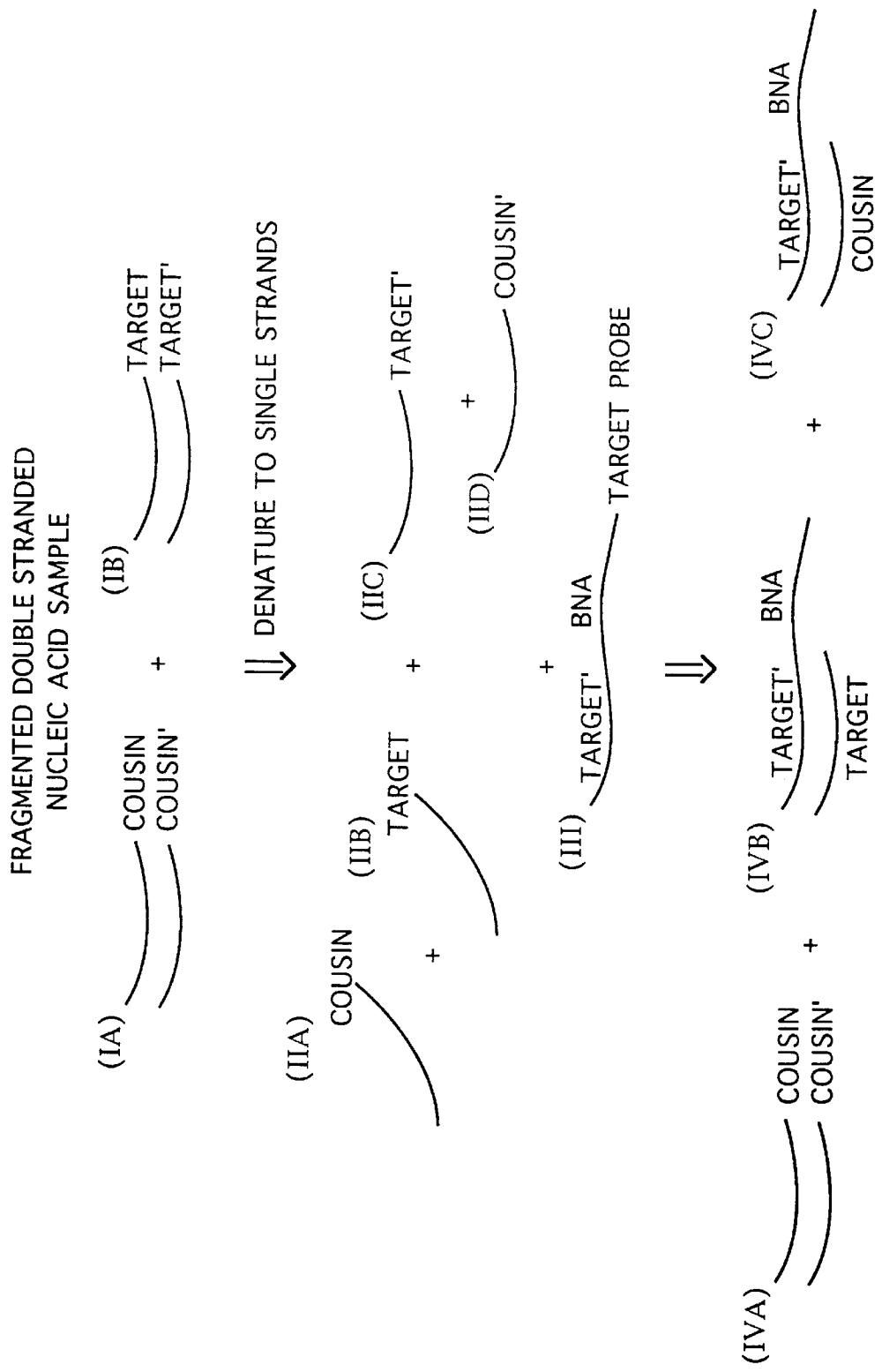

FIGS. 8A–B is a schematic of one embodiment of the invention wherein a target binding assembly is used to bind a hybrid TNA-PNA, and booster binding assemblies are used to bind polymerized BNAs.

Figure 9:
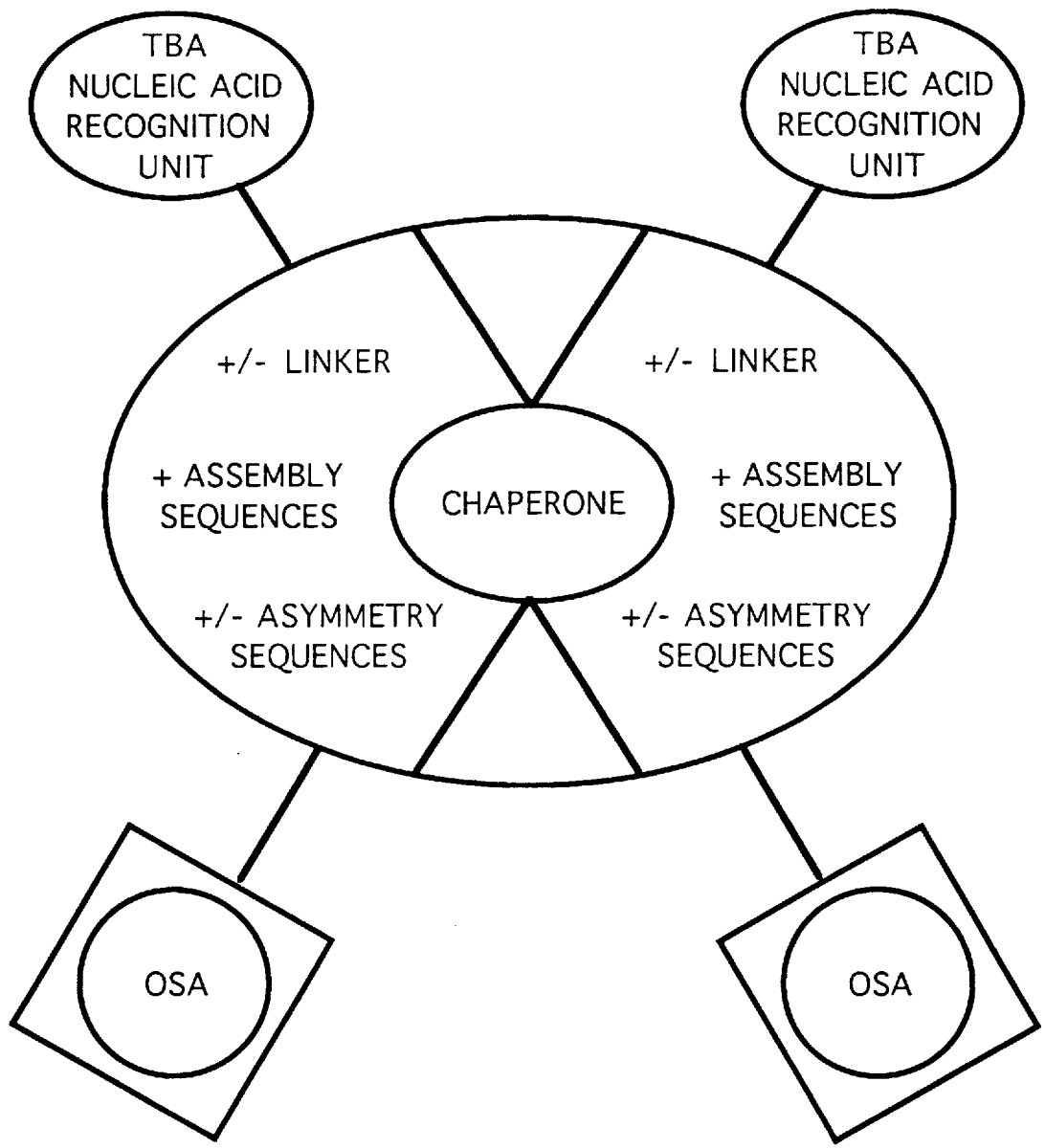

FIG. 9 is a schematic of a modular TBA in which assembly sequences, linker sequences, and asymmetry sequences are used to chaperone desired DNA recognition units together to form a TBA.

FIG. 10 shows modular TBAs useful in detection of HIV-specific sequences.

FIG. 11 shows modular TBAs useful in the detection of human papillomavirus sequences. Each unit of E2 is actually a dimer of the DNA binding portion of E2.

Figure 12A:
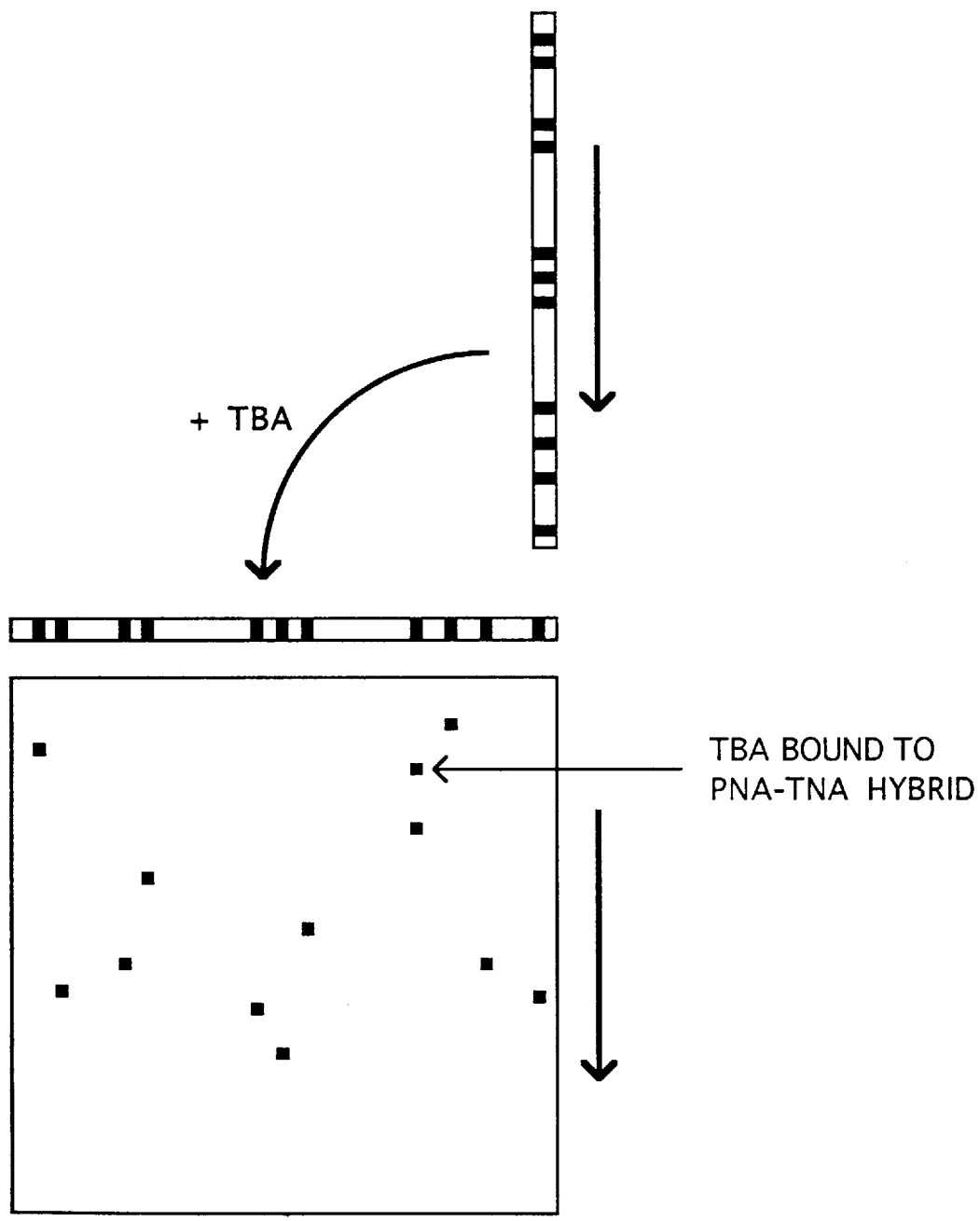

FIG. 12a is a schematic of TNA fractionation and shift in mobility due to binding of a TBA.

Figure 12B:
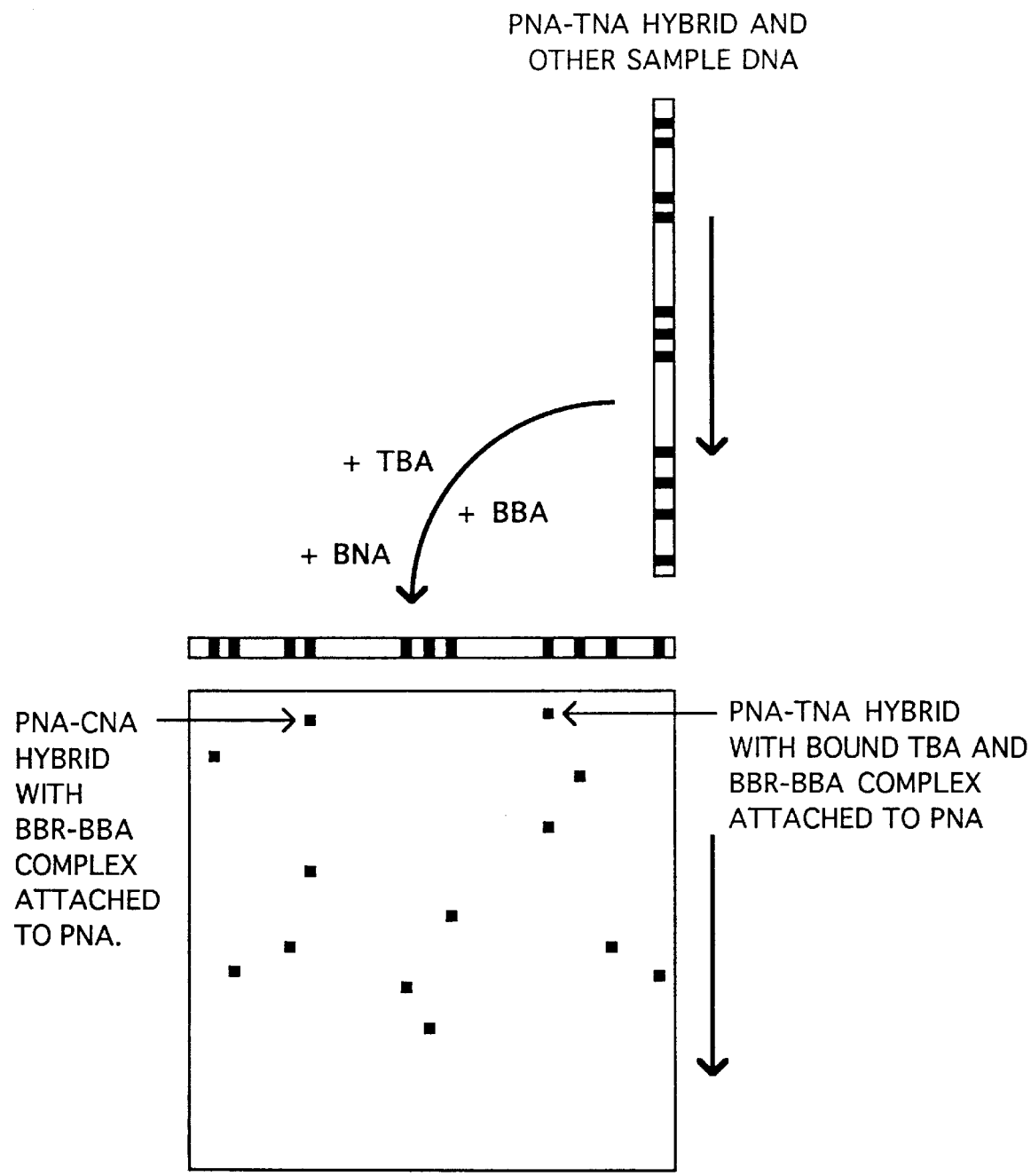

FIG. 12b is a schematic of TNA fractionation and enhanced shift in mobility due to binding of BBAs in addition to TBAs.

Figure 13:
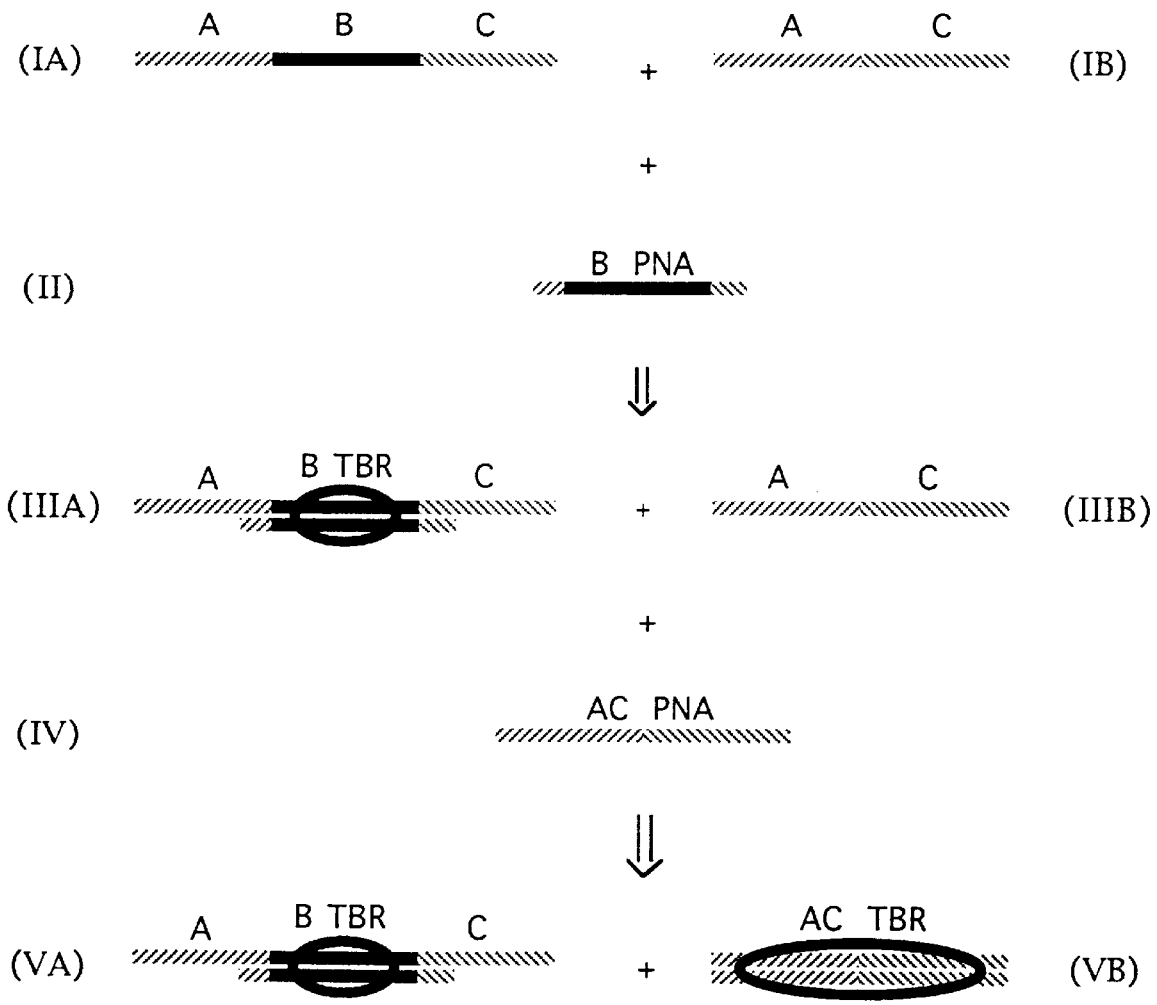

FIG. 13 shows a detection strategy for deletion sequences; an example of use of this strategy is for a human papillomavirus integration assay.

Figure 14:
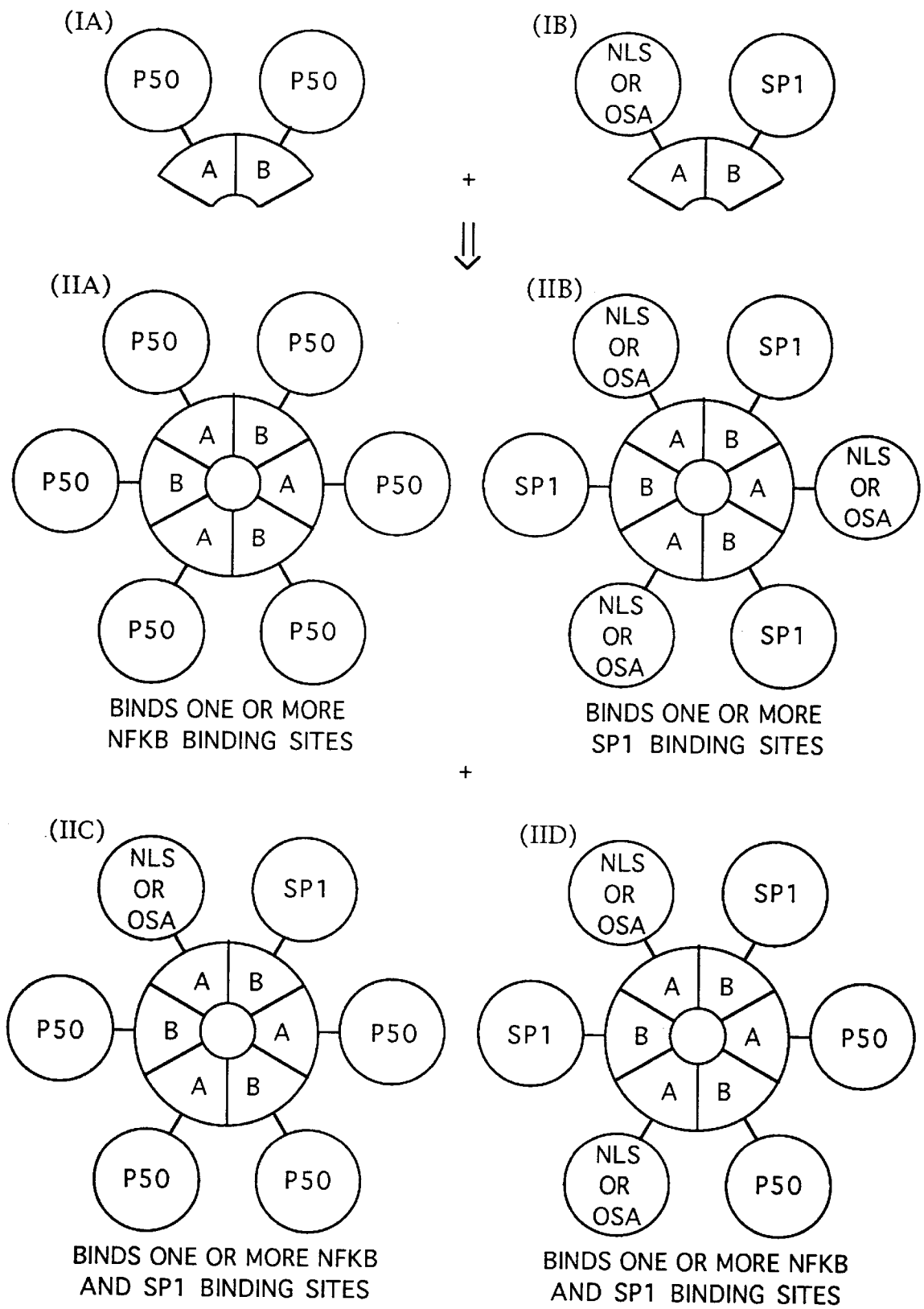

FIG. 14 shows assembly of higher order TBAs through use of DNA recognition units, linker, assembly, and asymmetry sequences such that various Target Binding Assemblies specific to binding sites in the HIV LTR are formed.

Figure 15:
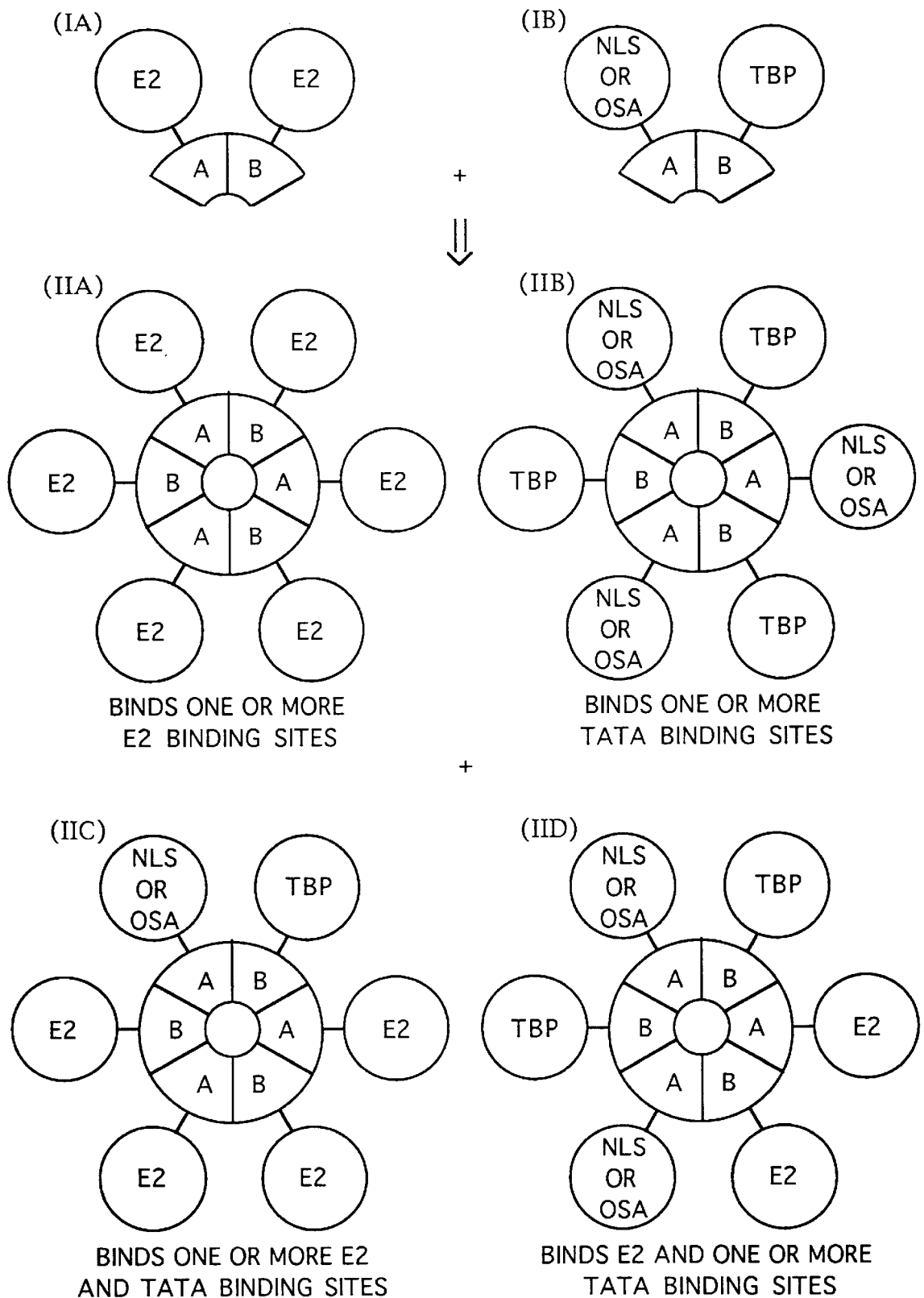

FIG. 15 shows assembly of higher order TBAs through use of DNA recognition units, linker, assembly, and asymmetry sequences such that various Target Binding Assemblies specific to binding sites in the HPV genome are formed.

BRIEF DESCRIPTION OF THE SEQUENCES

SEQ ID NO. 1 corresponds to FIG. 5-Ia-1 and shows the class I MHC NF-kB binding site.

SEQ ID NO. 2 corresponds to FIG. 5 (Ia) and shows the B2-microglobulin NF-kB binding site.

SEQ ID NO. 3 corresponds to FIG. 5 (Ia) and shows the kappa immunoglobulin NF-kB binding site.

SEQ ID NO. 4 corresponds to FIG. 5 (Ia) and shows one of the HIV NF-kB binding sites.

SEQ ID NO. 5 corresponds to FIG. 5 (Ia) and shows one of the HIV NF-kB binding sites.

SEQ ID NO. 6 corresponds to FIG. 5 (Ia) and shows the c-myc NF-kB biding site.

SEQ ID NO. 7 corresponds to FIG. 5 (IIa) and shows a double HIV NF-kB biding site.

SEQ ID NO. 8 corresponds to FIG. 5 (IIa) and shows a double HIV NF-kB biding site.

SEQ ID NOS. 9–16 correspond to FIG. 5 (IIa) and show a double binding site with one site being an HIV NF-kB biding site, and the other site being an HIV SP1 binding site.

SEQ ID NOS. 17–18 correspond to FIG. 5 (IIa) and show a double HIV SP1 biding site.

SEQ ID NOS. 19–31 correspond to FIG. 5 (IIIa) and show a double HIV NF-kB biding site and an HIV SP1 binding site.

SEQ ID NOS. 32–33 correspond to FIG. 5 (IVa) and show a quadruple binding site where two sites are HIV NF-kB biding sites and two sites are HIV SP1 binding sites.

SEQ ID NO. 34 corresponds to FIG. 5 VIa) and shows a quintuple binding site where two sites are HIV NF-kB biding sites and three sites are HIV SP1 binding sites.

SEQ ID NO. 35 is an example of a ½ BBR, in this case the OL1, OL2 and OL3 elements of the bacteriophage lambda left operator, including intervening sequences.

SEQ ID NO. 36 is an example of a ½ BBR, in this case the OR3, OR2 and OR1 elements of the bacteriophage lambda right operator, including intervening sequences.

SEQ ID NO. 37 is the HIV LTR.

SEQ ID NO. 38 is a PNA complementary to PNA of the HIV LTR.

SEQ ID NO. 39 is a PNA complementary to a different PNA of the HIV LTR than SEQ ID NO. 38.

SEQ ID NO. 40 is a PNA complementary to part of the HIV LTR and it also contains a ½ BBR and an overhang sequence for polymerizing BNAs onto the PNA.

SEQ ID NO. 41 is a BNA complementary to the SEQ ID NO. 40 ½ BBR.

SEQ ID NO. 42 is a BNA that will polymerize onto the SEQ ID NO. 41 BNA and which, with SEQ ID NOS. 40 and 41, creates a PstI recognition site.

SEQ ID NO. 43 is a BNA that is complementary to the SEQ ID NO. 42 BNA and which completes a BamHI recognition site.

SEQ ID NO. 44 is an HNA which has a BamHI recognition site that will hybridize with the BamHI recognition site created by SEQ ID NOS. 42 and 43 to the growing polymer.

SEQ ID NO. 45 is a second PNA which, like SEQ ID NO. 40, is complementary to part of the HIV LTR, but not to the same sequence as SEQ ID NO. 40. SEQ ID NO. 45 also encodes a ½ BBR and an overhang which will allow polymerization of BNAs starting with a Sph1 recognition site.

SEQ ID NOS. 46–62 are human papillomavirus (HPV) specific PNAs which, upon hybridization with HPV sequences, form TBRs which bind HPV DNA binding proteins.

SEQ ID NOS. 63–71 are NF-kB DNA recognition units for incorporation into TBAs.

SEQ ID NO. 72 is a nuclear localization sequence.

SEQ ID NO. 73 is a SP1 sequence recognition unit.

SEQ ID NO. 74 is a TATA binding protein recognition unit.

SEQ ID NOS. 75–84 are papillomavirus E2 DNA recognition units.

SEQ ID NOS. 85–92 are asymmetry sequences.

SEQ ID NO. 93 is an arabidopsis TATA binding protein recognition unit.

SEQ ID NO. 94 is an HPV-16-E2-1 DNA binding protein recognition unit.

SEQ ID NO. 95 is an HPV-16-E2-2 DNA binding protein recognition unit.

SEQ ID NO. 96 is an HPV-18-E2 DNA binding protein recognition unit.

SEQ ID NO. 97 is an HPV-33-E2 DNA binding protein recognition unit.

SEQ ID NO. 98 is a bovine papillomavirus E2 DNA binding protein recognition unit.

SEQ ID NOS. 99–102 are exemplary linker sequences.

SEQ ID NO. 103 is an exemplary nuclear localization signal sequence (NLS).

SEQ ID NOS. 104–108 are exemplary chaperone sequences.

SEQ ID NOS. 109–116 are exemplary assembled TBA sequences.

SEQ ID NO. 117 is a consensus NF-kB binding site.

Abbreviations

| Abbreviations | |
|---|---|
| ||||||||||||||||| | single stranded nucleic acid |
| ||||||||||||||||| ||||||||||||||||| | double-stranded nucleic acid |
| (binding region box) | binding region on DNA |
| ◼--- | no support or indicators, or solid support, or other means of localization, including, but not limited to, attachment to beads, polymers, and surfaces, or indicators = OSA |

-continued

| Abbreviations | |
|---|---|
| BBA | booster binding assembly |
| BBR | booster binding region |
| BNA | booster nucleic acid |
| CNA | cousin nucleic acid |
| ½ BBR | single-stranded region which, when hybridized to the complementary sequence from an HNA or a BNA, can bind a BBA |
| ½ TBR | single-stranded region of the PNA which, when hybridized to the complementary sequence from a TNA, can bind a TBA |
| OSA | optional support or attachment, circle with box |
| PNA | probe nucleic acid |
| TBA | target binding assembly |
| TBR | target binding region |
| TNA | target nucleic acid |
| HNA | Hairpin Nucleic Acid |

DETAILED DISCLOSURE OF THE INVENTION

The present invention provides a method for specifically identifying a target nucleic acid (TNA) in a sample through the use of target binding assemblies (TBAs) which incorporate specific nucleic acid binding proteins. By using probe nucleic acids (PNAs) specific to a given NA sequence, and a TBA which is specific to the duplex form of the INA-PNA sequences, a stable TBA-TNA-PNA complex is formed. By additionally providing specific amplifiable sequences in the PNA, in addition to sequences which specifically contribute to the formation of the TBR recognized by the TBA, the binding of the PNA to the TNA is detected and the detection amplified. For this purpose, any of a number of nucleic acid amplification systems, including polymerase chain reaction, or the use of branched DNA, each branch of which contains a detectable label, may be used. In particular, a novel method of amplification is described herein where the amplifiable portion of the PNA contains sequences onto which booster nucleic acids (BNAs) may be polymerized. Upon formation of each BNA-PNA hybrid, a booster binding assembly (BBA) is provided which specifically binds the hybrid and if detectably labeled, provides essentially unlimited amplification of the original TNA-PNA binding event.

According to this invention, the TNA will be understood to include specific DNA or RNA sequences. The TBA will be understood to be any molecular assembly which can specifically and tightly bind to a formed TNA-PNA hybrid. The TBA will contain one or more molecules whose sequences are sufficient to bind to the TBR. DNA and RNA binding domains which are known can either be used directly as components of the TBA or modified according to the teachings provided herein. The most readily available molecules with such sequences are the DNA-binding domains of DNA-binding proteins. Specifically, many DNA or RNA binding proteins are known which can either be used directly as the known, unmodified protein, or the TBA may be a nucleic acid binding protein, modified according to the specific teachings provided herein. In the latter case, specific modifications that are desirable would include optimization of binding affinities, removal of unwanted activities (such as nuclease activity and reorganization of the TBA in the presence of other molecules with an affinity for components of the TBA), optimization of selectivity of a target sequence over closely related sequences, and optimization of stability.

Examples of DNA binding proteins which could be used according to this invention are the DNA-binding portions of the transcription factor NF-kB (p50 and p65), NF-IL6, NF-AT, rel, TBP, the papilloma virus' E2 protein, sp1, the repressors cro and CI from bacteriophage lambda, and like proteins are well known proteins whose DNA binding portion has been isolated, cloned, sequenced, and characterized. In addition, any other DNA-binding protein or portion of a protein that is necessary and sufficient to bind to a TBR hybrid or a BBR is included. This includes proteins or portions of wild type proteins with altered DNA binding activity as well as protein created with altered DNA-binding specificity, such as the exchange of a DNA-binding recognition helix from one protein to another. In addition, proteins which exhibit nucleic acid binding and other nucleic acid functions, such as restriction endonucleases, could be used as the nucleic acid binding function. Proteins which bind to target regions in DNA-RNA hybrids as well as RNA-RNA hybrids are included. The binding assemblies may be constructed with the use of a molecule which chaperones portions of the binding assembly so that specific component combinations and geometries can be achieved. This molecule is designated here as a PILOT. Pilots can be comprised of proteins or any combination of organic and inorganic materials which achieve the combinatorial selection and/or to induce specific geometries between members of the TBA or BBAs. A chaperone is a stable scaffold upon which a TBA or BBA may be constructed such that the correct conformation of the TBA or BBA is provided while at the same time eliminating undesirable properties of a naturally occurring nucleic acid binding protein. As a specific example of this embodiment, a modified version of the pleiotropic transcription factor, NF-kB, is provided using a modified bacteriophage lambda cro protein as the chaperone. Each NF-kB binding dimer retains the picomolar binding affinity for the NF-kB binding site while at the same time the binding assembly presents several advantageous manufacturing, stability, and specificity characteristics.

In view of the foregoing, the various aspects and embodiments of this invention are described below in detail.

1. The Probe Nucleic Acids (PNAs) and their preparation. The PNAs of the present invention comprise at least three principal parts joined together. With reference to FIG. 1(I) of the drawings, the first part of the PNA is one or more sequences of bases, designated "½ TBR." With reference to FIG. 1(I and IIa) of the drawings, the ½ TBR in the PNA is complementary to a sequence of interest in a sample, the TNA containing a ½ TBR. With reference to FIG. 1(IIIa) of the drawings, the TNA, when added to the PNA under hybridizing conditions, forms a PNA-TNA hybrid containing a TBR. With reference to FIG. 1(I) of the drawings, the second part of the PNA is a sequence of bases, designated "½ BBR." With reference to FIG. 1(I, IIb, IIc, and IVa) of the drawings, the ½ BBR in the PNA is complementary to a ½ BBR contained in a BNA or a HNA. With reference to FIG. 1(IIIb, IIIc, and Va) of the drawings, the BNA or HNA, when added to the PNA under hybridizing conditions, forms a PNA-BNA hybrid or PNA-HNA hybrid, respectively, containing a BBR. With reference to FIG. 1(I) of the drawings, the third part of the PNA is the OSA, designated by a circle with a box around it. The OSA is no support and/or an indicator, or solid support, or other means of localization, including but not limited to, attachment to beads, polymers, and surfaces and/or indicators which is/are covalently attached to, or non-covalently, but specifically, associated with the PNA. The OSA may be an atom or molecule which aids in the separation and/or localization such as a solid support binding group or label which can be detected by various physical means including, but not limited to, adsorption or imaging of emitted particles or light. Methods for attaching indicators to oligonucleotides or for immobilizing oligonucleotides to solid supports are well known in the art (see Keller and Manak, supra, herein incorporated by reference).

The PNA of the present invention can be prepared by any suitable method. Such methods, in general, will include oligonucleotide synthesis and cloning in a replicable vector. Methods for nucleic acid synthesis are well-known in the art. When cloned or synthesized, strand purification and separation may be necessary to use the product as a pure PNA.

The length and specific sequence of the PNA will be understood by those skilled in the art to depend on the length and sequence to be detected in a TNA, and the strictures for achieving tight and specific binding of the particular TBA to be used (see discussion on TBAs below). In general, PNAs of sequence lengths between about 10 and about 300 nucleotides in length are adequate, with lengths of about 15–100 nucleotides being desirable for many of the embodiments specifically exemplified herein.

It should also be understood that the PNA may be constructed so as to contain more than one ½ TBR and to produce more than one TBR for one or more TBAs, same or different, as well as complex TBRs recognized by novel duplex and multiplex TBAs (see description below regarding these novel TBAs) upon hybridization of the PNAs and TNAs. FIG. 5 illustrates specific PNAs which contain one or more ½ TBRs. Specific sequences which correspond to the ½ TBR sequences illustrated in FIG. 5 (Ia, IIa, IIIa, IVa, and Va) are SEQ ID NOS. 1–34 (see Description of Sequences above).

As shown in FIGS. 2A through 2D, the PNA, containing a ½ TBR, may be hybridized with one or more BNAs (see description below) and the chain of BNAs polymerized to any desired potential length for amplification of the TNA-PNA hybridization event. Preferably, between about 0 and about 10 ½ BBRs will be present in the PNA.

As shown in FIGS. 6a and 6b, the PNA may contain several ½ TBRs, same or different, which can hybridize with several ½ TBRs in a TNA. Each time a ½ TBR in the PNA matches a ½ TBR in a TNA, a Target Binding Region, TBR, is formed which can bind a TBA. Furthermore, it is not essential that all of the TBRs be on a single, contiguous PNA. Thus, in one embodiment of the invention, two different PNAs are used to detect sequences on a particular TNA. As an illustration of this aspect of the invention, FIG. 7 shows one representation of the human immunodeficiency virus (HIV) long terminal repeat (LTR). As is known in the art, the HIV LTR comprises two NF-kB binding sites and three SP1 binding sites, in close proximity, wherein NF-kB and SP1 are known DNA binding proteins. FIG. 7 provides two PNAs, PNA1 (SEQ ID NO. 38) and PNA2 (SEQ ID NO. 39), each of which is complementary to the opposite strand shown as a TNA (SEQ ID NO. 37), which shows the two NF-kB binding sites and the three SP1 binding sites of the HIV LTR. According to this aspect of the invention, PNA1 specifically hybridizes with that section of the TNA shown in FIG. 7 with bases underscored with a "+" symbol, while PNA2 specifically hybridizes with that section of the TNA shown in FIG. 7 with bases underscored with an "=" symbol. Each of PNA1 or PNA2 may also contain sequences (indicated by the symbols "#" or "*") which will hybridize with a BNA's ½ BBR sequences (see below). In addition, each of PNA1 and PNA2 may be differentially tagged with an OSA, such as a fluorophore such as a fluorescein or a rhodamine label, which would allow confirmation that both probes have become bound to the TNA. If only one label or neither label is detected, it is concluded that the TNA is not present in the sample being tested.

In a further aspect of the embodiment shown in FIG. 7, a method for altering the specificity of the instant assay method is shown. By changing the length of the gap between PNA1 and PNA2, such that the region of TNA remaining unhybridized is altered, one practicing this invention is able to alter the discrimination of the assay.

In order to more clearly exemplify this aspect of the invention, it is necessary to emphasize that the TBR is a helical structure. Thus, while PNA1 creates TBRs on one "face" of the helix, PNA2 creates a TBR on either the same or a different face of the helix, depending on the distance between the middle of each TBR (underlined in FIG. 7). If the middle of each binding site is an integral product of 10.5 bases apart, the TBRs will be on the same side of the helix, while non-integer products of 10.5 bases apart would place the TBRs on opposite sides of the helix. In this fashion, any cooperativity in binding by the TBA recognizing the PNA1 TBR and the TBA recognizing the PNA2 TBR can be manipulated (see Hochschild, A., M. Ptashne [1986] *Cell* 44:681–687, showing this effect for the binding of bacteriophage lambda repressor to two different operator sites located at different distances from each other in a DNA helix). As described by Perkins et al. ([1993] *EMBO J.* 12:3551–3558), cooperativity between NF-kB and the SP1 sites is required to achieve activation of the HV LTR. However, for the purpose of the instant invention, the double NF-kB-triple SP1 binding site motif in the HIV LTR may be taken advantage of by providing a single, novel binding protein capable of binding both sites simultaneously, but only if the spacing between the sites is geometrically feasible. This is controlled both by the structure of the selected TBA and by the PNAs used. Thus, in the embodiment exemplified in FIG. 7, the two probes may be designed with a large enough interprobe region of single-stranded DNA remaining such that, even if the NF-kB and SP1 binding sites are on opposite sides of the helix, the single-stranded region between the probes provides a sufficiently flexible "hinge" so that the DNA can both bend and twist to accommodate the geometry of the TBA. Alternatively, a more stringent assay may be designed by narrowing the interprobe distance such that the DNA may only bend, but not twist. Finally, the probes may be so closely spaced, or a single PNA used, such that the DNA can only bend but not twist. Thus, this figure exemplifies and enables the production of detection systems with any given desired degree of discrimination between target nucleic acids having similar sequences, but different juxtapositions of these sequences.

In terms of a diagnostic or forensic kit for HIV, those skilled in the art would understand that the aforementioned aspects of this invention allow for the tailoring of the components of the diagnostic or forensic kit to match what is known at any given time about the prevalent strains of HIV or another pathogen or disease condition. It will also be appreciated by those skilled in the art that, while detection of HIV infection is not the only utility of the instant invention, due to the mutability of the HIV genome, it is probably one of the most complex test environments for such a diagnostic. It is precisely in such a mutable environment, however, where the flexibility of the instant method, coupled with its ability to discriminate between very closely related sequences, may be most clearly appreciated. In less mutable environments, some of the sophistication to which this invention is amenable need not be utilized. Thus, in a diagnostic kit for papillomavirus infection, all of the discrimination characteristics of the TBA-TBR interaction are available, along with the ability to amplify the signal using the BNAs and BBAs, but a single, simple PNA, such as any one of SEQ ID NOS. 46–62, may be used which identifies unique papillomavirus sequences, which also are known to bind to a TBA such as the papillomavirus E2 protein or truncated DNA binding portions thereof (see Hegde et al. [1992] *Nature* 359:505–512; Monini et al. [1991] *J. Virol.* 65:2124–2130).

2. The Booster Nucleic Acids (BNAs), Booster Binding Regions (BBRs) and their preparation. The BNAs of the present invention are comprised of at least one or more ½ BBRs coupled to an OSA. The ½ BBRs can hybridize to complementary ½ BBRs contained in the PNA, other BNAs or an HNA.

With reference to FIG. 1(I, IIb and IIIb) of the drawings, the simplest BNA is comprised of two parts. With reference to FIG. 1(IIb) of the drawings, the first part of the simplest BNA is a sequence of bases which is complementary to the sequence in the PNA which is designated "½ BBR." With reference to FIG. 1(IIb) of the drawings, the second part of the simplest BNA is the OSA, designated by a circle with a box around it. The OSA is no support and/or indicator, or solid support, or other means of localization, including but not limited to, attachment to beads, polymers, and surfaces and/or indicators which are covalently attached to, or non-covalently, but specifically, associated with the BNA.

With reference to FIGS. 2A through 2D(II and III) of the drawings, the BNA may contain more than one ½ BBR sequence. The BNA illustrated in FIGS. 3A–B(II) contains a sequence which is complementary to the PNA illustrated in FIGS. 3A–B(I) and two other ½ BBR sequences. The BNA illustrated in FIGS. 3A–B(III) contains two ½ BBR sequences which are complementary to two of the ½ BBR sequences in the BNA illustrated in FIGS. 3A–B(II), plus up to "n" additional ½ BBRs for polymerization of additional BNAs.

Under hybridizing conditions, the BNA illustrated in FIGS. 3A–B(II), when combined with the PNA illustrated in FIGS. 3A–B(I), creates the PNA-BNA hybrid illustrated in FIGS. 3A–B(IVa) containing a BBR and an unhybridized extension with two additional ½ BBR sequences or "booster" sequences. The BBRs created by said hybridization can be identical, similar or dissimilar in sequence. The BBRs created by said hybridization can bind identical, similar or dissimilar BBAs (see below).

Under hybridizing conditions, the BNA-BNA hybrid illustrated in FIGS. 3A–B(IVb), when combined with the PNA illustrated in FIGS. 3A–B(Vb), creates the PNA-BNA hybrid illustrated in FIGS. 3A–B(VI) containing a BBR, two additional BNA-BNA hybrids containing BBRs, and an unhybridized extension with an additional ½ BBR sequence, a "booster" sequence. The BBRs created by said hybridization can be identical, similar or dissimilar in sequence. The BBRs created by said hybridization can bind identical, similar or dissimilar BBAs (see below).

3. The Target Nucleic Acids (TNAs) and their preparation. The first step in detecting and amplifying signals produced through detection of a particular TNA according to the present method is the hybridization of such target with the PNA in a suitable mixture. Such hybridization is achieved under suitable conditions well known in the art.

The sample suspected or known to contain the intended TNA may be obtained from a variety of sources. It can be a biological sample, a food or agricultural sample, an environmental sample and so forth. In applying the instant method to the detection of a particular TNA for the purposes of medical diagnostics or forensics, the TNA may be obtained from a biopsy sample, a body fluid or exudate such as urine, blood, milk, cerebrospinal fluid, sputum, saliva, stool, lung aspirates, throat or genital swabs and the like.

Accordingly, PNAs specific to vertebrates (including mammals and including humans) or to any or all of the following microorganisms of interest may be envisioned and used according to the instant method:

| | |
|---|---|
| Corynebacteria | |
| *Corynebacterium diphtheria* | |
| Pneumococci | |
| *Diplococcus pneumoniae* | |
| Streptococci | |
| *Streptococcus pyogenes* | |
| *Streptococcus salivarius* | |
| Staphylococcus | |
| *Staphylococcus aureus* | |
| *Staphylococcus albus* | |
| Neisseria | |
| *Neisseria meningitidis* | |
| *Neisseria gonorrhea* | |
| Enterobacteriaceae | |
| *Escherichia coli* | |
| *Aerobacteria aerogenes* | |
| *Klebsiella pneumoniae* | The coliform bacteria |
| *Salmonella typhosa* | |
| *Salmonella choleraesuis* | The Salmonellae |
| *Salmonella typhimurium* | |
| *Shigellae dysenteriae* | |
| *Shigellae schmitzii* | |
| *Shigellae arabinotarda* | |
| *Shigellae flexneri* | The Shigellae |
| *Shigellae boydii* | |
| *Shigellae sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |
| Hemophilus-Bordetella group | |
| *Hemophilus influenza, H. ducryi* | |
| *Hemophilus hemophilus* | |
| *Hemophilus aegypticus* | |
| *Hemophilus parainfluenzae* | |
| *Bordetella pertussis* | |
| Pasteurellae | |
| *Pasteurella pestis* | |
| *Pasteurella tulareusis* | |
| Brucellae | |
| *Brucella melitensis* | |
| *Brucella abortus* | |
| *Brucella suis* | |
| Aerobic Spore-Forming Bacilli | |
| *Bacillus anthracis* | |
| *Bacillus subtilis* | |
| *Bacillus megaterium* | |
| *Bacillus cereus* | |
| Anaerobic Spore-Forming Bacilli | |
| *Clostridium botulinum* | |
| *Clostridium tetani* | |
| *Clostridium perfringens* | |
| *Clostridium novyi* | |
| *Clostridium septicum* | |
| *Clostridium histolyticum* | |
| *Clostridium tertium* | |

*Clostridium bifermentans*
*Clostridium sporogenes*
Mycobacteria

*Mycobacterium tuberculosis hominis*
*Mycobacterium bovis*
*Mycobacterium avium*
*Mycobacterium leprae*
*Mycobacterium paratuberculosis*
Actinomycetes (fungus-like bacteria)

*Actinomyces isaeli*
*Actinomyces bovis*
*Actinomyces naeslundii*
*Nocardia asteroides*
*Nocardia brasiliensis*
The Spirochetes

*Treponema pallidum*
*Treponema pertenue*
*Treponema carateum*
*Spirillum minus*
*Streptobacillus moniliformis*
*Borrelia recurrens*
*Leptospira icterohemorrhagiae*
*Leptospira canicola*
Trypanasomes Mycoplasmas

*Mycoplasma pneumoniae*
Other pathogens

*Listeria monocytogenes*
*Erysipelothrix rhusiopathiae*
*Streptobacillus moniliformis*
*Donvania granulomatis*
*Bartonella bacillformis*
Rickettsiae (bacteria-like parasites)

*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Rickettsia burnetti*
*Rickettsia quintana*
Chlamydia (unclassifiable parasites bacterial/viral)

Chlamydia agents (naming uncertain)
Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifera* (*Absidia corymbifera*)
*Rhizopus oryzae*
*Rhizopus arrhizus*      Phycomycetes
*Rhizopus nigricans*
*Sporotrichum schenkii*
*Flonsecaea pedrosoi*
*Fonsecaea compact*
*Fonsecacae dermatidis*
*Cladosporium carrioni*
*Phialophora verrucosa*
*Aspergillus nidulans*
*Madurella mycetomi*
*Madurella grisea*
*Allescheria boydii*
*Phialophora jeanselmei*
*Microsporum gypsum*
*Trichophyton mentagrophytes*
*Keratinomyces ajelloi*
*Microsporum canis*
*Trichophyton rubrum*
*Microsporum adouini*
Viruses Adenoviruses
Herpes Viruses

*Herpes simplex*
*Varicella* (Chicken pox)
*Herpes zoster* (Shingles)
Virus B
Cytomegalovirus
Pox Viruses Variola (smallpox)
Vaccinia
*Poxvirus bovis*
Paravaccinia
*Molluscum contagiosum*
Picornaviruses Poliovirus
Coxsackievirus
Echoviruses
Rhinoviruses
Myxoviruses Influenza (A, B, and C)
Parainfluenza (1–4)
Mumps virus
Newcastle disease virus
Measles virus
Rinderpest virus
Canine distemper virus
Respiratory syncytial virus
Rubella virus
Arboviruses Eastern equine encephalitis virus
Western equine encephalitis virus
Sindbis virus
Chikugunya virus
Semliki forest virus
Mayora virus
St. Louis encephalitis virus
California encephalitis virus
Colorado tick fever virus
Yellow fever virus
Dengue virus
Reoviruses Reovirus types 1–3
Retroviruses Human immunodeficiency viruses (HIV)
Human T-cell lymphotrophic virus I & II (HTLV)
Hepatitis Hepatitis A virns
Hepatitis B virus
Hepatitis nonA-nonB virus
Hepatitis, C, D, E
Tumor viruses Rauscher leukemia virus
Gross virus
Maloney leukemia virus
Human papilloma viruses It would be understood by one of skill in the art that it is generally required to treat samples suspected of containing a particular TNA in such a fashion as to produce fragments that can easily hybridize with the PNA. It may be necessary to treat the test sample to effect release of or to extract the TNA for hybridization, such as by exposing blood or other cells to a hypotonic environment, or otherwise disrupting the sample using more vigorous means. When the TNA is thought to be present in double stranded form, it would naturally be desirable to separate the strands to render the TNA hybridizable in single stranded form by methods well known in the art, including but not limited to heating or limited exposure to alkaline conditions which may be neutralized upon addition of the single stranded PNA to allow hybridization to occur.

Fragmentation of nucleic acid samples containing TNAs is usually required to decrease the sample viscosity and to increase the accessibility of the TNAs to the PNAs. Such fragmentation is accomplished by random or specific means known in the art. Thus, for example, specific nucleases known to cut with a particular frequency in the particular genome being analyzed, may be used to produce fragments of a known average molecular size. In addition, other nucleases, phosphodiesterases, exonucleases and endonucleases, physical shear and sonication are all methods amenable for this purpose. These processes are well known in the art. The use of restriction enzymes for the purpose of DNA fragmentation is generally preferred. However, DNA can also be fragmented by a variety of chemical means such as the use of the following types of reagents: EDTA-Fe(II) (according to Stroebel et al. [1988] *J. Am. Chem. Soc.* 110:7927; Dervan [1986] *Science* 232:464); Cu(II)-phenanthroline (according to Chen and Sigman [1987] *Science* 237:1197); class IIS restriction enzyme (according to Kim et al. [1988] *Science* 240:504); hybrid DNAse (according to Corey et al. [1989] *Biochem.* 28:8277); bleomycin (according to Umezawa et al. [1986] *J. Antibiot.* (Tokyo) Ser. A, 19:200); neocarzinostatin (Goldberg et al. [1981] *Second Annual Bristol-Myers Symposium in Cancer Research,* Academic Press, New York, p.163); and methidiumpropyl-EDTA-Fe(II) (according to Hertzberg et al. [1982] *J. Am. Chem. Soc.* 104:313). Removal of proteins, as by treatment with a protease, is also generally desirable and methods for effecting protein removal from nucleic acid samples, without appreciable loss of nucleic acid, are well known in the art.

The TNAs of the present invention should be long enough so that there is a sufficient amount of double-stranded hybrid flanking the TBR so that a TBA can bind unperturbed by the unligated fragment ends. Typically, fragments in the range of about 10 nucleotides to about 100,000 nucleotides, and preferably in the range of about 20 nucleotides to about 1,000 nucleotides are used as the average size for TNA fragments. Examples of specific TNA sequences that could be detected are sequences complementary to the PNA sequences described herein for detection of normal cellular, abnormal cellular (as in activated oncogenes, integrated foreign genes, genetically defective genes), and pathogen-specific nucleic acid sequences, for which specific DNA binding proteins are known, or which can be produced according to methods described in this disclosure. With reference to FIG. 7, a specific HIV-related TNA is shown as SEQ ID NO. 37.

4. Extensions to the PNA using BNAs, their preparation, and signal amplification. Under hybridizing conditions, BNAs can be added that hybridize to the PNAs, PNA-BNA hybrids, BNAs and/or BNA-BNA hybrids. The aforementioned additions can be made in a non-vectorial polymeric fashion or in a vectorial fashion, with a known order of BNAs.

With reference to FIGS. 2A–B, a simple booster is presented. A booster polymer is produced by adding two BNAs, illustrated in FIGS. 2A–B(Ib and Ic), which when combined under hybridizing conditions with the PNA, form PNA-BNA-BNA hybrids, comprised of the PNA and "booster" extensions", illustrated in FIGS. 2A–B(IIa,IIb,IIc and IId) leaving at least one unpaired ½ BBR sequence. Each unpaired ½ BBR sequence, illustrated in FIGS. 2A–B (IIa, IIb, IIc, IId) can hybridize with additional BNAs to form additional "booster" extensions. Each unpaired ½ BBR sequence, illustrated in FIGS. 2A–B(IIa,IIb,IIc and IId) can hybridize with added HNAs, illustrated in FIGS. 2A–B(IIIa and IIIb). The hybridization of the HNAs, which cannot hybridize additional BNAs, acts to "cap" the addition of the BNAs onto the PNA, as illustrated in FIGS. 2A–B(IVa, IVb, IVc and IVd).

With reference to FIGS. 2C–D, it is possible to control and specify the order and components of extensions to the PNA. If a single BBR is required, a HNA containing the complementary sequence to the ½ BBR in the PNA is added to the PNA to produce a single BBR and to "cap" any "booster" extensions to the PNA. If additional BBRs are to be added to the PNA, a controlled extension of the PNA can be accomplished.

With reference to FIGS. 2C–D, a simple booster is presented. Vectorial polymer extension is accomplished by adding a BNA which is specific for the PNA, as illustrated in FIGS. 2C–D(Ia and IIa), which when combined under hybridizing conditions with the PNA, form PNA-BNA-BNA hybrids, comprised of the PNA and "booster" extensions. These extensions, if labeled with an OSA, provide a method for greatly amplifying any signal produced upon binding of a PNA to a TNA in the sample. Furthermore, by binding labeled BBAs to the BBRs in the polymer, additional amplification is achieved.

Any of a number of methods may be used to prepare the BNAs, including, e.g., synthesis via known chemistry or via recombinant DNA production methods. In the latter method, an essentially unlimited number of BNAs may be produced simply and inexpensively, for example, by production in prokaryotes (*E. coli* for example) of a plasmid DNA having multiple repeats of the specific BNA sequences flanked by restriction sites having overhanging ends. In this fashion, for example, the bacteriophage lambda left or right operator sites, or any other DNA sequence known to specifically and tightly bind a particular BBA, such as a DNA binding protein, may be produced in an essentially unlimited number of copies, with each copy flanked by an EcoRI, PstI, BamHI or any of a number of other common restriction nuclease sites. Alternatively, a polymer at repeated sites may be excised by unique restriction sites not present within the polymer. Large quantities of pBR322, pUC plasmid or other plasmid having multiple copies of these sequences are produced by methods well known in the art, the plasmid cut with the restriction enzyme flanking the polymerized site, and the liberated multiple copies of the operators isolated either by chromatography or any other convenient means known in the art. The BNA, prior to use, is then strand separated and is then amenable for polymerization onto a PNA encoding a single stranded complementary copy of the operator as a ½ BBR. The BNAs may be polymerized vectorially onto the PNA by using different restriction enzymes to flank each repeat of the polymer in the plasmid used to produce multiple copies of the BNA. Alternatively, the BNA polymer may be hybridized to the PNA via overhangs at one or both ends of the BNA polymer, without the need to strand separate and anneal each BNA segment. Examples of specific BNA sequences are provided above in the section entitled Description of Sequences, as SEQ ID NOS. 35–36. To stabilize the BNA polymer, DNA ligase may be used to covalently link the hybridized BNAs.

5. The Hairpin Nucleic Acids (HNAs) and their preparation. The HNAs of the present invention comprise at least two principal parts joined together: A single-stranded sequence, which is complementary to a ½ BBR, and a double-stranded nucleic acid region formed, under hybridizing conditions, by the self-association of self-complementary sequences within the HNA. With reference to FIG. 1(IIc) of the drawings, the ½ BBR in the HNA may be constructed so as to be complementary to the ½ BBR sequence in the PNA. With reference to FIG. 1(I, IIc and IIIc) of the drawings, the aforementioned HNA, when added to the PNA under hybridizing conditions, forms a PNA-HNA hybrid containing a BBR. With reference to FIG. 1(IIIc, IVc and Vc) of the drawings, a PNA-HNA hybrid, under hybridizing conditions, upon addition of the TNA, can form a TNA-PNA-HNA hybrid containing a TBR and a BBR.

With reference to FIGS. 2A–D, the HNAs can be used to "cap" or terminate the addition of BNA extensions to the PNA. The two BNAs in FIGS. 2A–B(Ib and Ic) can associate to form the hybrid shown in FIG. 3(IVb) or can hybridize directly and individually to the PNA as illustrated in FIGS. 2A–B(Ia–c, IIa–d). The two HNAs (shown in FIGS. 2A–B(IIIa and IIIb)) can terminate the hybridization of the BNA to other BNAs which extend from the PNA, as illustrated in FIG. 2a (IVa–d). The HNA in FIGS. 2A–B (IIIa) can terminate the PNA-BNA hybrids shown in FIGS. 2A–B(IIb and IId) and any PNA-BNA hybrid with a single stranded ½ BBR which is complementary to the ½ BBR in the HNA illustrated in FIG. 2a(IIIa). Similarly, the HNA in FIGS. 2A–B(IIIb) can terminate the PNA-BNA hybrids shown in FIGS. 2A–B(IIa and IIc) and any PNA-BNA hybrid with two single stranded ½ BBRs which are complementary to the ½ BBRs in the HNA illustrated in FIGS. 2A–B(IIIb).

HNAs are constructed that will terminate PNA-BNA hybrids which are constructed from the sequential addition of BNAs to the PNA as illustrated in FIGS. 2C–D. The single stranded ½ BBR sequences illustrated in FIG. 2b(Ia, IIIa, Va, and VIIa) are specifically complementary to the single stranded ½ BBR sequences illustrated in FIG. 2b(Ib, IIIb,Vb and VIIb) and produce the unique capped PNA-BNA-HNA hybrids illustrated in FIG. 2b(Ic,IIIc, Vc and VIIc).

The self-complementary sequences in the HNA and the loop sequence which links the self-complementary hairpin sequences can be of any composition and length, as long as they do not substantially impede or inhibit the presentation of the single-stranded ½ BBR that comprises part of the HNA by the HNA or selectively bind the BBA or the TBA. The loop sequences should be selected so that formation of the loop does not impede formation of the hairpin. An examples of an HNA useful in this application is provided as SEQ ID NO. 44 (see Description of Sequences above).

6. The Target Binding Assemblies (TBAs) and their preparation. A TBA may be any substance which binds a particular TBR formed by hybridization of particular TNAs and PNAs, provided that the TBA must have at least the following attributes:

(a) The TBA must bind the TBR(s) in a fashion that is highly specific to the TBR(s) of interest. That is, the TBA must discriminate between TBRs present in the TNA-PNA hybrid and similar duplex sequences formed by PNA-CNA hybrids. The TBA must bind the PNA-CNA hybrid with a sufficiently low avidity that upon washing the TBA-TNA-PNA complex, the hybrid is displaced;

(b) The TBA must avidly bind the TBR(s) created by the hybridization of the TNA with the PNA Binding affinities in the range of $10^{-5}$ to about $10^{-12}$ or higher are generally considered sufficient. As noted below, in some instances, it might be desirable to utilize a particular TBA which has a very low avidity for a particular TBR, but which has a greatly increased affinity when a particular configuration of multiple TBRs is provided so that the square of the affinity of the TBA for each TBR becomes the affinity of relevance to that particular TBA.

Examples of the DNA binding components useful in the formation of TBAs include, but are not limited to NF-kB, papillomavirus E2 protein, transcription factor SP1, inactive restriction enzymes, etc. Each of these proteins has been recognized in the art to contain sequences which bind to particular nucleic acid sequences and the affinities of these interactions are known. Naturally, the method of the instant invention is not limited to the use of these known DNA binding proteins of fragments thereof. From the instant disclosure, it would be apparent to one of ordinary skill that the instant method could easily be applied to the use of novel TBAs exhibiting at least the required attributes noted above. Thus, for example, in WO 92/20698, a sequence specific DNA binding molecule comprising an oligonucleotide conjugate formed by the covalent attachment of a DNA binding drug to a triplex forming oligonucleotide was described. The method of that disclosure could be used to produce novel TBAs for use according to the instant disclosure, provided that the TBAs thus formed meet the criteria described above. In addition, the methods of U.S. Pat. Nos. 5,096,815, 5,198,346, and WO88/06601, herein incorporated by reference, may be used to generate novel TBAs for use according to the method of this invention.

Where the TBA is a protein, or a complex of proteins, it will be recognized that any of a number of methods routine in the art may be used to produce the TBA. The TBA may be isolated from its naturally occurring environment in nature, or if this is impractical, produced by the standard techniques of molecular biology. Thus, using NF-kB as an example, using the DNA binding portions of p50 or p65 subunits, this binding assembly could be produced according to recombinant methods known in the art (see for example Ghosh [1990] *Cell* 62:1019–1029, describing the cloning of the p50 DNA binding subunit of NF-kB and the homology of that protein to rel and dorsal).

Many DNA binding proteins are known which can be used as or in TBAs according to this invention. Once the amino acid sequence of any DNA binding protein is known, an appropriate DNA sequence encoding the protein can either be prepared by synthetic means, or a cDNA copy of the mRNA encoding the protein from an appropriate tissue source can be used. Furthermore, genomic copies encoding the protein may be obtained and introns spliced out according to methods known in the art. Furthermore, the TBAs may be chemically synthesized.

Once an appropriate coding sequence has been obtained, site-directed mutagenesis may be used to alter the amino acid sequence encoded to produce mutant DNA binding proteins exhibiting more desirable binding characteristics than those of the original DNA binding protein. As an example of this process, the amino acid sequence of the DNA binding portions of NF-kB can be altered so as to produce an NF-kB' molecule which more tightly binds the NF-kB binding site (see examples below—HIV-Detect and HIV-Lock).

To provide further insight into this aspect of the invention, the following considerations are to be noted. Using NF-kB as an example, a TBA may be prepared using the naturally occurring NF-kB molecule. However, because this molecule is present in vanishingly small quantities in cells, and because the subunits of this DNA binding protein have been cloned, it would be more reasonable to prepare large quantities of the complex via recombinant DNA means as has already been accomplished for this protein (see for example Ghosh [1990] Cell 62:1019–1029).

NF-kB is a pleiotropic inducer of genes involved in immune, inflammatory and growth regulatory responses to primary pathogenic (viral, bacterial or stress) challenges or secondary pathogenic (inflammatory cytokine) challenges. NF-kB is a dimeric DNA binding protein comprising a p50 and a p65 subunit, both of which contact and bind to specific DNA sequences. In an inactivated state, NF-kB resides in the cellular cytoplasm, complexed with a specific inhibitor, I-kB, to form a cytoplasmic heterotrimer. Upon activation, the inhibitor is decomplexed, and the p50-p65 dimer relocates via a specific nuclear localization signal (NLS) to the cell's nucleus where it can bind DNA and effect its role as a transcriptional activator of numerous genes (see Grimm and Baeuerle [1993] Biochem. J. 290:297–308, for a review of the state of the art regarding NF-kB).

The p50-p65 dimer binds with picomolar affinity to sequences matching the consensus GGGAMTNYCC (SEQ ID NO. 117), with slightly different affinities depending on the exact sequence. It is worth noting that homodimers of p50 and p65 have also been observed to occur. These homodimers display different biochemical properties as well as slightly different affinities of binding sequences within and similar to the above consensus. Thus, depending on the desired binding characteristics of the TBA, a p50-p65 heterodimer, a p50-p50 homodimer, or a p65-p65 homodimer or fragments of the aforementioned dimers may be used.

One way in which various novel TBAs may be produced for use according to this invention is shown schematically in FIG. 9. The DNA recognition units of the TBA may be assembled and associated with similar or dissimilar TBA DNA recognition units via a "chaperone." The chaperone is a structure on which the various TBA recognition elements are built and which confers desirable properties on the DNA recognition units. The chaperone is comprised of any sequence which provides assembly sequences such that same or different DNA recognition units are brought into close and stable association with each other. Thus, for example, in the case of a TBA designed to tightly bind NF-kB TBRs, a TBA is assembled by providing lambda cro sequences as assembly sequences, linked to the DNA binding sequences for either NF-kB p50 or p65. The p50 or p65 DNA binding sequences are linked to the cro sequences at either the carboxy or amino terminus of cro and either the carboxy or amino terminus of the DNA recognition unit of the p50 or p65. Linking sequences are optionally provided to allow appropriate spacing of the DNA recognition units for optimal TBR binding.

The assembly sequences, exemplified above by cro and CI sequences (SEQ ID NOS. 104–108), comprise any stable oligopeptides which naturally and strongly bond to like sequences. Thus, in the case of cro, it is well known that a dimer of cro binds to the bacteriophage lambda operator sites (Anderson et al. [1981] Nature 290:754–758; Harrison and Aggarwal [1990] Ann. Rev. Biochem. 59:933–969). The monomer units of cro tightly and specifically associate with each other. Thus, by linking DNA recognition unit sequences to the cro sequences, close and tight association is achieved.

The optional linker sequences comprise any amino acid sequence which does not interfere with TBA assembly or DNA binding, and which is not labile so as to liberate the DNA recognition unit from the complete TBA. It is desirable but not necessary that the linker sequences be covalently linked to other binding assembly components. The association should be specific so as to aid in the assembly and manufacture of the binding assemblies. Examples of such sequences include, but are not limited to, such well known sequences as are found linking various domains in structural proteins. Thus, for example, in the lambda repressor protein, there is a linking sequence between the DNA binding domain and the dimerization domain which is useful for this purpose. Many other such sequences are known and the precise sequence thereof is not critical to this invention, provided that routine experimentation is conducted to ensure stability and non-interference with target nucleic acid binding. Examples of such sequences are provided herein as Met Ser and SEQ IN NOS. 99–102. Insertion of specific, known proteolysis sites into these linkers is also an integral part of this invention. The presence of such sites in the linker sequences would provide manufacturing advantages, allowing different molecules to be assembled on the chaperone scaffold.

In addition to the DNA recognition units, optional linking sequences, and assembly sequences, the novel TBAs of this invention optionally have asymmetry or PILOT TNA sequences and one or more OSA units. The asymmetry sequences are provided to encourage or prevent certain desirable or undesirable associations. For example, in the event that a TBA having homodimeric p50 DNA recognition units is desired, the asymmetry sequences are provided to disrupt the naturally stronger association of NF-kB 50 subunits and p65 subunits, while not disrupting the assembly sequences from bringing together p50 subunits. Examples of such sequences are provided herein as SEQ ID NOS. 85–92 and SEQ ID NOS. 105 and 106.

In a different configuration, NF-kB p50 subunit sequences are brought into close association with transcription factor SP1 DNA recognition unit sequences. This is desirable in the event that an NF-kB/SP1 binding motif is of significance, as in the HIV LTR where a motif of at least six DNA binding protein recognition sites, two NF-kB, three SP1, and a TATA site are known to exist. Since it is also known that the second NF-kB and first SP1 site are significant to regulation of HIV transcription (Perkins et al. [1993] Embo J. 12:3551–3558), this particular configuration of TBA is useful not only in the detection of HIV, but as a therapeutic or prophylactic against HIV infection (see below). In a similar fashion, the long control region (LCR) of human papillomavirus may be used as a key control region for probing according to this method.

In view of the different elements that can be associated, cassette fashion, according to this method of TBA formation, an essentially unlimited variety of TBAs are produced. In FIG. 10, a series of different molecules, referred to as "HIV-detect I–IV" are exemplified wherein "CHAP" denotes the chaperone, "nfkb" denotes NF-kB subunits, "sp1" denotes the DNA recognition unit of the SP1 transcription factor, and "TATA" denotes a dimer of the DNA recognition unit of a TATA sequence DNA binding protein (TBP), also known as a TATA binding protein, or TBP. These configurations are further exemplified below and are all integral parts of the instant invention.

In yet another configuration, the modular structure shown in FIG. 9 is adapted to detection and or treatment or prophylaxis of a completely different pathogen. In FIG. 11, in a similar fashion to the above described "HIV-detect I–IV" molecules, a series of "HPV-Detect I–IV" molecules is produced. In this embodiment, advantage is taken of the DNA binding properties of the E2 protein of human papillomavirus (HPV). In addition, the roles of SP1 and TBP is taken advantage of by providing specific DNA recognition units adapted to bind to these sequences in the HPV genome. In the formation of the E2-specific TBAs for use in detecting HPV infection, it may be desirable to use any of SEQ ID NOS. 75–84 or 93–98 as the E2 DNA recognition units. A TBA containing a bovine E2 dimer and a human E2 dimer DNA binding domain may be particularly useful.

The various sequences described above may either be chemically linked using pure oligopeptide starting materials, or they may be linked through provision of recombinant nucleic acids encoding via the well known genetic code the various subelements. In the event of recombinant production, linking cro coding sequences to sequences of DNA recognition units to form TBAs is advantageous because not only does cro act as assembly sequences in the chaperone, it also acts to direct the proper folding of the DNA recognition elements. Exemplary sequences for chaperones are provided herein as SEQ ID NOS. 104–108. Furthermore, in the event that higher order structures comprising multiple binding sites is desired, as in a pentameric NF-kB/NF-kB/SP1/SP1/SP1 TBA, proper design of the asymmetry sequences allows such structures to be made.

In the foregoing fashion, TBAs are prepared which bind to their cognate binding sites with high affinity. For example, the NF-kB DNA binding components of the TBAs of FIG. 10 are expected to bind to the HIV-LTR with an affinity of between about $10^{-8}$ and $10^{-12}$ molar. Sequences useful as the DNA recognition units are provided as SEQ ID NOS. 63–71, 73–84, 93–98, and 104–108 and exemplified further below.

In view of the foregoing description of directed assembly at nucleic acid binding proteins using assembly and asymmetry (or piloting) sequences, those skilled in the art will recognize that a generally applicable method for assembling protein structures is provided by this invention. The generality of this method is demonstrated further by consideration, by way of further example, of the use of an antibody-epitope interaction in the assembly of desired structures. By way of specificity, a DNA binding protein structure may be assembled by linking an NF-kB p50 subunit to an antigen, such as a circularized (through disulfide bonds) melanocyte stimulating hormone (MSH). This pro-MSH molecule may then be bound by an anti-MSH antibody to provide a novel nucleic acid binding assembly, with the antigen and antibody acting as assembly sequences.

The modular structure provided by FIG. 9 reveals that a great variety of TBAs may be assembled using different combinations of components. Thus, representative embodiments of this general structure are provided as SEQ ID NOS. 109–116.

7. The Booster Binding Assemblies (BBAs) and their preparation. A BBA may be any substance which binds a particular BBR formed by hybridization of particular PNAs and BNAs, including when multiple BNAs (up to and including "n" BNAs, ie., $BNA_n$, wherein "n" is theoretically 0-∞, but practically is between about 0 and 100) are polymerized onto the PNA for signal amplification, provided that the BBA must have at least the following attributes:

(a) The BBA must bind the BBRs in a fashion that is highly specific to the BBR of interest. That is, the BBA must discriminate between BBRs present in the PNA-BNA hybrid and similar duplex sequences in CNAs. Thus, where even a single base mismatch occurs in the production of the PNA-$BNA_n$ or PNA-$BNA_n$-HNA hybrid, the BBA must bind the hybrid with a sufficiently low avidity that upon washing the TBA-TNA-PNA-$BNA_n$ complex, the BBA is displaced.

(b) The BBA must avidly bind the BBR(s). Binding affinities in the range of $10^{-5}$ to about $10^{-9}$ or higher are generally considered sufficient.

Examples of BBAs include, but are not limited to cro, and the bacteriophage lambda repressor protein, CI. In addition, see U.S. Pat. No. 4,556,643, herein incorporated by reference, which suggests other DNA sequences and specific binding proteins such as repressors, histones, DNA modifying enzymes, and catabolite gene activator protein. See also EP 0 453 301, herein incorporated by reference, which suggests a multitude of nucleotide sequence specific binding proteins (NSSBPs) such as the tetracycline repressor, the lac repressor, and the tryptophan repressor. Each of these BBAs has been recognized in the art to bind to particular, known nucleic acid sequences and the affinities of these interactions are known. Naturally, the method of the instant invention is not limited to the use of these known BBAs. From the instant disclosure, one of ordinary skill could easily apply the use of novel BBAs exhibiting at least the required attributes noted above to the instant method.

Examples of novel BBAs useful according to this aspect of the invention include novel proteins based on the motif of a known DNA binding protein such as cro or the λ CI repressor protein. Preferably, such modifications are made to improve the handling of these components of the invention. Thus, it may be desirable to add a high concentration of cro to an assay. One of the negative qualities of cro is that at high concentrations, the binding of cro to its DNA target comes into competition with cro-cro interactions. Thus, for example, a chaperoned or mutated cro may be produced which does not have this shortcoming. Examples of such altered chaperones are SEQ ID NOS. 105–106 and 108. Methods known in the art, such as production of novel target binding proteins using variegated populations of nucleic acids and selection of bacteriophage binding to particular, pre-selected targets (i.e., so-called phage-display technology, see discussion above for production of novel TBAs) may be used to produce such novel BBAs as well as the aforementioned novel TBAs.

Where the BBA is a protein, or a complex of proteins, it will be recognized that any of a number of methods routine in the art may be used to produce the BBA. The BBA may be isolated from its naturally occurring environment in nature, or if this is impractical, produced by the standard techniques of molecular biology. Thus, for example, the sequence of the cro protein is known and any molecular clone of bacteriophage lambda may be used to obtain appropriate nucleic acids encoding cro for recombinant production thereof. In addition, the TBAs described herein may be used as BBAs, provided that different TBAs are used to bind TBRs and BBRs.

8. The use of BBAs and BBRs to localize and amplify the localization of the PNA-TNA-TBA complexes (see FIGS. 8A–B). In one embodiment of this invention, the highly specific and extremely tight binding of DNA binding proteins is used to produce an amplifiable nucleic acid sandwich assay. According to one aspect of this embodiment, a solid support is coated with a first TBA creating an immobilized TBA. In solution, a PNA and TNA are contacted under hybridizing conditions and then contacted with the immobilized TBA Only those PNA-TNA interactions which form the specific TBR recognized by the immobilized TBA are retained upon wash-out of the solid surface which binds the TBA-TBR complex.

Detection of the bound TBR is accomplished through binding of Booster Nucleic Acids, BNAs, to the ½ BBRs present on the PNAs under hybridizing conditions. In this manner, even if only a single TBA-TBR complex is bound to the immobilized TBA, a large, amplified signal may be produced by polymerizing multiple BNAs to the immobilized TNA. Each BNA which binds to the TNA forms a BBR which can be bound by BBAs which, like the TBAs immobilized on the solid surface, may be chosen for their very tight and specific binding to particular duplex DNA structures. Thus, according to this embodiment, the immobilized TBA may contain the DNA binding portion of NF-kB, which very specifically and tightly binds to NF-kB binding sites formed upon hybridization of the TNA and PNA to form such a site.

Because it is well known that there are NF-kB binding sites both in the normal human genome and in the long terminal repeats of human immunodeficiency virus (HIV), this invention provides a method of discriminating between the "normal" human sites and the sites present in cells due to HIV infection. Therefore, in a test designed to determine the presence or absence of HIV DNA in a sample of human DNA, the HIV NF-kB binding sites may be viewed as the TNA, and the normal human NF-kB binding sites may be viewed as CNAs. According to the method of this invention, discrimination between these TNAs and CNAs is accomplished by taking advantage of the fact that in the HIV LTR, there are two NF-kB binding sites, followed by three SPI sites (see, for example, Koken et al. [1992] *Virology* 191:968–972), while cellular NF-kB binding sites with the same sequences are not found in tandem.

In cases where the TNA contains more than one ½ TBR and it is desirable to pursue the therapeutic and prophylactic applications of the TBAs, it may be desirable to use more than one TBA, each with the capacity to bind a TBR in the TNA-PNA complex. In this case, it may be advantageous to select, as components of the TBAs, DNA-binding domains with lesser affinity for its TBR than the wild-type DNA-binding domain. Given that the TBAs which are involved in the binding to the multiple TBRs can either assemble together before binding to their TBRs or assemble together after binding to their TBRs, the individual TBAs will not block the corresponding TBRs in the other genomes than the target genome unless the TBRs are spatially capable of binding the assembled TBA complex. One feature of the multimeric assembly of TBAs which is specifically claimed here as part of this invention is that such a multimeric assembly is expected to have a much reduced affinity for a single site within the TNA. However, since the binding is dramatically increased relative to any one TBA, the TBA complex would be expected to not compete for the binding of any single TBR with the corresponding native proteins in situ but bind tightly to sequences in the PNA-TNA hybrid containing the TBRs for each of the DNA-binding components assembled in the TBA. The TBA complex should be assembled and linkers adjusted in the individual TBAs so as to allow the DNA-binding regions contained in the TBA complex to simultaneously reach and bind to these targets.

Once the TNA-PNA hybrids have formed and been contacted with the immobilized TBA, unbound nucleic acid is washed from the immobilized surface and the immobilized hybrids detected. This is accomplished in any one of several ways. In one aspect of this invention, the PNA is labeled with an OSA, such as a radionuclide, colored beads, or an enzyme capable of forming a colored reaction product. Furthermore, in addition to having one or more ½ TBRs, the PNA also may contain at least one ½ BBR. The ½ BBR sequences are chosen so as to be complementary to unique ½ BBR sequences in BNAs. In the embodiment described above, for example, where the TBA is NF-kB and the TBR formed upon TNA-PNA hybridization is one or more NF-kB binding sites, the ½ BBRs may provide hybridizable (that is, single-stranded, complementary) sequences of the left or right bacteriophage lambda operators (see, for example, Ptashne [1982] *Scientific American* 247:128–140, and references cited therein for sequences of these operators). These may be polymerized onto the PNA ½ BBRs in a vectorial fashion (see FIGS. 2 and 3) providing up to "n" BBRs, and each BBR forms a cro binding site. Enzymatically, radioactively, or otherwise labeled cro, is contacted with the TBA-TNA-PNA-(BNA)$_n$ complex. In this fashion, a highly selective and amplified signal is produced. Signal produced using a PNA having a single ½ TBR indicates success of the assay in achieving TBA-TBR binding and polymerization of the BNAs to produce signal from cellular sites (i.e. from CNAs). Absence of signal when a dimerized TBA is used indicates that in the TNA, there were no HIV LTRs as no double NF-kB binding sites were present. On the other hand, presence of signal using the dimer NF-kB indicates HIV infection. As a specific example of the foregoing description of this embodiment of the invention, see Example 6 describing an HIV test kit.

Naturally, those skilled in the art will recognize that the foregoing description is subject to several modifications in the choice of PNAs, TNAs, TBAs, BNAs, and BBAs. Furthermore, in systems other than HIV, those skilled in the art will recognize that the general method described above could be likewise applied. However, these other applications may be simpler than the above described method as the TBAs used may not recognize any normal cellular sites and therefore resort to dimerization or other methods of discriminating between TNAs and CNAs may be less critical. In designing probes and binding assemblies for these other systems, the skilled artisan will be guided by the following principles and considerations.

In the above-described embodiment, the appeal of using the DNA-binding portions of NF-kB protein as the TBA and the NF-kB recognition binding elements as the TBRs is that these elements form an important "control point" for the replication of HIV. That is, it is known that HIV is required to use NF-kB as a critical feature in its replicative life cycle. Similar control points for other pathogens are chosen and used as a basis for detection according to the methods described herein.

From the foregoing description of general features of this invention and the mode of its operation, one skilled in the art will recognize that there are a multiplicity of specific modes for practicing this invention. By way of example, the method of this invention is adaptable to a method and devices using chromatographic test kits described in U.S. Pat. Nos. 4,690, 691 and 5,310,650 (the '691 and '650 patents). In those patents, a porous medium was used to immobilize either a TNA or a capture probe, and a solvent was used to transport a mobile phase containing either a labeled PNA, if the TNA was immobilized, or the TNA, if a capture probe was immobilized, into the "capture zone." Once the TNA was bound in the capture zone, either by directly immobilizing it or through capture, a labeled PNA was chromatographed through the capture zone and any bound label was detected.

Adapting the instant invention to such a system provides the improvement of using a Target Binding Assembly in the capture zone and therefore, the capture of only perfectly matched TBR sequences within the TNA-PNA duplexes by virtue of the previously described sensitive discrimination by the TBA between TNAs and CNAs.

Once the TNA-PNA hybrids become bound to the immobilized TBA, the signal is amplified by adding BNAs or chromatographing BNAs through the capture zone. Finally, the signal may be further amplified by adding BBAs or chromatographing labeled BBAs through the capture zone. In this fashion, the ease of performing the analysis steps described in the '691 and '650 patents is improved upon herein by providing the additional ability to increase the specificity and, through amplification, the sensitivity of the method described in those patents. The disclosure of the '691 and '650 patents is herein incorporated by reference for the purpose of showing the details of that method and for the teachings provided therein of specific operating conditions to which the compositions and methods of the instant invention are adaptable.

Those skilled in the art will also recognize that the method of the instant invention is amenable to being run in microtiter plates or to automation. The use of machines incorporating the method of this invention therefore naturally falls within the scope of the instant disclosure and the claims appended hereto. Thus, for example, this invention is adaptable for use in such instruments as Abbott Laboratories' (Abbott Park, Ill.) IMx tabletop analyzer. The IMx is currently designed to run both fluorescent polarization immunoassay (FPZA, see Kier [1983] *KCLA* 3:13–15) and microparticle enzyme immunoassay (MEZA, see *Laboratory Medicine*, Vol. 20, No. 1, January 1989, pp. 47–49). The MEZA method is easily transformed into a nucleic acid detection method using the instant invention by using a TBA as a capture molecule coated onto a submicron (<0.5 $\mu$m on average) sized microparticle suspended in solution. The microparticles coated with TBA are pipetted into a reaction cell. The IMx then pipettes sample (hybridized PNA-TNA) into the reaction cell, forming a complex with the TBA. After an appropriate incubation period, the solution is transferred to an inert glass fiber matrix for which the particles have a strong affinity and to which the microparticles adhere. Either prior to or after filtering the reaction mixture through the glass fiber matrix, BNAs and BBAs are added, or another signal amplification and detection means is used which depends on specific formation of TNA-PNA hybrids. The immobilized complex is washed and the unbound material flows through the glass fiber matrix.

The bound complexes are detected by means of alkaline phosphatase labeled BBAs or otherwise (radioactively, enzymatically, fluorescently) labeled BBAs. In the case of alkaline phosphatase labeled BBAs, the fluorescent substrate 4-methyl umbelliferyl phosphate may be added. Alternatively, the enzyme may be bypassed by directly labeling BBAs with this or a like reagent. In any event, fluorescence or other signal is proportional to the amount of PNA-TNA hybrids present.

The fluorescence is detected on the surface of the matrix by means of a front surface fluorometer as described by the manufacturer of the IMx. With minor adjustments that can be made through routine experimentation to optimize an instrument such as the IMx for nucleic acid hybridization and DNA-DNA binding protein interactions, the instant invention is completely adaptable to automated analyses of TNA samples.

9. Other diagnostic applications of this invention. While the foregoing description enables the use of the instant invention in a number of different modes, many additional utilities of this invention are readily appreciated, for example, in a mobility retardation system.

In this embodiment of the invention, an improvement of the well known electrophoretic mobility shift assay (EMSA) is conducted as follows (See FIGS. 12a and 12b):

A sample of DNA is fragmented, either through random cleavage or through specific restriction endonuclease treatment. The DNA in the sample is then split into two equal aliquots and a specific TNA is added to the first aliquot but not to the second. The first and second aliquot are then electrophoresed in an acrylamide or agarose gel, and the pattern of DNA bands (either visualized through ethidium bromide binding or through being radioactively labeled prior to electrophoresis is then compared for the two aliquots. Fragments of DNA having binding sites to which the TBA is specific are retarded in their migration through the electrophoretic medium. By using an appropriate TBA, any number of DNA sequences may be tracked in this fashion.

In a modification of the EMSA described above, fragmented TNA is hybridized with a PNA and fractionated in a first dimension. The fractionated DNA is then reacted with an appropriate TBA and the change in mobility of the DNA fragments is noted. Enhancement of the retardation is possible by adding BBAs as described above.

10. Therapeutic applications. Because of the very tight and selective nucleic acid binding characteristics of the novel TBAs described herein, therapeutic utilities are contemplated in addition to the diagnostic utilities of these compounds. Thus, a TBA comprising tight and specific binding for the HIV-LTR, by virtue of having an NF-kB p50 and an SP1 DNA recognition unit in close association (see FIG. 10, HIV-Detect II) is useful to bind up the HIV-LTR and thereby prevent transcription from this key element of the HIV genome. The unique features of the assembly sequences of the TBA allow recombinant vectors to introduce DNA encoding such a TBA into a cell and the proper folding of the expressed sequences. Once inside the cell, the nuclear localization signals of the p50 subunit directs the transport of the TBA to the nucleus where it binds tightly to the LTR of any integrated HIV, effectively shutting the pathogen down. In a prophylactic mode, one that is concerned about potential HIV exposure is administered a sufficient dose of a TBA or a recombinant vector able to express the TBA, so as to lock up any HIV that might have entered the person. In this mode, the use of the TBA is analogous to passive protection with a specific immune globulin. In the therapeutic or prophylactic mode, NLS sequences are used in place of the OSAs used in the diagnostic mode. Exemplary NLS sequences are provided as SEQ ID NOS. 72 and 103. In any event, the TBA is administered in a pharmaceutically-acceptable carrier such as a sterile salt solution or associated with a liposome or in the form of a recombinant vector, preferably one which directs expression of the TBA in a chosen cell type as are known in the art.

II. Embodiments of the Invention

In view of the foregoing description and the examples which follow, those skilled in the art will appreciate that this disclosure describes and enables various embodiments of this invention, including:

1. A probe nucleic acid (PNA) comprising:

(a) a single-stranded sequence, ½ TBR, which is capable of forming, under hybridizing conditions, a hybrid, TBR, with a ½ TBR present in a target nucleic acid (TNA);

(b) zero, one or more, and preferably one to ten single stranded sequences, ½ BBR, which is capable of forming, under hybridizing conditions, a hybrid BBR, with a ½ BBR present in a booster nucleic acid (BNA); and (c) an OSA, which is no attached support and/or indicator, or an attached support or other means of localization, including, but not limited to, attachment to beads, polymers, and surfaces, and/or indicators;

wherein said TBR is capable of binding with high affinity to a TBA, said TBA being a substance capable of discriminating between a perfect TBR and a TBR having unpaired nucleotides, and further, wherein said BBR is capable of binding with high affinity to a BBA, said BBA being a substance capable of discriminating between a perfect BBR and a BBR having unpaired nucleotides. This embodiment includes TBRs which are DNA binding protein recognition sites, such as the HIV LTR, and other DNA binding protein recognition sites in other pathogens, some of which are noted above. The PNA of this embodiment of the invention may produce a TBR which is a DNA binding protein recognition site present in the genome of a pathogen or is a binding site associated with a pathogenic condition in the human genome.

2. A booster nucleic acid (BNA) comprising:
   (a) a ½ BBR which has a sequence which is complementary to a ½ BBR sequence in a PNA or another BNA already hybridized to the PNA and which is capable of forming, under hybridizing conditions, a hybrid, BBR, with the PNA;
   (b) an OSA attached support or other means of localization, including, but not limited to, attachment to beads, polymers, and surfaces, and/or indicators; and
   (c) additional hybridization sites, ½ BBRs, for hybridization with additional BNAs;
   wherein said BBR is capable of binding with high affinity to a BBA, said BBA being a substance capable of discriminating between a perfect BBR and a BBR having unpaired nucleotides.

3. A Hairpin Nucleic Acid (HNA) comprising a single-stranded sequence, ½ BBR, which under hybridizing conditions is capable of forming a hairpin while at the same time binding to a BNA to form a BBR capable of binding a BBA, wherein said BBR is capable of binding with high affinity to a BBA, said BBA being a substance capable of discriminating between a perfect BBR and a BBR having unpaired nucleotides.

4. A method for detecting a specific TNA sequence, comprising the steps of:
   (a) hybridizing said TNA with a PNA as described above;
   (b) hybridizing said PNA with a BNA containing a ½ BBR whose sequence is complementary to a ½ BBR sequence in the PNA;
   (c) adding the products of steps (a) and (b) containing a TBR and a BBR, to a surface, liquid or other medium containing a TBA;
   (d) adding BBAs to the mixture in step (c) wherein said BBA comprises:
      (i) a molecule or a portion of a molecule which is capable of selectively binding to a BBR; and
      (ii) a detectible indicator; and
   (e) detecting signal produced by the indicator attached to the BBA. This method includes the use of a protein indicator, including enzymes capable of catalyzing reactions leading to production of colored reaction products. It also includes indicators such as a radionuclide or colored beads.

5. A method for detecting the presence in a sample of a specific Target Nucleic Acid, TNA, which comprises:
   (a) contacting said sample with a Probe Nucleic Acid, PNA, which, upon hybridization with said TNA if present in said sample, forms a Target Binding Region, TBR, which is capable of binding a Target Binding Assembly, TBA;
   (b) contacting said sample, already in contact with said PNA, with a TBA capable of binding to any TBRs formed by the hybridization of said PNA and said TNA in the sample.

6. A method for detecting or localizing specific nucleic acid sequences with a high degree of sensitivity and specificity which comprises:

(a) adding PNAs containing a ½ BBR and a ½ TBR to a sample containing or suspected of containing TNAs containing ½ TBR sequences, to form a complex having target binding regions, TBRs, formed by the hybridization of complementary ½ TBRs present in the PNAs and TNAs respectively;
   (b) binding the TBRs formed in step (a) to an immobilized TBA to form a TBA-TNA-PNA complex;
   (c) adding Booster Nucleic Acids, BNAs, containing booster binding regions, ½ BBRs, to the complex formed in step (b) such that the ½ BBRs in the BNAs hybridize with the ½ BBR sequences present in the PNAs or to ½ BBRs present in BNAs already bound to the PNA, to form BBRs, such that TBA-TNA-PNA-(BNA)$_n$ complexes are formed;
   (d) adding Hairpin Nucleic Acids, HNAs, containing ½ BBR sequences, to the complex formed in step (c) such that the ½ BBRs in the HNAs hybridize with any available ½ BBR sequences present in the BNAs of the complex of step (c), thereby capping the extension of the BNAs onto the TBA-TNA-PNA-(BNA)$_n$ complexes of step (c) to form BA-TNA-PNA-(BNA)$_n$-HNA complexes;
   (e) adding Booster Binding Assemblies, BBAs, linked to indicator moieties, to the TBA-TNA-PNA-(BNA)$_n$-HNA complexes formed in step (d) to form TBA-TNA-PNA-(BNA-BBA)$_n$-HNA complexes; and
   (f) detecting the signals produced by the indicator moieties linked to the TBAs, PNAs, BNAs, BBAs or HNAs in the TBA-TNA-PNA-(BNA-BBA)$_n$-HNA complexes of step (e);

wherein:
   the TNA comprises:
   (i) one or more specific ½ TBR DNA sequences, the presence or absence of which in a particular sample is to be confirmed;
   the PNA comprises:
   (i) a single-stranded sequence, ½ TBR, which is capable of forming, under hybridizing conditions, a hybrid, TBR, with a ½ TBR present in a target nucleic acid (TNA);
   (ii) a single stranded sequence, ½ BBR, which is capable of forming, under hybridizing conditions, a hybrid BBR with a ½ BBR present in a booster nucleic acid (BNA); and
   (iii) an OSA, which is no attached support and/or indicator, or an attached support or other means of localization, including, but not limited to, attachment to beads, polymers, and surfaces, and/or indicators;
   the BNA comprises:
   (i) a ½ BBR, as shown in FIG. 1(IIb), which has a sequence which is complementary to a ½ BBR sequence in a PNA and which is capable of forming, under hybridizing conditions, a hybrid, BBR, with the PNA;
   (ii) an OSA attached support or other means of localization, including, but not limited to, attachment to beads, polymers, and surfaces, and/or indicators;
   (iii) additional hybridization sites, ½ BBRs, for other BNAs; and
   (iv) sequences, ½ BBRs, which can hybridize to BNAs already hybridized to the PNA;
   the BBA comprises:
   (i) a molecule or a portion of a molecule which is capable of selectively binding to a BBR; and
   (ii) no attached support and/or indicator, or an attached support or other means of localization, including, but not limited to, attachment to beads, polymers, and surfaces, and/or indicators;

and the TBA comprises:

(i) a molecule or a portion of a molecule which is capable of selectively binding to a TBR; and (ii) no attached support and/or indicator, or an attached support or other means of localization, including, but not limited to, attachment to beads, polymers, and surfaces, and/or indicators.

7. An improvement to a solid phase hybridization method for detecting the presence of a target polynucleotide involving: immobilizing a target polynucleotide, if present in a test sample, directly or via an intermediate capture structure, on a solid phase at a capture site; before, during or after said immobilization, attaching a detectable label to said target polynucleotide, if present; and detecting said label, if any, at said capture site; the improvement comprising:

(a) using a Target Binding Assembly, TBA, as the means for achieving immobilization of said target polynucleotide, wherein said TBA binds only to a perfect hybrid formed between a specific Probe Nucleic Acid, PNA, and said target nucleic acid such that a perfect Target Binding Region, TBR, recognizable by said TBA is formed; and (b) including in the PNA a single stranded sequence, ½ BBR, capable of binding a Booster Nucleic Acid, BNA, containing a single stranded complementary ½ BBR which, upon hybridization with the ½ BBR in the PNA, forms a BBR capable of binding labeled Booster Binding Assemblies, BBAs.

8. A target binding assembly, TBA, comprising one or more DNA recognition units, linker sequence(s), assembly sequence(s), asymmetry sequence(s), nuclear localization signal sequence(s) (NLS) and OSA(s). The DNA recognition unit may be an NF-kB binding unit, an SP1 binding unit, a TATA binding unit, a human papillomavirus binding unit, an HIV LTR binding unit, or a binding unit for any other fragment of specific sequence the detection of which is desirable and which can be achieved through specific association with the TBA. Such recognition units include, but are not limited to those exemplified herein as SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, and SEQ ID NO. 73. Linker sequences such as oligopeptides which do not interfere with the DNA recognition function of the DNA recognition unit and which provide stability and control over the spacing of the DNA recognition unit from the remainder of the TBA. Examples of such linker sequences are well known in the art and include, but are not limited to oligopeptide sequences from the interdomain primary sequence of a structural protein. Assembly sequences include oligopeptide sequences which direct the folding and association of DNA recognition units. A preferred example of such sequences are oligopeptides derived from the bacteriophage lambda cro protein. The asymmetry sequence directs the association of DNA recognition and assembly sequences in a predetermined order. Such asymmetry sequences are exemplified by sequences derived from insulin, relaxin, gonadotropic hormone, FSH, HCG, LH, ACTH, including but not limited to SEQ ID NOS. 85–92. With reference to FIGS. 14 and 15, SEQ ID NO. 85 is an "A" and SEQ ID NO. 86 is a "B" sequence; SEQ ID NO. 87 is an "A" and SEQ ID NO. 88 is a "B" sequence' SEQ ID NO. 89 is a human relaxin "A" and SEQ ID NO. 90 is a human relaxin "B" sequence; SEQ ID NO. 91 is a skate relaxin "A" and SEQ ID NO. 92 is a skate relaxin "B" sequence. In addition, the TBA may contain nuclear localization signal sequences, NLS, which direct the migration and uptake of a protein or complex associated with said NLS into the nucleus of a cell. Examples of such NLS sequences are provided as SEQ ID NOS. 72 and 103. Preferred embodiments of the TBA include but are not limited to HIV Detect I–IV or HPV Detect I–IV, and SEQ ID NOS. 109–116.

9. Methods of using the novel TBAs of this invention include, but are not limited to a method of using the TBA to bind a particular nucleic acid sequence in a target nucleic acid sample which comprises:

(a) fragmenting the nucleic acid in the target nucleic acid sample;

(b) contacting, under hybridizing conditions, the fragmented nucleic acid with a probe nucleic acid complementary to the particular nucleic acid sequence of interest, wherein said probe nucleic acid, upon hybridization with said particular nucleic acid sequence of interest forms a target binding region to which said TBA specifically binds. In this method, the probe nucleic acid, in addition to sequences complementary to said particular nucleic acid sequence of interest, also may have additional sequences to which a booster nucleic acid can bind to form a booster binding site to which a labeled booster binding assembly can bind to provide a signal showing and amplifying the binding of the probe nucleic acid to the target nucleic acid sequence of interest.

An additional aspect of this invention not requiring fragmentation of Target Nucleic Acid, involves administration of the TBA to a patient in need of such treatment of a therapeutically or prophylactically effective amount of said TBA, which comprises administering the TBA, either in the form of a purified protein complex or in the form of a recombinant vector which, upon entry into the patient is able to express the TBA, such that the TBA binds the particular nucleic acid sequence to achieve the desired prophylactic or therapeutic result. This may include providing a dosage which can be determined by routine experimentation to be sufficient to prevent establishment of an active infection by a pathogen. Dosages of purified TBAs may be in the range of about 0.001 to 100 mg/kg. When provided as a recombinant expression vector which will direct the in vivo expression and folding of the TBA, dosages of the recombinant DNA may be substantially lower, particularly if provided in the form of non-pathogenic viral vector. The methods of using the TBAs also include monitoring the shift in mobility of nucleic acids in target nucleic acid samples as a function of the size such that binding of the TBA to a particular fragment in the sample modifies the mobility of the fragment. This aspect of the method provides a useful method of analyzing nucleic acid fragments for particular aberrations, such as might be found associated with metastases.

10. Diagnostic or forensic kits useful in determining the presence of an infection, the susceptibility to a disease, or the origin of a particular nucleic acid containing sample.

11. A method of assembling multimeric TBAs in vivo which comprises introducing nucleic acids encoding component TBAs into a cell. The component TBAs should each contain a DNA recognition unit, assembly sequences, asymmetry sequences, and nuclear localization signal sequences. Linker sequences, optionally included if TBA footprinting experiments indicate the need for such linkers to attain optimal geometry of the multimeric TBA. Upon in vivo expression of each component TBA and proximal binding, via the DNA recognition unit of each component TBA to nucleic acid sequences encountered in the nucleus or elsewhere in the cell, component expressed TBAs are directed to assemble via the included assembly and asymmetry sequences into multimeric TBAs. As described above, such multimeric TBAs will have the advantage of binding specifically with high affinity to TBRs in a specific target sequence, but not at all or with very low affinity to cousin nucleic acids.

The foregoing description of the invention will be appreciated by those skilled in the art to enable preferred embodiments as well as the best mode of this invention. Without limiting the subject matter to the specifics of the examples provided hereinafter, the following examples are provided to further guide those skilled in the art on methods of practicing this invention. Standard recombinant DNA techniques as disclosed in Sambrook, Fritsch, and Maniatis (1989) *Molecular Cloning: A Laboratory Manual,* 2nd Ed., Cold Spring Harbor Laboratory Press, Cold Spring Harbor, N.Y., and more recent texts are not disclosed as these are now well within the skill of the ordinary artisan.

EXAMPLE 1

Preparation of PNAs and Labeling of PNAs

Probe nucleic acids, PNAs, may be prepared by means well known in the art. Thus, single stranded polynucleotide PNAs of defined sequence may be prepared via solid phase chemical synthesis according to Merrifield. PNAs may be prepared by automated synthesis using commercially available technology, such as resins and machines produced or marketed by Applied Biosystems, ABI, or other manufacturers. Alternatively, through known recombinant DNA methods, particular PNA sequences are synthesized in vivo, for example by cloning a duplex PNA into a vector which can replicate in *E. coli,* large quantities of the duplex PNA may be prepared. Multimers of the PNA may be cloned into the vector such that for each mole of vector, several moles of PNA is liberated upon digestion of the vector with a restriction fragment flanking the PNA sequence. Subsequent to synthesis or recombinant production, the PNAs are purified by methods well known in the art such as by gel electrophoresis or high pressure liquid chromatography (HPLC). If the PNA is produced as a duplex, prior to use in a hybridization assay for detection of target nucleic acid sequences, the strands of the PNA are separated by heating or other methods known in the art.

The specific sequence of bases in the PNA is chosen to reflect the sequence to be detected in a TNA, with the proviso that, according to this invention, the PNA contains a ½ TBR sequence, which is one that upon hybridization of the PNA and TNA, a TBR is formed. As there are an essentially unlimited number of such sequences known in the art, the choice of the PNA sequence is amenable to selection by the skilled researcher for any given application. The sequence of the HIV LTR is one such sequences which upon hybridization of a PNA encoding portions of the LTR with TNAs encoding the HIV LTR, TBRs capable of binding the NF-kB or SP1 DNA binding proteins are formed.

In addition to sequences which will form a TBR upon hybridization, the PNA also may contain a ½ BBR. This sequence is one which, upon hybridization with a booster nucleic acid, BNA, forms a BBR which is capable of binding a BBA. The BBA is preferably a DNA binding protein having high affinity for the BBR sequence.

In this particular example, hybridization between a PNA having as a ½ TBR, SEQ ID NO. 4 and, at the 3' end of that sequence, a ½ BBR sequence shown as SEQ ID NO. 35. The PNA encoding these sequences is either used without labeling or is labeled with a radioactive isotope such as $P^{32}$, $S^{35}$, or a similar isotope, according to methods known in the art. Alternatively, the PNA is bound to a bead of between 0.01 to 10 μm, which may be colored for easy visual detection. This label forms the OSA as described in the specification. This probe hybridizes with HIV LTR sequences to form a TBR that binds NF-kB. In addition, the PNA hybridizes with BNAs having a complementary ½ BBR to form a bacteriophage lambda left operator that binds either cro or lambda repressor proteins.

In a manner similar to that described above, PNAs are used wherein the ½ TBR is any one of SEQ ID NO. 5 or SEQ ID NOS. 7–34, and a ½ BBR, such as SEQ ID NO. 35 or SEQ ID NO. 36 is either at the 3' end or 5' end of the ½ TBR.

EXAMPLE 2

Preparation and Labeling of BNAs

Similar to the methods described in Example 1 for preparation and labeling of PNAs, BNAs are prepared and labeled according to methods known in the art. As described in U.S. Pat. No. 4,556,643, herein incorporated by reference (see particularly Example 1), DNA sequences encoding particular DNA binding sequences may be mass produced by cloning into a replicable vector. Furthermore, similar to that disclosure, the ½ TBR and ½ BBR sequences may be co-linearly produced in this fashion, with the distinction, however, that according to the instant invention, the ½ TBR sequence itself forms a DNA binding protein recognition site and the ½ BBR, while forming a DNA binding protein recognition site, also provides a means of amplifying the signal produced upon binding of the ½ TBR to complementary sequences in the TNA by providing for polymerization of BNAs onto the TNA bound PNA. To enable this, a sequence such as SEQ ID NO. 35, which encodes the left operator of bacteriophage lambda, is provided with additional sequences such that an overhang sequence is created on one or both ends of the BNA upon hybridization with the PNA.

As a specific example, vectorial polymerization of BNAs onto a TNA is provided by SEQ ID NOS. 40–43. In this example, SEQ ID NO. 40 encodes two ½ TBRs which will hybridize with two ½ TBRs in a TNA to form two NF-kB binding sites, while at the same time providing a bacteriophage lambda left operator ½ BBR, which additionally is terminated at the 3' end with the recognition site for the restriction enzyme PstI. Addition of the BNA, SEQ ID NO. 41, with the ½ BBR complementary to the ½ BBR on the PNA, SEQ ID NO. 40, completes the BBR while at the same time completing the PstI recognition site, leaving a four base overhang for hybridization with additional BNAs. Accordingly, SEQ ID NO. 42 is added which has a four base pair sequence at the 3' end which is complementary to the four-base overhang remaining from the hybridization of SEQ ID NOS. 40 and 41. In addition, SEQ ID NO. 42 is provided with a five base sequence at its 5' end which forms part of a BamHI recognition site. The growing polymer of BNAs is extended further by addition of the BNA SEQ ID NO. 43, which is complementary to SEQ ID NO. 42, completing the BBR while at the same time completing the BamHI recognition site and leaving a four base overhang which may be further hybridized with BNAs having complementary sequences. In this fashion, the BNAs may be hybridized extensively so as to greatly amplify the signal of a single PNA-TNA hybridization event.

As with the PNAs described in Example 1, the BNAs may be used in an unlabeled form or may be labeled according to methods known in the art and described in Example 1. It will also be appreciated that, rather than produce the BNA polymer by sequential addition of BNAs to the PNA-TNA complex, the BNA polymer may be preformed and added directly to the PNA-INA complex. One simple method for preforming such a BNA polymer includes the recombinant production of a vector in which multimers of the BNA are provided with a unique restriction site at either end of the polymer. This polymer of BNAs containing multiple BBRs is cut out of the vector and hybridizes to a single stranded ½ BBR remaining in the PNA upon hybridization of the PNA and the TNA. This is accomplished by providing a single stranded sequence in the PNA complementary to an overhang produced in the BNA polymer when it is excised from the production vector.

EXAMPLE 3

Production of HNAs and Their Use for Capping BNA Polymers

The HNAs of this invention are produced according to methods known in the art for polynucleotide production as described in Examples 1 and 2 for PNAs and BNAs. In the production of the HNAs, however, the sequence of the HNA is specifically designed so that a substantial portion of the HNA forms a self-complementary palindrome to form a hairpin, while at the same time, leaving in single stranded form enough bases to be able to hybridize with single stranded sequences in the growing chain of BNAs described in Example 2.

In this Example, a HNA of SEQ ID NO. 44 is provided to cap the extension of BNAs onto the PNA in Example 2 after the addition of the BNA, SEQ ID NO. 43. This is accomplished because SEQ ID NO. 44, while having a palindromic sequence that forms a stable hairpin, also has a sequence at the 5' end of the HNA which completes the BamHI sequence formed by the hybridization of SEQ ID NO. 42 and SEQ ID NO. 43. Naturally, termination of the polymer after addition of only 3 BNAs is for the purpose of simplicity in demonstrating the invention. As described above, this polymerization may be continued essentially indefinitely to amplify the signal of the PNA-TNA hybridization event. Once the HNA hybridizes to the growing chain of BNAs, the polymer is capped and no further extension of the polymer is possible.

EXAMPLE 4

Preparation of TBAs and BBAs, Labeling, and Immobilization Thereof

The TBAs and BBAs which may be used according to the instant invention include any substance which can specifically bind to the TBRs and BBRs formed by hybridization of the PNAs, TNAs and BNAs. Use of DNA binding proteins forms one example of such substances.

For this example, the TBA is the dimer of the DNA binding portion of p50, and the BBA is the lambda cro protein. These proteins may be produced according to methods known in the art. The genes for both of these proteins have been cloned. Thus, these proteins are recombinantly produced and purified according to methods known in the art. Furthermore, these proteins are labeled, either with a radioisotope, such as radioactive iodine, or with an enzyme, such as beta-galactosidase or horseradish peroxidase, or with a fluorescent dye such as fluorescein or rhodamine, according to methods well known in the art. In addition, either or both of the TBA and BBA may be immobilized on a solid surface such as the surface of a microtiter plate or the surface of a bead, such as a colored bead of diameter anywhere from 0.01 to 10 $\mu$m. The labels on the TBAs and BBAs may be the same or different.

In this example, the TBA containing the dimeric p50 DNA binding domain is labeled with rhodamine, while the BBA, cro, is labeled with fluorescein. Accordingly, upon hybridization of the PNAs, TNAs, BNAs and HNAs as described in this patent disclosure and the foregoing and following examples, the nucleic acid hybrids, if formed, are contacted with excess labeled TBA and cro. The fluorescence of these labels is measured according to known methods and, detection of both signals is indicative of the presence of ½ TBR sequences in the TNA. The differential signal produced by the fluorescence of the NF-kB and cro is a measure of the degree to which the polymerization of BNAs onto the PNA-TBA hybrid has resulted in amplification of the signal. Amplification from one to over a thousand fold is contemplated according to the method of this invention.

EXAMPLE 5

Hybridization of two PNAs with a TNA and Discrimination Between a TNA and a CNA

The PNAs, PNA1, SEQ ID NO. 40 and PNA2, SEQ ID NO. 45, are used in about ten-fold molar excess over the concentration of TNAs in a test sample. For this example, an isolated duplex HIV LTR, wherein one strand of which has the sequence SEQ ID NO. 37, shown in. FIG. 7, and the other strand of which is complementary to the sequence shown in FIG. 7, is used as the TNA. A duplex isolated CNA is also used in this example, one strand of which has the same sequence as SEQ ID NO. 37, except that, in the first NF-kB binding site shown in FIG. 7, at the center of the binding site, position 1 in FIG. 7, instead of a "T," there is an "A," the complementary strand of which therefore mismatches with the SEQ ID NO. 40 PNA at that location.

SEQ ID NO. 40 and SEQ ID NO. 45 are both added to separate reactions, the first containing the above described TNA and the second containing the above described CNA. The samples are solubilized in an appropriate hybridization buffer, such as 10 mM Tris (pH 7.5), 1 mM EDTA. The samples are heated to about 90° C. for about five minutes to strand separate the duplex TNAs and CNAs in the samples, and then the samples are allowed to cool to allow strands of PNAs, TNAs and CNAs to anneal.

Once the hybridization has gone to completion, which can be determined according to known methods such as by calculating the t½ based on base compositions and annealing temperature according to known methods, the SEQ ID NO. 40 PNA is polymerized by addition of BNAs as in Example 2 and the SEQ ID NO. 45 PNA2 probe is polymerized with BNAs starting with Sph1 recognition site overhang. Following addition of the BNAs and a brief hybridization period, the separate samples are added to beads coated with covalently immobilized NF-kB, and the NF-kB is allowed to bind to any TBRs formed in the TNA and CNA samples. After about 15 minutes of binding, the samples are washed twice with about three volumes of an appropriate washing buffer, such as 10 mM Tris, pH 7.5, 100 mM NaCl, or another buffer pre-determined not to interfere with NF-kB, or bacteriophage lambda CI repressor protein binding activity. After each wash, the beads are allowed to settle under gravity or by brief centrifugation. This removes any nucleic acids which do not have a perfect NF-kB binding site formed by hybridization of the PNA1 and TNA sequences.

After the final wash, bacteriophage lambda CI repressor protein labeled with a radioactive isotope, such as with radioactive iodine, or labeled with an enzyme, such as horseradish peroxidase, with colored beads, or with a fluorescent label is added to each sample. The samples are then washed several times (about 3) with several volumes (about 2) of an appropriate washing buffer such as 10 mM Tris, pH 7.5, 100 mM NaCl, or another buffer pre-determined not to interfere with NF-kB, or bacteriophage lambda CI repressor protein binding activity. After each wash, the beads are allowed to settle under gravity or by brief centrifugation. Following the last settling or centrifugation, the bound label is quantitated by detecting the bound radioactivity, liberated color in an enzymatic assay, color of bound beads, or fluorescence detection. Alternatively, an anti-CI antibody can be added and a standard sandwich enzyme linked immunoassay or radioimmunoassay performed to detect bound repressor. In addition, as a negative control (background), all of the foregoing manipulations are carried out in tandem with a sample in which beads are used having no immobilized NF-kB.

As a result of the foregoing assay, the control and CNA containing samples have similarly low signals while the TNA containing sample has a signal well above background.

EXAMPLE 6

A Test Kit for the Detection of HIV

A. Kit contents:
1. Microtiter plate.
2. 1 mg/mL solution of recombinantly produced NF-kB in tris-buffered saline.
3. Tube containing single stranded HIV PNAs (a mixture of pre-mixed oligonucleotides encoding two NF-kB ½ binding sites, i.e. a mixture of SEQ. ID. Nos.7 and 8).
4. Tube containing single stranded human genomic PNA, SEQ ID NO. 1.
5. Tube of nuclease (PstI).
6. Tube of protease.
7. Tube containing pre-polymerized BNA's, 100 repeat units of bacteriophage lambda $O_R$, capped with an HNA but with free ½ BBRs available for binding to PNA-TNA hybrids.
8. Tube of horseradish peroxidase (hrp) conjugated cro.
9. Tube of hrp colored substrate.
10. Tris buffered saline, 100 mL.
11. Lancet.
12. Reaction tubes A, B, C, each containing 250 µL of distilled water.
13. Medicine dropper.

B. Assay method:
(a) The microtiter plate (item 1) is coated with the solution of recombinantly produced NF-kB (item 2) at a concentration of 1 mg/mL in tris buffered saline overnight at 4° C. with rocking.
(b) Three drops of blood of the test taker is obtained by pricking a finger with the lancet (reagent 11), and a drop of blood is dispensed into each of reaction tubes A, B, and C (reagent 12).
(c) Into each tube is dispensed one drop of protease solution (reagent 6) with the medicine dropper (item 12) and the tube agitated and allowed to sit for 5 minutes.
(d) One drop of nuclease (item 5) is added to each of tubes A–C using the medicine dropper and the tubes agitated and allowed to sit for 10 minutes.
(e) One drop of item 3 is added to tube A (test sample); one drop of item 4 is added to tube B (positive control); and one drop of saline (item 12) is added to tube C as a negative control. The tubes are heated to 50° C. in hot water and allowed to cool to room temperature over one hour.
(f) While the hybridization is allowed to occur in step (d), the excess protein is drained from the surface and the microtiter plate, from step (a), and the plate is rinsed with tris buffered saline (tube 10).
(g) The contents of tubes A–C from step (e) are transferred to three wells of the microtiter plate and allowed to stand for 1 hour with rocking.
(h) The microtiter wells containing the contents of tubes A–C are rinsed with tris buffered saline and emptied.
(i) One drop of item 7 is added to each well and allowed to hybridize with any ½ BBR sites bound to the plate, over one hour, followed by three rinses with tris buffered saline.
(j) One drop of item 8 is added to each well and cro is allowed to bind to any bound BNA's over 10 minutes, followed by five, one mL washes with tris-buffered saline.
(k) One drop of hrp substrate is added to each well and color allowed to develop.

C. Results:
If wells A and B both show color development, and well C does not, the test is valid and the subject has been infected with HIV. If only well A shows color development, or if well C shows color development, the test has been performed incorrectly, and is invalid. If wells A and C show no color development but well B does, the test is valid and the individual has not been infected with HIV.

EXAMPLE 7

Production of Various Novel TBAs

Novel TBAs for use according to the instant invention are prepared as follows:

(a) NFkB/NF-kB (HIV-Detect I). A nucleic acid encoding any one of SEQ ID NOS. 63–71 or a like NF-kB DNA binding protein, is fused, in frame, to a nucleotide sequence encoding an assembly sequence, such as cro, such that the NF-kB DNA recognition sequence is encoded at amino or carboxy terminus of the cro sequence. Optionally, a linker sequence is provided between the NF-kB sequence and the cro sequence. At the other terminus of cro, a nuclear localization signal sequence, such as SEQ ID NO. 72, is optionally provided. Further, asymmetry sequences are optionally provided at the cro terminus unused by the NF-kB recognition sequence. Examples of complete TBAs are shown below.

(b) NF-kB/SP1 (HIV-Detect II). In a similar fashion to that described in (a) above, a recombinant coding sequence encoding an NF-kB recognition domain is prepared. In a separate construct, instead of SEQ ID NOS. 63–72, the coding sequence for the DNA recognition portion of SP1 is included. Such a sequence should encode all or a functional part of SEQ ID NO. 73, which is that portion of the SP1 transcription factor exhibiting DNA binding (see Kadonaga et al. [1987] *Cell* 51:1079–1090). The NF-kB-encoding vector and the SP1-encoding vector are then co-transfected into an appropriate expression system such as is well known in the art. A monomeric NF-kB recognition unit is added to complete the NF-kB recognition dimer after the assembly of the SP1 and NF-kB recognition units by the chaperone. The asymmetry sequences prevent the formation of NF-kB or SP1 dimers and direct, instead, the formation of NFkB-SP1 heterodimers (i.e., HIV-Detect II), which are then isolated from the expression system (mammalian or bacterial cells) by known methods.

(c) SP1/SP1 TBAs (HIV-Detect III). As described in (b) above, an SP1-encoding TBA construct is prepared. However, only this construct is transfected into the expression system, and asymmetry sequences allowing the formation of SP1-SP1 dimers are included.

(d) SP1-TATA (HIV-Detect IV). As described in (b) above, an SP1-encoding TBA recombinant is produced. In addition, a recombinant encoding a TBA having the binding sequence, SEQ ID NO. 74, or like sequence encoding a TATA recognition unit is prepared with asymmetry sequences complementary to those included in the SP1 TBA-encoding construct. These constructs are co-transfected and the heterodimers isolated by standard methods, including affinity purification on a DNA column having the appropriate SP1-TATA target binding regions.

(e) SP1-E2 (HPV-Detect I). An SP1-encoding construct is prepared as in (b) above. An E2 TBA-encoding construct is prepared by using a sequence encoding any one of SEQ ID NOS. 75–84 and 94–98 which are papillomavirus E2 DNA recognition units (see Hegde et al. [1992] *Nature* 359:505–512) or like recognition units, is prepared and co-transformed or co-transfected with the SP1 TBA-encoding construct. Monomeric E2 recognition unit is added to the complete E2 recognition dimer after the assembly of the E2-SP1 recognition unit by the chaperone. The heterodimer HPV-Detect I is isolated according to known methods.

(f) E2-E2 (HPV-Detect II). As described above in (e), an E2 TBA-encoding construct is prepared, except that asymmetry sequences are included which permit the formation of E2 dimers. The expressed dimers are then isolated by known methods including affinity for a dimeric E2 binding site on a DNA affinity column.

(g) E2-TATA (HPV-Detect III). As described above in (e) and (d), E2 and TATA binding TBAs are prepared (respectively), except that asymmetry sequences are included which enhance the formation of heterodimers rather than homodimers. These constructs are then co-expressed and the heterodimers are isolated.

(h) TATA-TATA HPV-Detect IV). As described above in (a) and (d), a TATA binding TBA-encoding construct is prepared using asymmetry sequences that encourage this homodimer formation and the homodimer is isolated.

(i) Other TBAs. As described above for HIV and HPV TBAs, TBAs for any given pathogen or disease state may be produced by identifying specific DNA binding proteins and forming an expression construct using appropriate linker, assembly, and asymmetry sequences.

EXAMPLE 8

In a similar fashion to the assay described in Example 5, a more stringent assay is produced by using the duplex NF-kB-SP1 binding protein prepared according to Example 6. Accordingly, the probes shown in FIG. 7 and used in Example 5 may be lengthened to reduce the interprobe distance and thereby reduce the flexibility of the DNA in the TNA.

EXAMPLE 9

Production of "High-Order" TBAs

By the appropriate use of asymmetry sequences, TBAs are produced which are dimers, trimers, tetramers, pentamers, or hexamers of particular DNA recognition units. In this fashion, a hexameric TBA is produced by making a first NF-kB p50 dimeric TBA using asymmetry sequences which enable dimer formation. In addition, the asymmetry sequences enable the tetramerization of the p50 dimer with an SP1-SP1 dimer. Finally, additional asymmetry sequences direct the hexamerization with a dimer exhibiting nuclear localization sequences. This is accomplished by incorporating, for example, asymmetry sequences from insulin, which in nature forms hexamers. This hexamer formation is directed by the sequences, SEQ ID NOS. 85 (A) and 86 (B), 87 (A) and 88 (B), 89 (A) and 90 (B), and 91 (A) and 92 (B) (see FIGS. 13 and 14).

Because of the extremely high affinity for the HIV-LTR that can be generated using a multimeric TBA, the compounds having this structure and which can be used for this purpose are referred to herein as "HIV-Lock."

An optimal HIV-Lock is defined by footprinting (according to methods well known in the art) TBAs bound to TBRs in the HIV LTR to confirm that the binding affinity of each DNA binding protein contributing to the formation of the multimeric TBA complex is downshifted relative to the affinity for any natural target sequence (i.e. CNAs) from which the DNA binding recognition unit of the TBA is derived. Any concomitant loss in binding affinity for the HIV TBRs is more than compensated for upon formation of the multimer as described below.

There may be competition between the binding of each component TBA for its TBR and assembly, via asymmetry sequences to form the multimer. This is obviated by adjusting the linkers between the chaperone and asymmetry sequences in each TBA component such that these competing events are uncoupled. The resultant reduction in the dimensionality of diffusion (effective concentration increase) for the TBA asymmetry and assembly components results in efficient formation of the multimeric complex.

On the basis of the footprinting, the length and composition of linkers is adjusted to achieve optimal discrimination between target HIV sequences and natural sequences. In this fashion, although each component TBA will have a low affinity for CNA and TBR sequences, the multimeric complex will have an extremely high affinity for the now expanded TBR recognized by the multimeric complex (the square of the affinity of each TBR recognized by each component TBA of the multimeric TBA), while still having a low affinity for CNAs. In the same fashion, other multimeric TBA complexes, aside from HIV-Lock, are prepared.

TBAs which can be formed in this fashion include the following sequences, which are assembled by linking either the protein subunits or nucleic acid sequences encoding these subunits, as follows:

| Set | Link Sequences from Groups |
| --- | --- |
| A | I + II + III |
| B | IV + V + III |
| C | IV + III | wherein groups I–V consist of sequences selected from:

| Group | Selected from Sequences |
| --- | --- |
| I | Any of SEQ ID NOS. 85–92 |
| II | Met Ser, linked to any of SEQ ID NOS 104–106, each of which is linked to SEQ ID NO. 99. |
| III | SEQ ID NO. 100 linked to any of SEQ ID NOS. 75–84 or 94–98; SEQ ID NO. 101 linked to either SEQ ID NO. 74 or SEQ |

-continued

| Group | Selected from Sequences |
|---|---|
| | ID NO. 93; or SEQ ID NO. 102 linked to SEQ ID NO. 74 or SEQ ID NO. 93; or any of SEQ ID NO. 72, 103, 73, or 63–71. |
| IV | Any of SEQ ID NOS. 104–106. |
| V | SEQ ID NO. 99. |

Specific examples of such TBAs are SEQ ID NOS. 109–116, assembled as follows:

| Set | SEQ ID NO. | Link SEQ IDS |
|---|---|---|
| A | 109 | 85 + Met Ser + 104 + 99 + 100 + 94 |
| A | 110 | 85 + Met Ser + 104 + 99 + 72 |
| A | 111 | 86 + Met Ser + 105 + 102 + 74 |
| A | 112 | 86 + Met Ser + 106 + 99 + 73 |
| A | 113 | 89 + Met Ser + 106 + 99 + 63 |
| C | 114 | 106 + 64 |
| C | 115 | 105 + 64 |
| B | 116 | 106 + 99 + 73 |

In this fashion, choosing between appropriate asymmetry sequences, assembly sequences, and DNA recognition units, many different TBAs may be formed. Furthermore, sets of these, such as SEQ ID NOS. 114 and 115, will associate with each other but dimers of SEQ ID NO. 114 or 115 will not form due to charge repulsion in the mutated assembly sequences (SEQ ID NO. 104 is cro; SEQ ID NO. 105 is a novel mutated, negatively charged cro, and SEQ ID NO. 106 is a novel mutated, positively charged cro).

Naturally, given the amino acid sequence of these TBAs, one of ordinary skill could produce recombinant nucleic acid clones encoding these, and such recombinant clones naturally form an integral part of this invention.

EXAMPLE 10

HIV Test Using "HIV-LOCK"

In much the same method as used in Example 6, the "HIV-LOCK" produced according to Example 9 is used as the TBA, reagent 2, with similar results.

EXAMPLE 11

HIV Test Using "HIV-LOCK" When Testing Blood for Donation

When the quantity of blood to be tested is not limiting, as when samples of blood for donation are to be tested for HIV contamination, tests similar to Example 6 are run, but for each of tubes A–C, about 5 mL of blood is pelleted in a tabletop centrifuge. Other reagents are scaled up as necessary to handle the larger quantity of TNA present in the sample.

EXAMPLE 12

"HIV-LOCK" as an Anti-HIV Therapeutic Agent

"HIV-LOCK" produced according to Example 9 is formulated as a 1 mg/mL solution in liposomes and injected intravenously into a subject who has been tested and confirmed to be infected with HIV. A dose of about 0.1 mg to 100 mg of "HIV-LOCK"/kilogram body mass is infused over a twenty-four hour period and the concentration of HIV p24 in the patient's serum monitored. The treatment is repeated as often as necessary, such as when elevations in the serum p24 occur.

EXAMPLE 13

Use of an HIV-TBA Construct as a Therapeutic

A recombinant retroviral or like vector is used to deliver a construct encoding an HIV-LTR binding TBA to an infected patient. The vector encodes a chaperone, such as cro, and sequences DNA for binding portions of p50. The same vector also encodes a chaperone on which an SP1 TBA folds. Asymmetry sequences are provided such that upon co-expression of the p50-TBA and the SP1-TBA in a single HIV infected cell in vivo, an immediate association occurs between these TBAs, while at the same time preventing any association between the DNA binding portion of p50 and endogenous p50 or p65 monomers. NLS sequences are also provided in the TBAs so that, upon dimer formation, the TBA immediately relocates to the nucleus of the cell and binds specifically to integrated HIV sequences, thus preventing any transcription from that locus.

For this purpose, it is desirable to select sequences encoding DNA binding domains such that the expressed monomers are assembled into a TBA which does not bind to natural human sequences. Thus, it is only upon binding of the TBA components to their target sequences that association between all components of the TBA occurs to form a complex which tightly and specifically binds the HIV LTR.

EXAMPLE 14

Diagnostic Test Kit for Human Papillomavirus

This diagnostic for human papillomavirus takes advantage of the known differential between benign and carcinogenic HPV to provide a test which indicates the susceptibility to malignancy in a patient. The papillomaviruses are a group of small DNA viruses associated with benign squamous epithelial cell tumors in higher vertebrates. At least 27 distinct human types of papillomaviruses (HPVs) have been found; many of these have been associated with specific clinical lesions. Four of these, HPV-6, HPV-11, HPV-16, HPV-18, and HPV-33 have been associated with human genital tract lesions. In general, HPV-6 and HPV-11 DNAs have been found associated with benign lesions of the genital tract. HPV-16, HPV-18, and HPV-33 have also been found associated with premalignant and malignant lesions and are transcribed in most cell lines established from cervical carcinomas. HPV-16, HPV-18, and HPV-33 are likely to be only two members of a large set of HPV DNAs associated with malignant human cervical carcinomas.

Animal models have shown that benign papillomavirus lesions can progress to malignant lesions in the presence of a co-carcinogen. HPV DNA has been found in metastases of cervical carcinomas. In malignant cervical lesions, HPV DNA is usually integrated into the human genome, but there may also be extrachromosomal HPV DNA present. Integration of HPV to form the provirus usually results in the disruption of the viral E2 open reading frame (ORF). Despite disruption of the E2 ORF, and examination of cell lines from several cervical carcinomas has shown transcriptionally active and integrated HPV-16 and HPV-18. When HPV-16 genomes which are present in the human cervical carcinoma cell lines SiHa and CaSki have been examined, there are differences found in the integration of HPV-16. In the SiHa line, the single HPV-16 genome integration occurred at bases 3132 and 3384, disrupting the E1 and E2 ORFs with a deletion of 0.3 kb. An additional 50-basepair deletion of HPV-16 DNA resulted in the E2 and E4 OFRs being fused. The 5' portion of the HPV-16 DNA, consisting of the disrupted E2 ORF, is ligated to continuous human right flanking sequences. In addition, a single additional guanine is detected at nucleotide 1138 in the middle of the E1 ORF. This basepair addition results in the fusion of the E1a and E1b ORFs to a single E1 ORF.

The complete genome of HPV-16 is available on GenBank as accession number K02718; the complete genome of HPV-33 is available on GenBank as accession number M12732; the complete genome of HPV-18 is available on GenBank as accession number X05015.

As a preliminary screen, the fact of an HPV infection is established for a given cervical biopsy sample by a simple "yes/no" type of analysis using, for example, any or all of the PNAs SEQ ID NOS. 46–53 and an E2 TBA as described above (i.e., fragment DNA, binding the PNA, immobilize with the TBA, and detect signal with BNAs and BBAs).

Once a biopsy sample is found to be positive for HPV, additional information is obtained as to the malignancy potential of the HPV by analyzing the integration status of the virus in the human genome.

1. Fragment the DNA in the cervical biopsy sample and hybridize to a blocking probe having the sequence, SEQ ID NO. 60. This probe will bind to all the fragments in the DNA which have not spliced out the 0.3 kb fragment.

2. Expose the DNA in the biopsy sample to a PNA having the sequence, SEQ ID NO. 61. This probe will only bind to fragments which have deleted the 0.3 kb fragment (the blocking probe will prevent the looping out of the large deletion segments if present).

3. A PNA having SEQ ID NO. 62 is hybridized with SEQ ID NO. 41 to form a BBR which will bind to cro or λ CI repressor as a BBA, leaving a single-stranded portion capable of hybridizing with the TATA site on SEQ ID NO. 61. This added to form a TBR on the 5' end of the large deletion.

4. The TBR is immobilized by a TBA having a TATA binding protein DNA recognition unit.

5. The bound fragments are detected by adding BNAs and BBAs as described above.

Detection of signal in this assay indicates that the large fragment is deleted in HPV present in the TNA. Since this deletion is correlated with malignancy, this assay provides insight into the malignancy potential of the HPV infection. This conclusion can be confirmed by performing an analogous assay based on the deletion of the 52-basepair fragment which is also correlated with HPV-induced malignancy.

The TBP recognition unit used in the TBA for this assay may be chosen, for example, from a sequence such as SEQ ID NO. 70 or SEQ ID NO. 93.

It should be understood that the examples and embodiments described herein are for illustrative purposes only and that various modifications or changes in light thereof will be suggested to persons skilled in the art and are to be included within the spirit and purview of this application and the scope of the appended claims. It will be understood that sequences provided herein are exemplary only and that other like sequences suggested by these could be used in the methods of this invention. It will also be understood that although any sequence provided herein might be designated as linear, it could be used in a circularly or otherwise permuted form and although designated as not being antisense, it could be used in the coding or non-coding form or to bind to coding or non-coding complementary sequences.

What is claimed is:

1. A method for detecting or localizing specific nucleic acid sequences with a high degree of sensitivity and specificity which comprises:
   (a) adding PNAs containing a ½ BBR and a ½ TBR to a sample containing or suspected of containing TNAs containing ½ TBR sequences, to form a complex having target binding regions, TBRs, formed by the hybridization of complementary ½ TBRs present in the PNAs and TNAs respectively;
   (b) binding the TBRs formed in step (a) to a TBA to form a TBA-TNA-PNA complex, provided that said binding may occur prior to, during or subsequent to said hybridization of step (a);
   (c) adding Booster Nucleic Acids, BNAs, containing booster binding regions, ½ BBRs, to the complex formed in step (b) such that the ½ BBRs in the BNAs hybridize with the ½ BBR sequences present in the PNAs or to ½ BBRs present in BNAs already bound to the PNA, to form BBRs, such that TBA-TNA-PNA-(BNA)$_n$ complexes are formed;
   (d) adding Hairpin Nucleic Acids, HNAs, containing ½ BBR sequences, to the complex formed in step (c) such that the ½ BBRs in the HNAs hybridize with any available ½ BBR sequences present in the BNAs of the complex of step (c), thereby capping the extension of the BNAs onto the TBA-TNA-PNA-(BNA)$_n$ complexes of step (c) to form TBA-TNA-PNA-(BNA)$_n$-HNA complexes;
   (e) adding Booster Binding Assemblies, BBAs, linked to indicator moieties, to the TBA-TNA-PNA-(BNA)$_n$-HNA complexes formed in step (d) to form TBA-TNA-PNA-(BNA-BBA)$_n$-HNA complexes, provided that said BBAs are added prior to, concurrent with or subsequent to addition of said BNAs of step (c); and
   (f) detecting the signals produced by the indicator moieties linked to the TBAs, PNAs, BNAs, BBAs or HNAs in the TBA-TNA-PNA-(BNA-BBA)$_n$-HNA complexes of step (e);

wherein the TNA comprises:
   (i) one or more specific ½ TBR sequences, the presence or absence of which in a particular sample is to be confirmed;

the PNA comprises:
   (i) a single-stranded sequence, ½ TBR, which is capable of forming, under hybridizing conditions, a hybrid, TBR, with a ½ TBR present in a target nucleic acid (TNA);
   (ii) a single stranded sequence, ½ BBR, which is capable of forming, under hybridizing conditions, a hybrid BBR with a ½ BBR present in a booster nucleic acid (BNA); and
   (iii) an OSA, which is no attached support and/or indicator, or an attached support or indicator or both selected from the group consisting of attachment to beads, polymers, proteins, peptides and surfaces, and/or indicators;

the BNA comprises:
   (i) a ½ BBR, as shown in FIG. 1(IIb), which has a sequence which is complementary to a ½ BBR sequence in a PNA and which is capable offorming, under hybridizing conditions, a hybrid, BBR, with the PNA;
   (ii) an OSA, which is no attached support or indicator, or is an attached support or indicator or both selected from the group consisting of attachment to beads, polymers, proteins, peptides, and surfaces, and/or indicators;
   (iii) additional hybridization sites, ½ BBRs, for other BNAs; and
   (iv) sequences, ½ BBRs, which can hybridize to BNAs already hybridized to the PNA;

the BBA comprises:
   (i) a molecule or assembly, or a portion of a molecule or assembly which is capable of selectively binding to a BBR; and
   (ii) no attached support and/or indicator, or an attached support or indicator or both which is selected from the group consisting of attachment to beads, polymers, proteins, peptides and surfaces, and/or indicators;

and the TBA comprises:

(i) a molecule or assembly, or a portion of a molecule or assembly which is capable of selectively binding to a TBR; and (ii) no attached support and/or indicator, or an attached support or indicator or both which is selected from the group consisting of attachment to beads, polymers, proteins, peptides and surfaces, and/or indicators.

2. In a solid phase hybridization method for detecting the presence of a target polynucleotide involving: immobilizing a target polynucleotide, if present in a test sample, directly or via an intermediate capture structure, on a solid phase at a capture site; before, during or after said immobilization, attaching a detectable label to said target polynucleotide, if present; and detecting said label, if any, at said capture site; the improvement comprising:

(a) using a Target Binding Assembly, TBA, as the means for achieving immobilization of said target polynucleotide, wherein said TBA is a nucleic acid binding molecule or assembly which cooperates in and stabilizes the hybridization of the target nucleic acid, TNA, with a specific probe nucleic acid, PNA, thereby forming one or more TBRs, wherein the TBA is capable of binding to and stabilizing the probe-target hybrid in a sequence specific manner, and further wherein the TBA is capable of discriminating between a hybrid formed by the probe and the target nucleic acid, and a hybrid having one or more mismatches formed by the probe and a closely related or unrelated sequence; and (b) including in the PNA a single stranded sequence, ½ BBR, capable of binding a Booster Nucleic Acid, BNA, containing a single stranded complementary ½ BBR which, upon hybridization with the ½ BBR in the PNA, forms a BBR capable of binding one or more labeled or unlabeled Booster Binding Assemblies, BBAs.

3. A method for nucleic acid detection comprising (a) obtaining a sample containing a hybrid to be detected or containing a target nucleic acid and a probe nucleic acid which hybridize to form a probe-target hybrid; and (b) contacting the hybrid of step (a) with a nucleic acid binding molecule or assembly, TBA, wherein the TBA is capable of binding to and stabilizing the probe-target hybrid in a sequence specific manner, and further wherein the TBA is capable of discriminating between a hybrid formed by the probe and the target nucleic acid, and a hybrid having one or more mismatches formed by the probe and a closely related or unrelated sequence.

4. The method of claim 3 which further comprises contacting the hybrid of step (a) or (b) with a label that binds specifically to the nucleic acid bound by the TBA.

5. The method of claim 4 wherein said specific label is a booster nucleic acid which hybridizes with a portion of the probe nucleic acid not involved in hybridization with the target nucleic acid.

6. The method of claim 3 wherein the probe nucleic acid, PNA, comprises:

(a) a single-stranded sequence, ½ TBR, which is capable of forming, under hybridizing conditions, a hybrid, TBR, with a ½ TBR present in a target nucleic acid (TNA);

(b) a single stranded sequence, ½ BBR, which is capable of forming, under hybridizing conditions, a hybrid BBR, with a ½ BBR sequence present in a booster nucleic acid (BNA) upon contacting said BNA with said PNA; and (c) an OSA, which is no attached support and/or indicator, or an attached support or indicator or both, selected from the group consisting of beads, polymers, proteins, peptides, surfaces, and indicators;

wherein said TBR is capable of binding with high affinity to said nucleic acid binding molecule or assembly (TBA) and wherein said BBR is capable of binding with high affinity to a second nucleic acid binding molecule or assembly (BBA), said BBA being a nucleic acid binding molecule or assembly which cooperates in the PNA-BNA or BNA-BNA hybridization, said BBA capable of binding to and stabilizing PNA-BNA or BNA-BNA hybrids in a sequence specific manner, and further wherein the BBA is capable of discriminating between a hybrid formed by the PNA or BNA and a BNA, and a hybrid having one or more mismatches formed by the PNA or BNA and a closely related or unrelated sequence.

7. The method of claim 6 wherein said booster nucleic acid (BNA) comprises:

(a) a ½ BBR which has a sequence which is complementary to a ½ BBR sequence in a PNA or another BNA and which is capable of forming, under hybridizing conditions, a hybrid, BBR, with the PNA;

(b) an OSA which is not an attached support or indicator, or is an attached support or indicator selected from the group consisting of beads, polymers, proteins, peptides, surfaces, and indicators; and (c) additional hybridization sites, ½ BBRs, for hybridization with additional BNAs so as to form a BNA polymer;

wherein said BBR is capable of binding with high affinity to said BBA.

8. The method of claim 7 wherein a Hairpin Nucleic Acid (HNA) is used to terminate polymerization of BNAs, wherein said HNA under hybridizing conditions is capable of forming a hairpin while at the same time having a single-stranded sequence, ½ BBR, which is capable of binding to a BNA to form a BBR capable of binding a BBA with high affinity.

9. The method of claim 6 wherein said TBR is a nucleic acid binding protein recognition site.

10. The method of claim 9 wherein the TBR is a nucleic acid binding protein recognition site present in the genome of a pathogen or is a binding site associated with a pathogenic condition in a vertebrate genome.

11. The method of claim 9 wherein the TBR is the HIV-LTR or a portion thereof.

12. The method of claim 6 for detecting a specific TNA sequence, comprising the steps of:

(a) hybridizing said TNA with said PNA to form a TBR;

(b) hybridizing said PNA with a BNA containing a ½ BBR whose sequence is complementary to a ½ BBR sequence in the PNA;

(c) contacting the product of step (b) containing a TBR and a BBR, with a TBA which binds to said TBR;

(d) adding BBAs to the mixture in step (c) wherein said BBA comprises:

(i) a molecule or assembly or a portion of a molecule or assembly which is capable of selectively binding to a BBR;

(ii) a detectible indicator; and (e) detecting signal produced by means of an indicator attached to the BBA, or the OSA attached to the PNA, or by a shift in migration mobility of the TNA upon electrophoretic separation, or by a combination of these means.

13. The method of claim 12 wherein said indicator is a protein, selected from the group consisting of enzymes capable of catalyzing reactions leading to production of colored reaction products; a radionuclide; and colored beads.

14. The method of claim 6 wherein the target binding assembly, TBA, which is a nucleic acid binding molecule or assembly which cooperates in and stabilizes the hybridization of the target nucleic acid, TNA, with a specific probe nucleic acid, PNA, or the booster binding assembly, BBA, which is a nucleic acid binding molecule or assembly which cooperates in and stabilizes the hybridization of the probe nucleic acid, PNA, with a booster nucleic acid, NBA, or the hybridization between a BNA and a BNA, comprises at least one nucleic acid recognition unit, and one or all of the molecules, sequences, or parts thereof selected from the group consisting of linker molecules or sequences, an assembly molecule or sequence, an asymmetry molecule or sequence, a nuclear localization signal sequence (NLS) and an OSA.

15. The method of claim 14 wherein the DNA recognition unit is selected from the group consisting of an NF-kB binding unit, an SP1 binding unit, a TATA binding unit, a human papillomavirus E2 binding unit, an HPV LTR binding unit, and an HIV LTR binding unit.

16. The method of claim 15 wherein the DNA recognition unit has the sequence selected from the group consisting of SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82, SEQ ID NO. 83, SEQ ID NO. 84, SEQ ID NO. 93, SEQ ID NO. 94, SEQ ID NO. 95, SEQ ID NO. 96, SEQ ID NO. 97, and SEQ ID NO. 98.

17. The method of claim 14 wherein the linker sequence is an oligopeptide which does not interfere with the DNA recognition function of the DNA recognition unit and which provides stability and control over the spacing of the DNA recognition unit from the remainder of the TBA.

18. The method of claim 17 wherein the linker sequence is an oligopeptide sequence from the interdomain primary sequence of a structural protein.

19. The method of claim 14 wherein the assembly sequence is an oligopeptide sequence which directs the folding and association of DNA recognition units.

20. The method of claim 19 wherein the assembly molecule or sequence is the bacteriophage lambda cro protein or the CI protein, or is a derivative thereof selected from the group consisting of SEQ ID NO. 104, SEQ ID NO. 105, SEQ ID NO. 106, SEQ ID NO. 107, and SEQ ID NO. 108.

21. The method of claim 14 wherein the asymmetry sequence directs the association of DNA recognition and assembly sequences in a predetermined order.

22. The method of claim 21 wherein the asymmetry molecule or sequence is insulin, gonadotropic hormone, FSH, HCG, LH, ACTH, or relaxin or a portion of any of these molecules capable of acting as an asymmetry molecule or sequence.

23. The method of claim 22 wherein the asymmetry sequence is selected from the group consisting of SEQ ID NO. 85, SEQ ID NO. 86, SEQ ID NO. 87, SEQ ID NO. 88, SEQ ID NO. 89, SEQ ID NO. 90, SEQ ID NO. 91, and SEQ ID NO. 92.

24. The method of claim 14 wherein the NLS is an oligopeptide which directs the migration and uptake of a protein or complex associated with said NLS into the nucleus of a cell.

25. The method of claim 24 wherein the NLS is selected from the group consisting of SEQ ID NO. 72 and SEQ ID NO. 103.

26. The method of claim 14 wherein the TBA is HIV Detect I–IV or HPV Detect I–IV.

27. The method of claim 14 wherein the TBA has a sequence selected from the group consisting of SEQ ID NO. 109, SEQ ID NO. 110, SEQ ID NO. 111, SEQ ID NO. 112, SEQ ID NO. 113, SEQ ID NO. 114, SEQ ID NO. 115, and SEQ ID NO. 116.

28. The method of claim 14 to bind a particular nucleic acid sequence in a target nucleic acid sample which comprises:
(a) fragmenting the nucleic acid in the target nucleic acid sample;
(b) contacting, under hybridizing conditions, the fragmented nucleic acid with a probe nucleic acid complementary to the particular nucleic acid sequence of interest, wherein said probe nucleic acid, upon hybridization with said particular nucleic acid sequence of interest forms a target binding region to which said TBA specifically binds.

29. The method of claim 28 wherein said probe nucleic acid, in addition to sequences complementary to said particular nucleic acid sequence of interest, also has additional sequences to which a booster nucleic acid can bind to form a booster binding site to which a labeled booster binding assembly can bind to provide a signal showing and amplifying the binding of the probe nucleic acid to the target nucleic acid sequence of interest.

30. The method of claim 28 further comprising the step of:
(c) monitoring the shift in mobility of nucleic acids in the target nucleic acid sample as a function of the size such that binding of the TBA to a particular fragment in the sample modifies the mobility of the fragment.

31. A diagnostic or forensic test kit for the detection in a sample of nucleic acid having a specific sequence composition, TNA, which comprises:
(a) a first nucleic acid probe, PNA, complementary to nucleic acid with said specific sequence composition, the presence of which is to be ascertained in a test sample, wherein said first nucleic acid probe, PNA, and said nucleic acid with said specific sequence composition, TNA, form, upon hybridization, a binding site, TBR, for a first nucleic binding molecule, assembly, or protein, TBA, and wherein said first nucleic acid probe, PNA, further comprises additional sequence complementary to a second nucleic acid probe, BNA;
(b) a first nucleic acid binding molecule, assembly, or protein, TBA, specific for the hybrid formed by hybridization of said first nucleic acid probe, PNA, and said nucleic acid with specific sequence composition, TNA, wherein said TBA is capable of binding to and stabilizing the probe-target hybrid in a sequence-specific manner, and further wherein the TBA is capable of discriminating between a hybrid formed by the probe and the target nucleic acid, and a hybrid having one or more mismatches formed by the probe and a closely related or unrelated sequence;

(c) a second nucleic acid probe, BNA, complementary to said additional sequence in said first nucleic acid probe, PNA, wherein, upon hybridization of said first and second nucleic acid probes, a binding site, BBR, for a second nucleic acid binding molecule, assembly, or protein, BBA, is formed; and (d) a second nucleic acid binding molecule, assembly, or protein, BBA, which binds specifically to the hybrid formed upon hybridization of said first nucleic acid probe, PNA, and said second nucleic acid probe, BNA, wherein said second nucleic acid binding molecule, assembly, or protein, BBA, is labeled with a detectable label.

32. The diagnostic or forensic test kit of claim 31 wherein said first nucleic acid probe is complementary to the HIV LTR, such that upon hybridization of said first nucleic acid probe with an HIV LTR, a binding site is formed for NF-kB or a subunit thereof, SP1, TATA binding protein, HIV-Detect I, II, III, or IV, or HIV-Lock.

33. The diagnostic or forensic test kit of claim 32 wherein said first DNA binding protein is NF-kB or a subunit thereof, SP1, TATA binding protein, HIV-Detect I, II, III, or IV, or HIV-Lock.

34. The diagnostic or forensic test kit of claim 33 wherein said first nucleic acid probe, in addition to being complementary to the HIV LTR, comprises a sequence encoding the bacteriophage lambda left or right operator and said second nucleic acid probe comprises sequences complementary to said bacteriophage lambda left or right operator sequences in said first nucleic acid probe, such that upon hybridization of said first and second nucleic acid probes, a binding site for the bacteriophage lambda CI repressor protein, the bacteriophage lambda cro protein or a derivative or homolog thereof, is formed.

35. The diagnostic or forensic test kit of claim 34 wherein said second DNA binding protein is the bacteriophage lambda CI repressor protein, the bacteriophage lambda cro protein or a derivative or homology thereof.

36. A method of differentially binding a nucleic acid binding molecule, assembly, or protein, TBA, to a nucleic acid sequence correlated with a pathogenic condition which comprises:

(a) selecting a particular configuration of nucleic acid binding molecule, assembly, or protein sequences, TNA, present in the nucleic acid sequence correlated with a pathogenic condition as a target sequence for designing a probe nucleic acid, PNA, which will hybridize to said TNA if present in a test sample, and further, ensuring that a binding site for an available nucleic acid binding molecule, assembly, or protein, TBA, is formed upon hybridization of said probe nucleic acid and said TNA;

(b) selecting a TBA as a nucleic acid binding molecule, assembly, or protein which specifically binds to the selected TNA, but which does not bind to sequences not correlated with said pathogenic condition, and provided that said TBA is capable of binding to and stabilizing the probe-target hybrid in a sequence specific manner, and further wherein the TBA is capable of discriminating between a hybrid formed by the probe and the target nucleic acid, and a hybrid having one or more mismatches formed by the probe and a closely related or unrelated sequence;

(c) hybridizing said PNA with a test sample suspected of containing said TNA;

(d) contacting said TBA with any TBR hybrids formed in step (b); and (e) detecting any binding of said TBA with said TBR hybrids.

37. The method of claim 4 comprising amplifying signal obtained through binding the PNA to the TNA which comprises binding BNAs to the PNA-TNA hybrid and binding labeled BBAs to the BBRs formed between the BNA and PNA and between successive BNAs.

38. The method of claim 14 which further comprises assembling a nucleic acid binding complex, TBA or BBA, which comprises using asymmetry sequences to direct the association or non-association of components of the nucleic acid binding complex.

39. The method of claim 14 which further comprises assembling a nucleic acid binding complex, TBA or BBA, which comprises using assembly sequences derived from bacteriophage lambda cro or CI to act as or assemble associated components of the nucleic acid binding complex.

40. The method of claim 14 wherein said TBA, said BBA, or both said TBA and said BBA is a multimeric molecule or assembly prepared by linking assembly, asymmetry, or piloting molecules, sequences, or subunits to be incorporated into said multimeric TBA or BBA, and recovering said multimeric TBA or BBA.

* * * * *

UNITED STATES PATENT AND TRADEMARK OFFICE
CERTIFICATE OF CORRECTION

PATENT NO.   : 5,871,902

DATED        : February 16, 1999

INVENTOR(S)  : Susan Weininger, Arthur M. Weininger

It is certified that error appears in the above-identified patent and that said Letters Patent is hereby corrected as shown below:

Column 4, line 15: "TNA Each" should read --TNA. Each--.

Column 9, line 24: "NA sequence" should read --TNA sequence--; and line 25: "INA-PNA" should read --TNA-PNA--.

Column 12, line 25: "HV LTR" should read --HIV LTR--.

Column 13, line 25: "FIGS. 2A through 2D" should read --Figures 2A-B--.

Column 19, line 19: "FIG. 3 (IVb)" should read --FIGS. 3A-B (IVb)--;

line 28: "FIG. 2a (IIIa)" should read --Figures 2A-B (IIIa)--;

line 39: "FIG. 2b (Ib," should read Figures 2C-D (Ib,--; and line 41: "FIG. 2b (Ic, IIIc" should read --Figures 2C-D (Ic, IIIc--.

Column 22, line 30: "50" should read --p50--.

Column 30, line 21: "BA-TNA-" should read --TBA-TNA- --.

UNITED STATES PATENT AND TRADEMARK OFFICE
CERTIFICATE OF CORRECTION

PATENT NO.   :   5,871,902
DATED        :   February 16, 1999
INVENTOR(S)  :   Susan Weininger, Arthur M. Weininger It is certified that error appears in the above-identified patent and that said Letters Patent is hereby corrected as shown below:

Column 33, line 53: "such sequences" should read --such sequence,--.

Column 35, line 5: "PNA-INA" should read --PNA-TNA--.

Column 41, line 17: "105 + 102 + 74" should read --105 + 99 + 102 + 74--.

Column 136, line 50: "offorming" should read --of forming--.

Signed and Sealed this

Sixteenth Day of November, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 117

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

T G G G G A T T C C  C C A                                           1 3

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO (i v) ANTI-SENSE: NO (x i) SEQUENCE DESCRIPTION: SEQ ID NO:2:

AAGGGACTTT CCC                                                                  13

(2) INFORMATION FOR SEQ ID NO:3:

(i) SEQUENCE CHARACTERISTICS:
    (A) LENGTH: 13 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:3:

AGGGGACTTT CCG                                                                  13

(2) INFORMATION FOR SEQ ID NO:4:

(i) SEQUENCE CHARACTERISTICS:
    (A) LENGTH: 15 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:4:

GCTGGGGACT TTCCA                                                                15

(2) INFORMATION FOR SEQ ID NO:5:

(i) SEQUENCE CHARACTERISTICS:
    (A) LENGTH: 15 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:5:

ACAAGGGACT TTCCG                                                                15

(2) INFORMATION FOR SEQ ID NO:6:

(i) SEQUENCE CHARACTERISTICS:
    (A) LENGTH: 13 base pairs
    (B) TYPE: nucleic acid
    (C) STRANDEDNESS: both
    (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:6:

```
CCGGGTTTTC CCC                                                                          13
```

( 2 ) INFORMATION FOR SEQ ID NO:7:

( i ) SEQUENCE CHARACTERISTICS:
     ( A ) LENGTH: 27 base pairs
     ( B ) TYPE: nucleic acid
     ( C ) STRANDEDNESS: both
     ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

```
AAGGGACTTT CCGCTGGGGA CTTTCCA                                                           27
```

( 2 ) INFORMATION FOR SEQ ID NO:8:

( i ) SEQUENCE CHARACTERISTICS:
     ( A ) LENGTH: 27 base pairs
     ( B ) TYPE: nucleic acid
     ( C ) STRANDEDNESS: both
     ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

```
AAGGGACTTT CCGCTGGGGA CTTTCCG                                                           27
```

( 2 ) INFORMATION FOR SEQ ID NO:9:

( i ) SEQUENCE CHARACTERISTICS:
     ( A ) LENGTH: 26 base pairs
     ( B ) TYPE: nucleic acid
     ( C ) STRANDEDNESS: both
     ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

```
GCTGGGGACT TTCCAGGGAG GCGTGG                                                            26
```

( 2 ) INFORMATION FOR SEQ ID NO:10:

( i ) SEQUENCE CHARACTERISTICS:
     ( A ) LENGTH: 26 base pairs
     ( B ) TYPE: nucleic acid
     ( C ) STRANDEDNESS: both
     ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

```
GCTGGGGACT TTCCAGGGGA GGTGTG                                                            26
```

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

GCTGGGGACT TTCCGGGGAG CGTGGC    26

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

GCTGGGGACT TTCCGGGGAG GCGCGG    26

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

GCTGGGGACT TTCCAGAGAG GCGTGG    26

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

GCTGGGGACT TTCCAGGGGA GGCGTG    26

( 2 ) INFORMATION FOR SEQ ID NO:15:

( i ) SEQUENCE CHARACTERISTICS:
        ( A ) LENGTH: 26 base pairs ( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

GCTGGGGACT TTCCAGGGAG GCGTGG 26

( 2 ) INFORMATION FOR SEQ ID NO:16:

( i ) SEQUENCE CHARACTERISTICS:
( A ) LENGTH: 26 base pairs
( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

GCTGGGGACT TTCCAGGGAG GCTGCC 26

( 2 ) INFORMATION FOR SEQ ID NO:17:

( i ) SEQUENCE CHARACTERISTICS:
( A ) LENGTH: 33 base pairs
( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

TTTCCAGGGA GGCGTGGCCT GGGCGGGACT GGG 33

( 2 ) INFORMATION FOR SEQ ID NO:18:

( i ) SEQUENCE CHARACTERISTICS:
( A ) LENGTH: 33 base pairs
( B ) TYPE: nucleic acid
( C ) STRANDEDNESS: both
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

CGTGGCCTGG GCGGGACTGG GGAGTGGCGT CCC 33

( 2 ) INFORMATION FOR SEQ ID NO:19:

( i ) SEQUENCE CHARACTERISTICS:
( A ) LENGTH: 45 base pairs
( B ) TYPE: nucleic acid
( C ) STRANDEDNESS: both
( D ) TOPOLOGY: linear (  i i  ) MOLECULE TYPE: cDNA (  i i i  ) HYPOTHETICAL: NO (  i v  ) ANTI-SENSE: NO (  x i  ) SEQUENCE DESCRIPTION: SEQ ID NO:19:

CTACAAGGGA CTTTCCGCTG GGGACTTTCC AGGGAGGCGT GGCCT                45

( 2 ) INFORMATION FOR SEQ ID NO:20:

( i ) SEQUENCE CHARACTERISTICS:
        ( A ) LENGTH: 46 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

CAGCAAGGGA CTTTCCGCTG GGGACTTTCC AGGGGAGGTG TGGCCT               46

( 2 ) INFORMATION FOR SEQ ID NO:21:

( i ) SEQUENCE CHARACTERISTICS:
        ( A ) LENGTH: 46 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

CATCAAGGGA CTTTCCGCTG GGGACTTTCC AGGGGAGGTG TGGCCT               46

( 2 ) INFORMATION FOR SEQ ID NO:22:

( i ) SEQUENCE CHARACTERISTICS:
        ( A ) LENGTH: 46 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

CAACAAGGGA CTTTCCGCTG GGGACTTTCC AGGGGAGGTG TGGCCT               46

( 2 ) INFORMATION FOR SEQ ID NO:23:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO (iv) ANTI-SENSE: NO (xi) SEQUENCE DESCRIPTION: SEQ ID NO:23:

CTACAAGGGA CTTTCCGCTG GGGACTTTCC AGGGAGGCGT GGCAT    45

(2) INFORMATION FOR SEQ ID NO:24:

(i) SEQUENCE CHARACTERISTICS:
        (A) LENGTH: 44 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

CTACAAGGGA CTTTCCGCTG GGGACTTTCC GGGGAGCGTG GCCT    44

(2) INFORMATION FOR SEQ ID NO:25:

(i) SEQUENCE CHARACTERISTICS:
        (A) LENGTH: 44 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

CTACAAGGGA CTTTCCGCTG GGGACTTTCC GGGGAGGCGC GGCT    44

(2) INFORMATION FOR SEQ ID NO:26:

(i) SEQUENCE CHARACTERISTICS:
        (A) LENGTH: 45 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

CTACAAGGGA CTTTCCGCTG GGGACTTTCC AGAGAGGCGT GGACT    45

(2) INFORMATION FOR SEQ ID NO:27:

(i) SEQUENCE CHARACTERISTICS:
        (A) LENGTH: 46 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

CTACAAGGGA CTTTCCGCTG GGGACTTTCC AGGGGAGGCG TGGACT 46

( 2 ) INFORMATION FOR SEQ ID NO:28:

( i ) SEQUENCE CHARACTERISTICS:
        ( A ) LENGTH: 46 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:28:

CTACAGGGGA CTTTCCGCTG GGGACTTTCC AGGGAGGCGT GGGGAG 46

( 2 ) INFORMATION FOR SEQ ID NO:29:

( i ) SEQUENCE CHARACTERISTICS:
        ( A ) LENGTH: 43 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:29:

CTACAGGGGA CTTTCCGCTG GGGACTTTCC AGGGAGGCTG CCT 43

( 2 ) INFORMATION FOR SEQ ID NO:30:

( i ) SEQUENCE CHARACTERISTICS:
        ( A ) LENGTH: 48 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:30:

CTTTCCGCTG GGGACTTTCC AGGGAGGCGT GGCCTGGGCG GGACTGGG 48

( 2 ) INFORMATION FOR SEQ ID NO:31:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:31:

TTTCCAGGGA GGCGTGGCCT GGGCGGGACT GGGGAGTGGC GTCCC 45

( 2 ) INFORMATION FOR SEQ ID NO:32:

( i ) SEQUENCE CHARACTERISTICS:
 ( A ) LENGTH: 59 base pairs
 ( B ) TYPE: nucleic acid
 ( C ) STRANDEDNESS: both
 ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:32:

CTACAAGGGA CTTTCCGCTG GGGACTTTCC AGGGAGGCGT GGCCTGGGCG GACTGGGG    59

( 2 ) INFORMATION FOR SEQ ID NO:33:

( i ) SEQUENCE CHARACTERISTICS:
  ( A ) LENGTH: 59 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:33:

TTTCCGCTGG GGACTTTCCA GGGAGGCGTG GCCTGGGCGG GACTGGGGAG TGGCGTCCC    59

( 2 ) INFORMATION FOR SEQ ID NO:34:

( i ) SEQUENCE CHARACTERISTICS:
  ( A ) LENGTH: 70 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:34:

CTACAAGGGA CTTTCCGCTG GGGACTTTCC AGGGAGGCGT GGCCTGGGCG GACTGGGGA    60

GTGGCGTCCC    70

( 2 ) INFORMATION FOR SEQ ID NO:35:

( i ) SEQUENCE CHARACTERISTICS:
  ( A ) LENGTH: 61 base pairs
  ( B ) TYPE: nucleic acid
  ( C ) STRANDEDNESS: both
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:35:

TATCACCGCC AGTGGTATTT ATGTCAACAC CGCCAGAGAT AATTTATCAC CGCAGATGGT    60

T    61

( 2 ) INFORMATION FOR SEQ ID NO:36:

( i ) SEQUENCE CHARACTERISTICS:
    ( A ) LENGTH: 64 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:36:

```
TATCACCGCA AGGGATAAAT ATCTAACACC GTGCGTGTTG ACTATTTTAC CTCTGGCGGT      60
GATA                                                                  64
```

( 2 ) INFORMATION FOR SEQ ID NO:37:

( i ) SEQUENCE CHARACTERISTICS:
        ( A ) LENGTH: 70 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:37:

```
CTACAAGGGA CTTTCCGCTG GGGACTTTCC AGGGAGGCGT GGCCTGGGCG GGACTGGGGA      60
GTGGCGTCCC                                                             70
```

( 2 ) INFORMATION FOR SEQ ID NO:38:

( i ) SEQUENCE CHARACTERISTICS:
        ( A ) LENGTH: 37 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:38:

```
CTACAAGGGA CTTTCCGCTG GGGACTTTCC AGGGAGG                               37
```

( 2 ) INFORMATION FOR SEQ ID NO:39:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:39:

```
CGGGACTGGG GAGTGGCGTC CC                                               22
```

( 2 ) INFORMATION FOR SEQ ID NO:40:

(i) SEQUENCE CHARACTERISTICS:
    (A) LENGTH: 103 base pairs
    (B) TYPE: nucleic acid
    (C) STRANDEDNESS: both
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:40:

```
CTACAAGGGA CTTTCCGCTG GGGACTTTCC AGGGAGGTAT CACCGCCAGT GGTATTTATG      60
TCAACACCGC CAGAGATAAT TTATCACCGC AGATGGTTCT GCA                      103
```

(2) INFORMATION FOR SEQ ID NO:41:

(i) SEQUENCE CHARACTERISTICS:
    (A) LENGTH: 62 base pairs
    (B) TYPE: nucleic acid
    (C) STRANDEDNESS: both
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:41:

```
GAACCATCTG CGGTGATAAA TTATCTCTGG CGGTGTTGAC ATAAATACCA CTGGCGGTGA      60
TA                                                                    62
```

(2) INFORMATION FOR SEQ ID NO:42:

(i) SEQUENCE CHARACTERISTICS:
    (A) LENGTH: 71 base pairs
    (B) TYPE: nucleic acid
    (C) STRANDEDNESS: both
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:42:

```
GATCCAACCA TCTGCGGTGA TAAATTATCT CTGGCGGTGT TGACATAAAT ACCACTGGCG      60
GTGATACTGC A                                                          71
```

(2) INFORMATION FOR SEQ ID NO:43:

(i) SEQUENCE CHARACTERISTICS:
    (A) LENGTH: 63 base pairs
    (B) TYPE: nucleic acid
    (C) STRANDEDNESS: both
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:43:

```
GTATCACCGC CAGTGGTATT TATGTCAACA CCGCCAGAGA TAATTTATCA CCGCAGATGG      60
```

TTG 63

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:44:

GATCCGGGGG GATACCCCCC G 21

(2) INFORMATION FOR SEQ ID NO:45:

(i) SEQUENCE CHARACTERISTICS:
        (A) LENGTH: 91 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:45:

CGGGACTGGG GAGTGGCGTC CCTATCACCG CAAGGGATAA ATATCTAACA CCGTGCGTGT 60

TGACTATTTT ACCTCTGGCG GTGATAGCAT G 91

(2) INFORMATION FOR SEQ ID NO:46:

(i) SEQUENCE CHARACTERISTICS:
        (A) LENGTH: 53 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:46:

CTAAGGGCGT AACCGAAATC GGTTGAACCG AAACCGGTTA GTATAAAAGC AGA 53

(2) INFORMATION FOR SEQ ID NO:47:

(i) SEQUENCE CHARACTERISTICS:
        (A) LENGTH: 54 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:47:

AAAAGGGAGT AACCGAAAAC GGTCGGGACC GAAAACGGTG TATATAAAAG ATGT 54

( 2 ) INFORMATION FOR SEQ ID NO:48:

( i ) SEQUENCE CHARACTERISTICS:
    ( A ) LENGTH: 54 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:48:

AGTAGGGTGT AACCGAAAGC GGTTCAACCG AAAACGGTGC ATATATAAAG CAAA    5 4

( 2 ) INFORMATION FOR SEQ ID NO:49:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:49:

GCTTCAACCG AATTCGGTTG CATG    2 4

( 2 ) INFORMATION FOR SEQ ID NO:50:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:50:

TGTGCAACCG ATTTCGGTTG CCTT    2 4

( 2 ) INFORMATION FOR SEQ ID NO:51:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:51:

TATGCAACCG AAATAGGTTG GGCA    2 4

( 2 ) INFORMATION FOR SEQ ID NO:52:

( i ) SEQUENCE CHARACTERISTICS:

( A ) LENGTH: 24 base pairs
                ( B ) TYPE: nucleic acid
                ( C ) STRANDEDNESS: both
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:52:

TGCCTAACCG TTTTCGGTTA CTTG    24

( 2 ) INFORMATION FOR SEQ ID NO:53:

( i ) SEQUENCE CHARACTERISTICS:
                ( A ) LENGTH: 24 base pairs
                ( B ) TYPE: nucleic acid
                ( C ) STRANDEDNESS: both
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:53:

GGACTAACCG TTTTAGGTCA TATT    24

( 2 ) INFORMATION FOR SEQ ID NO:54:

( i ) SEQUENCE CHARACTERISTICS:
                ( A ) LENGTH: 52 base pairs
                ( B ) TYPE: nucleic acid
                ( C ) STRANDEDNESS: both
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:54:

GACGACTATC CAGCGACCAA GATCAGAGCC AGACACCGGA AACCCTGCC AC    52

( 2 ) INFORMATION FOR SEQ ID NO:55:

( i ) SEQUENCE CHARACTERISTICS:
                ( A ) LENGTH: 53 base pairs
                ( B ) TYPE: nucleic acid
                ( C ) STRANDEDNESS: both
                ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:55:

GACGACACGG TATCCGCTAC TCAGCTTGTT AAACAGCTAC AGCACACCCC CTC    53

( 2 ) INFORMATION FOR SEQ ID NO:56:

( i ) SEQUENCE CHARACTERISTICS:
                ( A ) LENGTH: 60 base pairs
                ( B ) TYPE: nucleic acid
                ( C ) STRANDEDNESS: both
                ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:56:

GACGACGACC TGCAGACACC ACAGACACCG CCCAGCCCCT TACAAAGCTG TTCTGTGCAG    60

(2) INFORMATION FOR SEQ ID NO:57:

(i) SEQUENCE CHARACTERISTICS:
        (A) LENGTH: 68 base pairs
        (B) TYPE: nucleic acid
        (C) STRANDEDNESS: both
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:57:

CATACCAAAG CCGTCGCCTT GGGCACCGAA GAAACACAAC CACTAAGTTG TTGCACAGAG    60

ACTCAGTG    68

(2) INFORMATION FOR SEQ ID NO:58:

(i) SEQUENCE CHARACTERISTICS:
        (A) LENGTH: 77 base pairs
        (B) TYPE: nucleic acid
        (C) STRANDEDNESS: both
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:58:

TAATGTAATT GATTGTAATG ACTCTATGTG CAGTACCAGT ACCGTATTCC AGCACCGTGT    60

CCGTGGGCAC CGCAAAG    77

(2) INFORMATION FOR SEQ ID NO:59:

(i) SEQUENCE CHARACTERISTICS:
        (A) LENGTH: 80 base pairs
        (B) TYPE: nucleic acid
        (C) STRANDEDNESS: both
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:59:

ACAGACAACG ATAACCGACC ACCACAAGCA GCGGCCAAAC ACCCGCCTT GGACAATAGA    60

ACAGCACGTA CTGCAACTAA    80

(2) INFORMATION FOR SEQ ID NO:60:

(i) SEQUENCE CHARACTERISTICS:
        (A) LENGTH: 266 base pairs
        (B) TYPE: nucleic acid (C) STRANDEDNESS: both
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:60:

| | | | | | |
|---|---|---|---|---|---|
| CATATGCAAT | ACAATGCATT | ATACAAACTG | GACACATATA | TATATTTGTG | AAGAAGCATC | 60 |
| AGTAACTGTG | GTAGAGGGTC | AAGTTGACTA | TTATGGTTTA | TATTATGTTC | ATGAAGGAAT | 120 |
| ACGAACATAT | TTTGTGCAGT | TTAAAGATGA | TGCAGAAAAA | TATAGTAAAA | ATAAAGTATG | 180 |
| GGAAGTTCAT | GCGGGTGGTC | AGGTAATATT | ATGTCCTACA | TCTGTGTTTA | GCAGCAACGA | 240 |
| AGTATCCTCT | CCTGAAATTA | TTAGGC | | | | 266 |

(2) INFORMATION FOR SEQ ID NO:61:

(i) SEQUENCE CHARACTERISTICS:
(A) LENGTH: 95 base pairs
(B) TYPE: nucleic acid
(C) STRANDEDNESS: both
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:61:

| | | | | | |
|---|---|---|---|---|---|
| AGGATGTATA | AAAAACATG | GATATACAGT | GGAAGTGCAG | TTTGATGGAG | ACATATGCTA | 60 |
| TTAGGCAGCA | CTTGGCCAAC | CACCCCGCCG | CGACC | | | 95 |

(2) INFORMATION FOR SEQ ID NO:62:

(i) SEQUENCE CHARACTERISTICS:
(A) LENGTH: 81 base pairs
(B) TYPE: nucleic acid
(C) STRANDEDNESS: both
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:62:

| | | | | | |
|---|---|---|---|---|---|
| CATGTTTTTT | TATACATCCA | TATCACCGCC | AGTGGTATTT | ATGTCAACAC | CGCCAGAGAT | 60 |
| AATTTATCAC | CGCAGATGGT | T | | | | 81 |

(2) INFORMATION FOR SEQ ID NO:63:

(i) SEQUENCE CHARACTERISTICS:
(A) LENGTH: 322 amino acids
(B) TYPE: amino acid
(D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:63:

```
Met  Ala  Asp  Asp  Asp  Pro  Tyr  Gly  Thr  Gly  Gln  Met  Phe  His  Leu  Asn
 1              5                   10                          15

Thr  Ala  Leu  Thr  His  Ser  Ile  Phe  Asn  Ala  Glu  Leu  Tyr  Ser  Pro  Glu
               20                   25                          30

Ile  Pro  Leu  Ser  Thr  Asp  Gly  Pro  Tyr  Leu  Gln  Ile  Leu  Glu  Gln  Pro
          35                        40                    45

Lys  Gln  Arg  Gly  Phe  Arg  Phe  Arg  Tyr  Val  Cys  Glu  Gly  Pro  Ser  His
     50                        55                    60

Gly  Gly  Leu  Pro  Gly  Ala  Ser  Ser  Glu  Lys  Asn  Lys  Lys  Ser  Tyr  Pro
 65                 70                        75                          80

Gln  Val  Lys  Ile  Cys  Asn  Tyr  Val  Gly  Pro  Ala  Lys  Val  Ile  Val  Gln
                85                       90                              95

Leu  Val  Thr  Asn  Gly  Lys  Asn  Ile  His  Leu  His  Ala  His  Ser  Leu  Val
               100                 105                     110

Gly  Lys  His  Cys  Glu  Asp  Gly  Val  Cys  Thr  Val  Thr  Ala  Gly  Pro  Lys
          115                      120                     125

Asp  Met  Val  Val  Gly  Phe  Ala  Asn  Leu  Gly  Ile  Leu  His  Val  Thr  Lys
     130                      135                     140

Lys  Lys  Val  Phe  Glu  Thr  Leu  Glu  Ala  Arg  Met  Thr  Glu  Ala  Cys  Ile
145                      150                     155                          160

Arg  Gly  Tyr  Asn  Pro  Gly  Leu  Leu  Val  His  Ser  Asp  Leu  Ala  Tyr  Leu
                    165                      170                          175

Gln  Ala  Glu  Gly  Gly  Gly  Asp  Arg  Gln  Leu  Thr  Asp  Arg  Glu  Lys  Glu
               180                      185                          190

Ile  Ile  Arg  Gln  Ala  Ala  Val  Gln  Gln  Thr  Lys  Glu  Met  Asp  Leu  Ser
          195                      200                     205

Val  Val  Arg  Leu  Met  Phe  Thr  Ala  Phe  Leu  Pro  Asp  Ser  Thr  Gly  Ser
     210                      215                     220

Phe  Thr  Arg  Arg  Leu  Glu  Pro  Val  Val  Ser  Asp  Ala  Ile  Tyr  Asp  Ser
225                      230                     235                          240

Lys  Ala  Pro  Asn  Ala  Ser  Asn  Leu  Lys  Ile  Val  Arg  Met  Asp  Arg  Thr
                    245                      250                          255

Ala  Gly  Cys  Val  Thr  Gly  Gly  Glu  Glu  Ile  Tyr  Leu  Leu  Cys  Asp  Lys
               260                      265                          270

Val  Gln  Lys  Asp  Asp  Ile  Gln  Ile  Arg  Phe  Tyr  Glu  Glu  Glu  Glu  Asn
          275                      280                     285

Gly  Gly  Val  Trp  Glu  Gly  Phe  Gly  Asp  Phe  Ser  Pro  Thr  Asp  Val  His
     290                      295                     300

Arg  Gln  Phe  Ala  Ile  Val  Phe  Lys  Thr  Pro  Lys  Tyr  Lys  Asp  Val  Asn
305                      310                     315                          320

Ile  Thr
```

( 2 ) INFORMATION FOR SEQ ID NO:64:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:64:

```
Met  Ala  Glu  Asp  Asp  Pro  Tyr  Leu  Gly  Arg  Pro  Glu  Gln  Met  Phe  His
 1              5                        10                       15

Leu  Asp  Pro  Ser  Leu  Thr  His  Thr  Ile  Phe  Asn  Pro  Glu  Val  Phe  Gln
              20                        25                       30

Pro  Gln  Met  Ala  Leu  Pro  Thr  Ala  Asp  Gly  Pro  Tyr  Leu  Gln  Ile  Leu
         35                        40                       45

Glu  Gln  Pro  Lys  Gln  Arg  Gly  Phe  Arg  Phe  Arg  Tyr  Val  Cys  Glu  Gly
     50                        55                       60

Pro  Ser  His  Gly  Gly  Leu  Pro  Gly  Ala  Ser  Ser  Glu  Lys  Asn  Lys  Lys
65                       70                       75                            80

Ser  Tyr  Pro  Gln  Val  Lys  Ile  Cys  Asn  Tyr  Val  Gly  Pro  Ala  Lys  Val
                    85                       90                       95

Ile  Val  Gln  Leu  Val  Thr  Asn  Gly  Lys  Asn  Ile  His  Leu  His  Ala  His
               100                      105                      110

Ser  Leu  Val  Gly  Lys  His  Cys  Glu  Asp  Gly  Ile  Cys  Thr  Val  Thr  Ala
          115                      120                      125

Gly  Pro  Glu  Asp  Cys  Val  His  Gly  Phe  Ala  Asn  Leu  Gly  Ile  Leu  His
     130                      135                      140

Val  Thr  Lys  Lys  Lys  Val  Phe  Glu  Thr  Leu  Glu  Ala  Arg  Met  Thr  Glu
145                      150                      155                           160

Ala  Cys  Ile  Arg  Gly  Tyr  Asn  Pro  Gly  Leu  Leu  Val  His  Pro  Asp  Leu
               165                      170                      175

Ala  Tyr  Leu  Gln  Ala  Glu  Gly  Gly  Gly  Asp  Arg  Gln  Leu  Gly  Asp  Arg
               180                      185                      190

Glu  Lys  Glu  Leu  Ile  Arg  Gln  Ala  Ala  Leu  Gln  Gln  Thr  Lys  Glu  Met
          195                      200                      205

Asp  Leu  Ser  Val  Val  Arg  Leu  Met  Phe  Thr  Ala  Phe  Leu  Pro  Asp  Ser
     210                      215                      220

Thr  Gly  Ser  Phe  Thr  Arg  Arg  Leu  Glu  Pro  Val  Val  Ser  Asp  Ala  Ile
225                      230                      235                           240

Tyr  Asp  Ser  Lys  Ala  Pro  Asn  Ala  Ser  Asn  Leu  Lys  Ile  Val  Arg  Met
               245                      250                      255

Asp  Arg  Thr  Ala  Gly  Cys  Val  Thr  Gly  Gly  Glu  Glu  Ile  Tyr  Leu  Leu
               260                      265                      270

Cys  Asp  Lys  Val  Gln  Lys  Asp  Ile  Gln  Ile  Arg  Phe  Tyr  Glu  Glu
          275                      280                      285

Glu  Glu  Asn  Gly  Gly  Val  Trp  Glu  Gly  Phe  Gly  Asp  Phe  Ser  Pro  Thr
     290                      295                      300

Asp  Val  His  Arg  Gln  Phe  Ala  Ile  Val  Phe  Lys  Thr  Pro  Lys  Tyr  Lys
305                      310                      315                           320

Asp  Ile  Asn  Ile  Thr
                    325
```

(2) INFORMATION FOR SEQ ID NO:65:

(i) SEQUENCE CHARACTERISTICS:
        (A) LENGTH: 268 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal ( x i ) SEQUENCE DESCRIPTION: SEQ ID NO:65:

| Met | Glu | Pro | Ala | Asp | Leu | Leu | Pro | Leu | Tyr | Leu | Gln | Pro | Glu | Trp | Gly |
|---|---|---|---|---|---|---|---|---|---|---|---|---|---|---|---|
| 1 | | | | 5 | | | | | 10 | | | | | 15 | |
| Glu | Gln | Glu | Pro | Gly | Gly | Ala | Thr | Pro | Phe | Val | Glu | Ile | Leu | Glu | Gln |
| | | | 20 | | | | | 25 | | | | | 30 | | |
| Pro | Lys | Gln | Arg | Gly | Met | Arg | Phe | Arg | Tyr | Lys | Cys | Glu | Gly | Arg | Ser |
| | | 35 | | | | | 40 | | | | | 45 | | | |
| Ala | Gly | Ser | Ile | Pro | Gly | Glu | His | Ser | Thr | Asp | Ser | Ala | Arg | Thr | His |
| | 50 | | | | | 55 | | | | 60 | | | | | |
| Pro | Thr | Ile | Arg | Val | Asn | His | Tyr | Arg | Gly | Pro | Gly | Arg | Val | Arg | Val |
| 65 | | | | | 70 | | | | | 75 | | | | | 80 |
| Ser | Leu | Val | Thr | Lys | Asp | Pro | Pro | His | Gly | Pro | His | Pro | His | Glu | Leu |
| | | | | 85 | | | | | 90 | | | | | 95 | |
| Val | Gly | Arg | His | Cys | Gln | His | Gly | Tyr | Tyr | Glu | Ala | Glu | Leu | Ser | Pro |
| | | | 100 | | | | | | 105 | | | | | 110 | |
| Asp | Arg | Ser | Ile | His | Ser | Phe | Gln | Asn | Leu | Gly | Ile | Gln | Cys | Val | Lys |
| | | | 115 | | | | | 120 | | | | | 125 | | |
| Lys | Arg | Glu | Leu | Glu | Ala | Ala | Val | Ala | Glu | Arg | Ile | Arg | Thr | Asn | Asn |
| | | 130 | | | | | 135 | | | | | 140 | | | |
| Asn | Pro | Phe | Asn | Val | Pro | Met | Glu | Glu | Arg | Gly | Ala | Glu | Tyr | Asp | Leu |
| 145 | | | | | 150 | | | | | 155 | | | | | 160 |
| Ser | Ala | Val | Arg | Leu | Cys | Phe | Gln | Val | Trp | Val | Asn | Gly | Pro | Gly | Gly |
| | | | | 165 | | | | | 170 | | | | | 175 | |
| Leu | Cys | Pro | Leu | Pro | Pro | Val | Leu | Ser | Gln | Pro | Ile | Tyr | Asp | Asn | Arg |
| | | | 180 | | | | | 185 | | | | | 190 | | |
| Ala | Pro | Ser | Thr | Ala | Glu | Leu | Arg | Ile | Leu | Pro | Gly | Asp | Arg | Asn | Ser |
| | | | 195 | | | | | 200 | | | | | 205 | | |
| Gly | Ser | Cys | Gln | Gly | Gly | Asp | Glu | Ile | Phe | Leu | Leu | Cys | Asp | Lys | Val |
| | | 210 | | | | | 215 | | | | | 220 | | | |
| Gln | Lys | Glu | Asp | Ile | Glu | Val | Arg | Phe | Trp | Ala | Glu | Gly | Trp | Glu | Ala |
| 225 | | | | | 230 | | | | | 235 | | | | | 240 |
| Lys | Gly | Ser | Phe | Ala | Ala | Ala | Asp | Val | His | Arg | Gln | Val | Ala | Ile | Val |
| | | | | 245 | | | | | 250 | | | | | 255 | |
| Phe | Arg | Thr | Pro | Pro | Phe | Arg | Glu | Arg | Ser | Leu | Arg | | | | |
| | | | 260 | | | | | 265 | | | | | | | |

( 2 ) INFORMATION FOR SEQ ID NO:66:

( i ) SEQUENCE CHARACTERISTICS:
    ( A ) LENGTH: 263 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:66:

| Met | Asp | Asp | Leu | Phe | Pro | Leu | Ile | Phe | Pro | Ser | Glu | Pro | Ala | Gln | Ala |
|---|---|---|---|---|---|---|---|---|---|---|---|---|---|---|---|
| 1 | | | | 5 | | | | | 10 | | | | | 15 | |
| Ser | Gly | Pro | Tyr | Val | Glu | Ile | Ile | Glu | Gln | Pro | Lys | Gln | Arg | Gly | Met |
| | | | 20 | | | | | 25 | | | | | 30 | | |
| Arg | Phe | Arg | Tyr | Lys | Cys | Glu | Gly | Arg | Ser | Ala | Gly | Ser | Ile | Pro | Gly |
| | | 35 | | | | | 40 | | | | | 45 | | | |

| | | | | | | | | | | | | | | |
|---|---|---|---|---|---|---|---|---|---|---|---|---|---|---|
| Glu | Arg | Ser | Thr | Asp | Thr | Thr | Lys | Thr | His | Pro | Thr | Ile | Lys | Ile | Asn |
| | 50 | | | | | 55 | | | | | 60 | | | | |
| Gly | Tyr | Thr | Gly | Pro | Gly | Thr | Val | Arg | Ile | Ser | Leu | Val | Thr | Lys | Asp |
| 65 | | | | | 70 | | | | | 75 | | | | | 80 |
| Pro | Pro | His | Arg | Pro | His | Pro | His | Glu | Leu | Val | Gly | Lys | Asp | Cys | Arg |
| | | | | 85 | | | | | 90 | | | | | 95 | |
| Asp | Gly | Tyr | Tyr | Glu | Ala | Asp | Leu | Cys | Pro | Asp | Arg | Ser | Ile | His | Ser |
| | | | 100 | | | | | 105 | | | | | 110 | | |
| Phe | Gln | Asn | Leu | Gly | Ile | Gln | Cys | Val | Lys | Lys | Arg | Asp | Leu | Glu | Gln |
| | | 115 | | | | | 120 | | | | | 125 | | | |
| Ala | Ile | Ser | Gln | Arg | Ile | Gln | Thr | Asn | Asn | Asn | Pro | Phe | His | Val | Pro |
| | 130 | | | | | 135 | | | | | 140 | | | | |
| Ile | Glu | Glu | Gln | Arg | Gly | Asp | Tyr | Asp | Leu | Asn | Ala | Val | Arg | Leu | Cys |
| 145 | | | | | 150 | | | | | 155 | | | | | 160 |
| Phe | Gln | Val | Thr | Val | Arg | Asp | Pro | Ala | Gly | Arg | Pro | Leu | Leu | Leu | Thr |
| | | | | 165 | | | | | 170 | | | | | 175 | |
| Pro | Val | Leu | Ser | His | Pro | Ile | Phe | Asp | Asn | Arg | Ala | Pro | Asn | Thr | Ala |
| | | | 180 | | | | | 185 | | | | | 190 | | |
| Glu | Leu | Lys | Ile | Cys | Arg | Val | Asn | Arg | Asn | Ser | Gly | Ser | Cys | Leu | Gly |
| | | 195 | | | | | 200 | | | | | 205 | | | |
| Gly | Asp | Glu | Ile | Phe | Leu | Leu | Cys | Asp | Lys | Val | Gln | Lys | Glu | Asp | Ile |
| | 210 | | | | | 215 | | | | | 220 | | | | |
| Glu | Val | Tyr | Phe | Thr | Gly | Pro | Gly | Trp | Glu | Ala | Arg | Gly | Ser | Phe | Ser |
| 225 | | | | | 230 | | | | | 235 | | | | | 240 |
| Gln | Ala | Asp | Val | His | Arg | Gln | Val | Ala | Ile | Val | Phe | Arg | Thr | Pro | Pro |
| | | | | 245 | | | | | 250 | | | | | 255 | |
| Tyr | Ala | Asp | Pro | Ser | Leu | Gln | | | | | | | | | |
| | | | 260 | | | | | | | | | | | | |

(2) INFORMATION FOR SEQ ID NO:67:

(i) SEQUENCE CHARACTERISTICS:
        (A) LENGTH: 263 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:67:

| | | | | | | | | | | | | | | | |
|---|---|---|---|---|---|---|---|---|---|---|---|---|---|---|---|
| Met | Asp | Glu | Leu | Phe | Pro | Leu | Ile | Phe | Pro | Ala | Glu | Pro | Ala | Gln | Ala |
| 1 | | | | 5 | | | | | 10 | | | | | 15 | |
| Ser | Gly | Pro | Tyr | Val | Glu | Ile | Ile | Glu | Gln | Pro | Lys | Gln | Arg | Gly | Met |
| | | | 20 | | | | | 25 | | | | | 30 | | |
| Arg | Phe | Arg | Tyr | Lys | Cys | Glu | Gly | Arg | Ser | Ala | Gly | Ser | Ile | Pro | Gly |
| | | 35 | | | | | 40 | | | | | 45 | | | |
| Glu | Arg | Ser | Thr | Asp | Thr | Thr | Lys | Thr | His | Pro | Thr | Ile | Lys | Ile | Asn |
| | 50 | | | | | 55 | | | | | 60 | | | | |
| Gly | Tyr | Thr | Gly | Pro | Gly | Thr | Val | Arg | Ile | Ser | Leu | Val | Thr | Lys | Asp |
| 65 | | | | | 70 | | | | | 75 | | | | | 80 |
| Pro | Pro | His | Arg | Pro | His | Pro | His | Glu | Leu | Val | Gly | Lys | Asp | Cys | Arg |
| | | | | 85 | | | | | 90 | | | | | 95 | |
| Asp | Gly | Phe | Tyr | Glu | Ala | Glu | Leu | Cys | Pro | Asp | Arg | Cys | Ile | His | Ser |
| | | | 100 | | | | | 105 | | | | | 110 | | |

|     |     |     |     |     |     |     |     |     |     |     |     |     |     |     |
|---|---|---|---|---|---|---|---|---|---|---|---|---|---|---|
| Phe | Gln | Asn<br>115 | Leu | Gly | Ile | Gln | Cys<br>120 | Val | Lys | Lys | Arg | Asp<br>125 | Leu | Glu | Gln |
| Ala | Ile<br>130 | Ser | Gln | Arg | Ile | Gln<br>135 | Thr | Asn | Asn | Asn | Pro<br>140 | Phe | Gln | Val | Pro |
| Ile<br>145 | Glu | Glu | Gln | Arg | Gly<br>150 | Asp | Tyr | Asp | Leu | Asn<br>155 | Ala | Val | Arg | Leu | Cys<br>160 |
| Phe | Gln | Val | Thr | Val<br>165 | Arg | Asp | Pro | Ser | Gly<br>170 | Arg | Pro | Leu | Arg | Leu<br>175 | Pro |
| Pro | Val | Leu | Pro<br>180 | His | Pro | Ile | Phe | Asp<br>185 | Asn | Arg | Ala | Pro | Asn<br>190 | Thr | Ala |
| Glu | Leu | Lys<br>195 | Ile | Cys | Arg | Val | Asn<br>200 | Arg | Asn | Ser | Gly | Ser<br>205 | Cys | Leu | Gly |
| Gly | Asp<br>210 | Glu | Ile | Phe | Leu | Leu<br>215 | Cys | Asp | Lys | Val | Gln<br>220 | Lys | Glu | Asp | Ile |
| Glu<br>225 | Val | Tyr | Phe | Thr | Gly<br>230 | Pro | Gly | Trp | Glu | Ala<br>235 | Arg | Gly | Ser | Phe | Ser<br>240 |
| Gln | Ala | Asp | Val | His<br>245 | Arg | Gln | Val | Ala | Ile<br>250 | Val | Phe | Arg | Thr | Pro<br>255 | Pro |
| Tyr | Ala | Asp | Pro<br>260 | Ser | Leu | Gln |  |  |  |  |  |  |  |  |  |

( 2 ) INFORMATION FOR SEQ ID NO:68:

( i ) SEQUENCE CHARACTERISTICS:
        ( A ) LENGTH: 299 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:68:

|     |     |     |     |     |     |     |     |     |     |     |     |     |     |     |     |
|---|---|---|---|---|---|---|---|---|---|---|---|---|---|---|---|
| Met<br>1 | Phe | Pro | Asn | Gln<br>5 | Asn | Asn | Gly | Ala | Ala<br>10 | Pro | Gly | Gln | Gly | Pro<br>15 | Ala |
| Val | Asp | Gly | Gln<br>20 | Gln | Ser | Leu | Asn | Tyr<br>25 | Asn | Gly | Leu | Pro | Ala<br>30 | Gln | Gln |
| Gln | Gln | Gln<br>35 | Leu | Ala | Gln | Ser | Thr<br>40 | Lys | Asn | Val | Arg | Lys<br>45 | Lys | Pro | Tyr |
| Val | Lys<br>50 | Ile | Thr | Glu | Gln | Pro<br>55 | Ala | Gly | Lys | Ala | Leu<br>60 | Arg | Phe | Arg | Tyr |
| Glu<br>65 | Cys | Glu | Gly | Arg | Ser<br>70 | Ala | Gly | Ser | Ile | Pro<br>75 | Gly | Val | Asn | Ser | Thr<br>80 |
| Pro | Glu | Asn | Lys | Thr<br>85 | Tyr | Pro | Thr | Ile | Glu<br>90 | Ile | Val | Gly | Tyr | Lys<br>95 | Gly |
| Arg | Ala | Val | Val<br>100 | Val | Val | Ser | Cys | Val<br>105 | Thr | Lys | Asp | Thr | Pro<br>110 | Tyr | Arg |
| Pro | His | Pro<br>115 | His | Asn | Leu | Val | Gly<br>120 | Lys | Glu | Gly | Cys | Lys<br>125 | Lys | Gly | Val |
| Cys | Thr<br>130 | Leu | Glu | Ile | Asn | Ser<br>135 | Glu | Thr | Met | Arg | Ala<br>140 | Val | Phe | Ser | Asn |
| Leu<br>145 | Gly | Ile | Gln | Cys | Val<br>150 | Lys | Lys | Lys | Asp | Ile<br>155 | Glu | Ala | Ala | Leu | Lys<br>160 |
| Ala | Arg | Glu | Glu | Ile | Arg | Val | Asp | Pro | Phe | Lys | Thr | Gly | Phe | Ser | His |

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Arg | Phe | Gln | Pro<br>180 | Ser | Ser | Ile | Asp | Leu | Asn<br>185 | Ser | Val | Arg | Leu<br>190 | Cys | Phe |
| Gln | Val | Phe<br>195 | Met | Glu | Ser | Glu | Gln<br>200 | Lys | Gly | Arg | Phe | Thr<br>205 | Ser | Pro | Leu |
| Pro | Pro<br>210 | Val | Val | Ser | Glu | Pro<br>215 | Ile | Phe | Asp | Lys | Lys<br>220 | Ala | Met | Ser | Asp |
| Leu<br>225 | Val | Ile | Cys | Arg | Leu<br>230 | Cys | Ser | Cys | Ser | Ala<br>235 | Thr | Val | Phe | Gly | Asn<br>240 |
| Thr | Gln | Ile | Ile | Leu<br>245 | Leu | Cys | Glu | Lys | Val<br>250 | Ala | Lys | Glu | Asp | Ile<br>255 | Ser |
| Val | Arg | Phe | Phe<br>260 | Glu | Glu | Lys | Asn | Gly<br>265 | Gln | Ser | Val | Trp | Glu<br>270 | Ala | Phe |
| Gly | Asp | Phe<br>275 | Gln | His | Thr | Asp | Val<br>280 | His | Lys | Gln | Thr | Ala<br>285 | Ile | Thr | Phe |
| Lys | Thr<br>290 | Pro | Arg | Tyr | His<br>295 | Thr | Leu | Asp | Ile | Thr |     |     |     |     |     |

( 2 ) INFORMATION FOR SEQ ID NO:69:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:69:

| Met<br>1 | Asp | Phe | Leu | Thr<br>5 | Asn | Leu | Arg | Phe | Thr<br>10 | Glu | Gly | Ile | Ser | Glu<br>15 | Pro |
| --- | --- | --- | --- | --- | --- | --- | --- | --- | --- | --- | --- | --- | --- | --- | --- |
| Tyr | Ile | Glu | Ile<br>20 | Phe | Glu | Gln | Pro | Arg<br>25 | Gln | Arg | Gly | Thr | Arg<br>30 | Phe | Arg |
| Tyr | Lys | Cys<br>35 | Glu | Gly | Arg | Ser | Ala<br>40 | Gly | Ser | Ile | Pro | Gly<br>45 | Glu | His | Ser |
| Thr | Asp<br>50 | Asn | Asn | Lys | Thr | Phe<br>55 | Pro | Ser | Ile | Gln | Ile<br>60 | Leu | Asn | Tyr | Phe |
| Gly<br>65 | Lys | Val | Lys | Ile | Arg<br>70 | Thr | Thr | Leu | Val | Thr<br>75 | Lys | Asn | Glu | Pro | Tyr<br>80 |
| Lys | Pro | His | Pro | His<br>85 | Asp | Leu | Val | Gly | Lys<br>90 | Gly | Cys | Arg | Asp | Gly<br>95 | Tyr |
| Tyr | Glu | Ala | Glu | Phe<br>100 | Gly | Pro | Glu | Arg | Gln<br>105 | Val | Leu | Ser | Phe | Gln<br>110 | Asn |
| Leu | Gly | Ile | Gln<br>115 | Cys | Val | Lys | Lys<br>120 | Lys | Asp | Leu | Lys | Glu<br>125 | Ser | Ile | Ser |
| Leu | Arg<br>130 | Ile | Ser | Lys | Lys | Asn<br>135 | Pro | Phe | Asn | Val | Pro<br>140 | Glu | Glu | Gln | Leu |
| His<br>145 | Asn | Ile | Asp | Glu | Tyr<br>150 | Asp | Leu | Asn | Val | Val<br>155 | Arg | Leu | Cys | Phe | Gln<br>160 |
| Ala | Phe | Leu | Pro | Asp<br>165 | Glu | His | Gly | Asn | Tyr<br>170 | Thr | Leu | Ala | Leu | Pro<br>175 | Pro |
| Leu | Ile | Ser | Asn<br>180 | Pro | Ile | Tyr | Asp | Asn<br>185 | Arg | Ala | Pro | Asn | Thr<br>190 | Ala | Glu |

```
Leu Arg Ile Cys Arg Val Asn Lys Asn Cys Gly Ser Val Lys Gly Gly
        195             200             205

Asp Glu Ile Phe Leu Leu Cys Asp Lys Val Gln Lys Asp Asp Ile Glu
    210             215             220

Val Arg Phe Val Leu Gly Asn Trp Glu Ala Lys Gly Ser Phe Ser Gln
225             230             235                         240

Ala Asp Val His Arg Gln Val Ala Ile Val Phe Arg Thr Pro Pro Phe
            245             250             255

Leu Gly Asp Ile Thr
            260
```

(2) INFORMATION FOR SEQ ID NO:70:

(i) SEQUENCE CHARACTERISTICS:
        (A) LENGTH: 262 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:70:

```
Met Asp Phe Leu Thr Asn Leu Arg Phe Thr Glu Gly Ile Ser Glu Pro
1               5                   10                  15

Tyr Ile Glu Ile Phe Glu Gln Pro Arg Gln Arg Gly Met Arg Phe Arg
            20              25              30

Tyr Lys Cys Glu Gly Arg Ser Ala Gly Ser Ile Pro Gly Glu His Ser
        35              40              45

Thr Asp Asn Asn Lys Thr Phe Pro Ser Ile Gln Ile Leu Asn Tyr Phe
    50              55              60

Gly Lys Val Lys Ile Arg Thr Thr Leu Val Thr Lys Asn Glu Pro Tyr
65              70              75                          80

Lys Pro His Pro His Asp Leu Val Gly Lys Gly Cys Arg Asp Gly Tyr
            85              90              95

Tyr Glu Ala Glu Phe Gly Pro Glu Arg Gln Val Leu Ser Phe Gln Asn
        100             105             110

Leu Gly Ile Gln Cys Val Lys Lys Lys Asp Leu Lys Glu Ser Ile Ser
        115             120             125

Leu Arg Ile Ser Lys Lys Ile Asn Pro Phe Asn Val Pro Glu Glu Gln
    130             135             140

Leu His Asn Ile Asp Glu Tyr Asp Leu Asn Val Val Arg Leu Cys Phe
145             150             155                         160

Gln Ala Phe Leu Pro Asp Glu His Gly Asn Tyr Thr Leu Ala Leu Pro
            165             170             175

Pro Leu Ile Ser Asn Pro Ile Tyr Asp Asn Arg Ala Pro Asn Thr Ala
        180             185             190

Glu Leu Arg Ile Cys Arg Val Asn Lys Asn Cys Gly Ser Val Lys Gly
        195             200             205

Gly Asp Glu Ile Phe Leu Leu Cys Asp Lys Val Gln Lys Asp Asp Ile
    210             215             220

Glu Val Arg Phe Val Leu Gly Asn Trp Glu Ala Lys Gly Ser Phe Ser
225             230             235                         240

Gln Ala Asp Val His Arg Gln Val Ala Ile Val Phe Arg Thr Pro Pro
            245             250             255
```

```
            Phe  Leu  Gly  Asp  Ile  Thr
                           260
```

( 2 ) INFORMATION FOR SEQ ID NO:71:

( i ) SEQUENCE CHARACTERISTICS:
        ( A ) LENGTH: 314 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:71:

```
Met  Ser  Asn  Lys  Lys  Gln  Ser  Asn  Arg  Leu  Thr  Glu  Gln  His  Lys  Leu
 1                   5                        10                       15

Ser  Gln  Gly  Val  Ile  Gly  Ile  Phe  Gly  Asp  Tyr  Ala  Lys  Ala  His  Asp
              20                       25                       30

Leu  Ala  Val  Gly  Glu  Val  Ser  Lys  Leu  Val  Lys  Lys  Ala  Leu  Ser  Asn
               35                   40                       45

Glu  Tyr  Pro  Gln  Leu  Ser  Phe  Arg  Tyr  Arg  Asp  Ser  Ile  Lys  Lys  Thr
      50                        55                       60

Glu  Ile  Asn  Glu  Ala  Leu  Lys  Lys  Ile  Asp  Pro  Asp  Leu  Gly  Gly  Thr
 65                        70                       75                       80

Leu  Phe  Val  Ser  Asn  Ser  Ser  Ile  Lys  Pro  Asp  Gly  Gly  Ile  Val  Glu
                    85                       90                       95

Val  Lys  Asp  Asp  Tyr  Gly  Glu  Trp  Arg  Val  Val  Leu  Val  Ala  Glu  Ala
               100                      105                      110

Lys  His  Gln  Gly  Lys  Asp  Ile  Ile  Asn  Ile  Arg  Asn  Gly  Leu  Leu  Val
               115                      120                      125

Gly  Lys  Arg  Gly  Asp  Gln  Asp  Leu  Met  Ala  Ala  Gly  Asn  Ala  Ile  Glu
      130                      135                      140

Arg  Ser  His  Asn  Ile  Ser  Glu  Ile  Ala  Asn  Phe  Met  Leu  Ser  Glu  Ser
145                       150                      155                      160

His  Phe  Pro  Tyr  Val  Leu  Phe  Leu  Glu  Gly  Ser  Asn  Phe  Leu  Thr  Glu
               165                      170                      175

Asn  Ile  Ser  Ile  Thr  Arg  Pro  Asp  Gly  Arg  Val  Val  Asn  Leu  Glu  Tyr
               180                      185                      190

Asn  Ser  Gly  Ser  Glu  Ser  His  Phe  Pro  Tyr  Val  Leu  Phe  Leu  Glu  Gly
          195                      200                      205

Ser  Asn  Phe  Leu  Thr  Glu  Asn  Ile  Ser  Ile  Thr  Arg  Pro  Asp  Gly  Arg
     210                      215                      220

Val  Val  Asn  Leu  Glu  Tyr  Asn  Ser  Gly  Ile  Leu  Asn  Arg  Leu  Asp  Arg
225                       230                      235                      240

Leu  Thr  Ala  Ala  Asn  Tyr  Gly  Met  Pro  Ile  Asn  Ser  Asn  Leu  Cys  Ile
                    245                      250                      255

Asn  Lys  Phe  Val  Asn  His  Lys  Asp  Lys  Ser  Ile  Met  Leu  Gln  Ala  Ala
               260                      265                      270

Ser  Ile  Tyr  Thr  Gln  Gly  Asp  Gly  Arg  Glu  Trp  Asp  Ser  Lys  Ile  Met
               275                      280                      285

Phe  Glu  Ile  Met  Phe  Asp  Ile  Ser  Thr  Thr  Ser  Leu  Arg  Val  Leu  Gly
      290                      295                      300

Arg  Asp  Leu  Phe  Glu  Gln  Leu  Thr  Ser  Lys
```

305 310

( 2 ) INFORMATION FOR SEQ ID NO:72:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:72:

```
Cys Asp Thr Asp Asp Arg His Arg Ile Glu Glu Lys Arg Lys Arg Lys
  1               5                   10                  15
Thr
```

( 2 ) INFORMATION FOR SEQ ID NO:73:

( i ) SEQUENCE CHARACTERISTICS:
        ( A ) LENGTH: 168 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:73:

```
Gly Asp Pro Gly Lys Lys Lys Gln His Ile Cys His Ile Gln Gly Cys
  1               5                   10                  15

Gly Lys Val Tyr Gly Lys Thr Ser His Leu Arg Ala His Leu Arg Trp
                 20                  25                  30

His Thr Gly Glu Arg Pro Phe Met Cys Thr Trp Ser Tyr Cys Gly Lys
             35                  40                  45

Arg Phe Thr Arg Ser Asp Glu Leu Gln Arg His Lys Arg Thr His Thr
         50                  55                  60

Gly Glu Lys Lys Phe Ala Cys Pro Glu Cys Pro Lys Arg Phe Met Arg
 65                  70                  75                  80

Ser Asp His Leu Ser Lys His Ile Lys Thr His Gln Asn Lys Lys Gly
                 85                  90                  95

Gly Pro Gly Val Ala Leu Ser Val Gly Thr Leu Pro Leu Asp Ser Gly
             100                 105                 110

Ala Gly Ser Glu Gly Ser Gly Thr Ala Thr Pro Ser Ala Leu Ile Thr
         115                 120                 125

Thr Asn Met Val Ala Met Glu Ala Ile Cys Pro Glu Gly Ile Ala Arg
    130                 135                 140

Leu Ala Asn Ser Gly Ile Asn Val Met Gln Val Ala Asp Leu Gln Ser
145                 150                 155                 160

Ile Asn Ile Ser Gly Asn Gly Phe
                 165
```

( 2 ) INFORMATION FOR SEQ ID NO:74:

( i ) SEQUENCE CHARACTERISTICS:

(A) LENGTH: 181 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:74:

| Ser | Gly | Ile | Val | Pro | Gln | Leu | Gln | Asn | Ile | Val | Ser | Thr | Val | Asn | Leu |
|---|---|---|---|---|---|---|---|---|---|---|---|---|---|---|---|
| 1 | | | | 5 | | | | | 10 | | | | | 15 | |
| Gly | Cys | Lys | Leu | Asp | Leu | Lys | Thr | Ile | Ala | Leu | Arg | Ala | Arg | Asn | Ala |
| | | | 20 | | | | 25 | | | | | 30 | | | |
| Glu | Tyr | Asn | Pro | Lys | Arg | Phe | Ala | Ala | Val | Ile | Met | Arg | Ile | Arg | Glu |
| | | 35 | | | | | 40 | | | | | 45 | | | |
| Pro | Arg | Thr | Thr | Ala | Leu | Ile | Phe | Ser | Ser | Gly | Lys | Met | Val | Cys | Thr |
| | 50 | | | | | 55 | | | | | 60 | | | | |
| Gly | Ala | Lys | Ser | Glu | Glu | Gln | Ser | Arg | Leu | Ala | Ala | Arg | Lys | Tyr | Ala |
| 65 | | | | | 70 | | | | | 75 | | | | | 80 |
| Arg | Val | Val | Gln | Lys | Leu | Gly | Phe | Pro | Ala | Lys | Phe | Leu | Asp | Phe | Lys |
| | | | | 85 | | | | | 90 | | | | | 95 | |
| Ile | Gln | Asn | Met | Val | Gly | Ser | Cys | Asp | Val | Lys | Phe | Pro | Ile | Arg | Leu |
| | | | 100 | | | | | 105 | | | | | 110 | | |
| Glu | Gly | Leu | Val | Leu | Thr | His | Gln | Gln | Phe | Ser | Ser | Tyr | Glu | Pro | Glu |
| | | 115 | | | | | 120 | | | | | 125 | | | |
| Leu | Phe | Pro | Gly | Leu | Ile | Tyr | Arg | Met | Ile | Lys | Pro | Arg | Ile | Val | Leu |
| | 130 | | | | | 135 | | | | | 140 | | | | |
| Leu | Ile | Phe | Val | Ser | Gly | Lys | Val | Val | Leu | Thr | Gly | Ala | Lys | Val | Arg |
| 145 | | | | | 150 | | | | | 155 | | | | | 160 |
| Ala | Glu | Ile | Tyr | Glu | Ala | Phe | Glu | Asn | Ile | Tyr | Pro | Ile | Leu | Lys | Gly |
| | | | | 165 | | | | | 170 | | | | | 175 | |
| Phe | Arg | Lys | Thr | Thr | | | | | | | | | | | |
| | | | 180 | | | | | | | | | | | | |

(2) INFORMATION FOR SEQ ID NO:75:

(i) SEQUENCE CHARACTERISTICS:
(A) LENGTH: 85 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:75:

| Ser | Cys | Phe | Ala | Leu | Ile | Ser | Gly | Thr | Ala | Asn | Gln | Val | Lys | Cys | Tyr |
|---|---|---|---|---|---|---|---|---|---|---|---|---|---|---|---|
| 1 | | | | 5 | | | | | 10 | | | | | 15 | |
| Arg | Phe | Arg | Val | Lys | Lys | Asn | His | Arg | His | Arg | Tyr | Glu | Asn | Cys | Thr |
| | | | 20 | | | | 25 | | | | | 30 | | | |
| Thr | Thr | Trp | Phe | Thr | Val | Ala | Asp | Asn | Gly | Ala | Glu | Arg | Gln | Gly | Gln |
| | | | 35 | | | | | 40 | | | | | 45 | | |
| Ala | Gln | Ile | Leu | Ile | Thr | Phe | Gly | Ser | Pro | Ser | Gln | Arg | Gln | Asp | Phe |
| | | 50 | | | | | 55 | | | | | 60 | | | |

```
        Leu  Lys  His  Val  Pro  Leu  Pro  Pro  Gly  Met  Asn  Ile  Ser  Gly  Phe  Thr
        65                  70                  75                            80

Ala  Ser  Leu  Asp  Phe
                             85
```

(2) INFORMATION FOR SEQ ID NO:76:

(i) SEQUENCE CHARACTERISTICS:
        (A) LENGTH: 87 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:76:

```
        Cys  Pro  Cys  Leu  Leu  Ile  Gly  Thr  Ser  Gly  Asn  Gly  Asn  Gln  Val  Lys
        1                    5                   10                            15

Cys  Tyr  Ser  Phe  Arg  Val  Lys  Arg  Trp  His  Asp  Arg  Asp  Lys  Tyr  His
                            20                  25                            30

His  Thr  Thr  Thr  Trp  Trp  Ala  Val  Gly  Gly  Gln  Gly  Ser  Glu  Arg  Pro
                       35                       40                  45

Gly  Asp  Ala  Thr  Val  Ile  Val  Thr  Phe  Lys  Asp  Gln  Ser  Gln  Arg  Ser
                  50                       55                       60

His  Phe  Leu  Gln  Gln  Val  Pro  Leu  Pro  Pro  Gly  Met  Ser  Ala  His  Gly
        65                       70                       75                       80

Val  Thr  Met  Thr  Val  Asp  Phe
                            85
```

(2) INFORMATION FOR SEQ ID NO:77:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:77:

```
        Pro  Pro  Val  Ile  Cys  Leu  Lys  Gly  Gly  His  Asn  Gln  Leu  Lys  Cys  Leu
        1                    5                       10                            15

Arg  Tyr  Arg  Leu  Lys  Ser  Lys  His  Ser  Ser  Leu  Phe  Asp  Cys  Ile  Ser
                            20                  25                            30

Thr  Thr  Trp  Ser  Trp  Val  Asp  Thr  Thr  Ser  Thr  Cys  Arg  Leu  Gly  Ser
                       35                       40                  45

Gly  Arg  Met  Leu  Ile  Lys  Phe  Ala  Asp  Ser  Glu  Gln  Arg  Asp  Lys  Phe
                  50                       55                       60

Leu  Ser  Arg  Val  Pro  Leu  Pro  Ser  Thr  Thr  Gln  Val  Phe  Leu  Gly  Asn
        65                       70                       75                       80

Phe  Tyr  Gly  Leu
```

(2) INFORMATION FOR SEQ ID NO:78:

( i ) SEQUENCE CHARACTERISTICS:
   ( A ) LENGTH: 84 amino acids
   ( B ) TYPE: amino acid
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:78:

```
Pro Pro Val Ile Leu Val Arg Gly Gly Ala Asn Thr Leu Lys Cys Phe
1               5                   10                  15

Arg Asn Arg Ala Arg Val Arg Tyr Arg Gly Leu Phe Lys Tyr Phe Ser
            20                  25                  30

Thr Thr Trp Ser Trp Val Ala Gly Asp Ser Thr Glu Arg Leu Gly Arg
            35              40                  45

Ser Arg Met Leu Ile Leu Phe Thr Ser Ala Cys Gln Arg Glu Lys Pro
        50              55                  60

Asp Glu Thr Val Lys Tyr Pro Lys Gly Val Asp Thr Ser Tyr Gly Asn
65                  70                  75                  80

Leu Asp Ser Leu
```

( 2 ) INFORMATION FOR SEQ ID NO:79:

( i ) SEQUENCE CHARACTERISTICS:
   ( A ) LENGTH: 84 amino acids
   ( B ) TYPE: amino acid
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:79:

```
Pro Pro Val Val Cys Val Lys Gly Gly Ala Asn Gln Leu Lys Cys Leu
1               5                   10                  15

Arg Tyr Arg Leu Lys Ala Ser Thr Gln Val Asp Phe Asp Ser Ile Ser
            20                  25                  30

Thr Thr Trp His Trp Thr Asp Arg Lys Asn Thr Glu Arg Ile Gly Ser
            35              40                  45

Ala Arg Met Leu Val Lys Phe Ile Asp Glu Ala Gln Arg Glu Lys Phe
        50              55                  60

Leu Glu Arg Val Ala Leu Pro Arg Ser Val Ser Val Phe Leu Gly Gln
65                  70                  75                  80

Phe Asn Gly Ser
```

( 2 ) INFORMATION FOR SEQ ID NO:80:

( i ) SEQUENCE CHARACTERISTICS:
   ( A ) LENGTH: 84 amino acids
   ( B ) TYPE: amino acid
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:80:

Thr Pro Ile Val Gln Leu Gln Gly Asp Ser Asn Cys Leu Lys Cys Phe
1               5                   10                  15

Arg Tyr Arg Leu Asn Asp Lys Tyr Lys His Leu Phe Glu Leu Ala Ser
                20                  25                  30

Ser Thr Trp His Trp Ala Ser Pro Glu Ala Pro His Lys Asn Ala Ile
            35                  40                  45

Val Thr Leu Thr Tyr Ser Ser Glu Glu Gln Arg Gln Gln Phe Leu Asn
        50                  55                  60

Ser Val Lys Ile Pro Pro Thr Ile Arg His Lys Val Gly Phe Met Ser
65                  70                  75                  80

Leu His Leu Leu ( 2 ) INFORMATION FOR SEQ ID NO:81:

( i ) SEQUENCE CHARACTERISTICS:
( A ) LENGTH: 84 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:81:

Thr Pro Ile Val Gln Phe Gln Gly Glu Ser Asn Cys Leu Lys Cys Phe
1               5                   10                  15

Arg Tyr Arg Leu Asn Arg Asp His Arg His Leu Phe Asp Leu Ile Ser
                20                  25                  30

Ser Thr Trp His Trp Ala Ser Ser Lys Ala Pro His Lys His Ala Ile
            35                  40                  45

Val Thr Val Thr Tyr Asp Ser Glu Glu Gln Arg Gln Gln Phe Leu Asp
        50                  55                  60

Val Val Lys Ile Pro Pro Thr Ile Ser His Lys Leu Gly Phe Met Ser
65                  70                  75                  80

Leu His Leu Leu ( 2 ) INFORMATION FOR SEQ ID NO:82:

( i ) SEQUENCE CHARACTERISTICS:
( A ) LENGTH: 80 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:82:

Thr Pro Ile Ile His Leu Lys Gly Asp Arg Asn Ser Leu Lys Cys Leu
1               5                   10                  15

Arg Tyr Arg Leu Arg Lys His Ser Asp His Tyr Arg Asp Ile Ser Ser
                20                  25                  30

-continued

```
Thr Trp His Trp Thr Gly Ala Gly Asn Glu Lys Thr Gly Ile Leu Thr
         35                  40                  45

Val Thr Tyr His Ser Glu Thr Gln Arg Thr Lys Phe Leu Asn Thr Val
     50                  55                  60

Ala Ile Pro Asp Ser Val Gln Ile Leu Val Gly Tyr Asn Thr Met Tyr
65                  70                  75                  80
```

(2) INFORMATION FOR SEQ ID NO:83:

(i) SEQUENCE CHARACTERISTICS:
        (A) LENGTH: 80 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:83:

```
Thr Pro Ile Val His Leu Lys Gly Asp Ala Asn Thr Leu Lys Cys Leu
1                5                  10                  15

Arg Tyr Arg Phe Lys Lys His Cys Thr Leu Tyr Thr Ala Val Ser Ser
             20                  25                  30

Thr Trp His Trp Thr Gly His Asn Tyr Lys His Lys Ser Ala Ile Val
         35                  40                  45

Thr Leu Thr Tyr Asp Ser Glu Trp Gln Arg Asp Gln Phe Leu Ser Gln
     50                  55                  60

Val Lys Ile Pro Lys Thr Ile Thr Val Ser Thr Gly Phe Met Ser Ile
65                  70                  75                  80
```

(2) INFORMATION FOR SEQ ID NO:84:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:84:

```
Ala Pro Ile Val His Leu Lys Gly Glu Ser Asn Ser Leu Lys Cys Leu
1                5                  10                  15

Arg Tyr Arg Leu Lys Pro Tyr Asn Glu Leu Tyr Ser Ser Met Ser Ser
             20                  25                  30

Thr Trp His Trp Thr Ser Asp Asn Lys Asn Ser Lys Asn Gly Ile Val
         35                  40                  45

Thr Val Thr Phe Val Thr Gly Gln Gln Gln Gln Met Phe Leu Gly Thr
     50                  55                  60

Val Lys Ile Pro Pro Thr Val Gln Ile Ser Thr Gly Phe Met Thr Leu
65                  70                  75                  80

Val
```

(2) INFORMATION FOR SEQ ID NO:85:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:85:

```
Gly Ile Val Glu Gln Cys Cys Thr Ser Ile Cys Ser Leu Tyr Gln Leu
1               5                   10                  15
Glu Asn Tyr Cys Asn
            20
```

( 2 ) INFORMATION FOR SEQ ID NO:86:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:86:

```
Phe Val Asn Gln His Leu Cys Gly Ser His Leu Val Glu Ala Leu Tyr
1               5                   10                  15
Leu Val Cys Gly Glu Arg Gly Phe Phe Tyr Thr Pro Lys Thr
            20                  25                  30
```

( 2 ) INFORMATION FOR SEQ ID NO:87:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:87:

```
Gly Ile Val Glu Gln Cys Cys Ala Ser Val Cys Ser Leu Tyr Gln Leu
1               5                   10                  15
Glu Asn Tyr Cys Asn
            20
```

( 2 ) INFORMATION FOR SEQ ID NO:88:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:88:

| Phe | Val | Asn | Gln | His | Leu | Cys | Gly | Ser | His | Leu | Val | Glu | Ala | Leu | Tyr |
|---|---|---|---|---|---|---|---|---|---|---|---|---|---|---|---|
| 1 | | | | 5 | | | | | 10 | | | | | 15 | |

| Leu | Val | Cys | Gly | Glu | Arg | Gly | Phe | Phe | Tyr | Thr | Pro | Lys | Thr |
|---|---|---|---|---|---|---|---|---|---|---|---|---|---|
| | | | 20 | | | | | 25 | | | | | 30 |

(2) INFORMATION FOR SEQ ID NO:89:

(i) SEQUENCE CHARACTERISTICS:
(A) LENGTH: 24 amino acids
(B) TYPE: amino acid
(D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:89:

| Gln | Leu | Tyr | Ser | Ala | Leu | Ala | Asn | Lys | Cys | Cys | His | Val | Gly | Cys | Ile |
|---|---|---|---|---|---|---|---|---|---|---|---|---|---|---|---|
| 1 | | | | 5 | | | | | 10 | | | | | 15 | |

| Lys | Arg | Ser | Leu | Ala | Arg | Phe | Cys |
|---|---|---|---|---|---|---|---|
| | | | 20 | | | | |

(2) INFORMATION FOR SEQ ID NO:90:

(i) SEQUENCE CHARACTERISTICS:
(A) LENGTH: 33 amino acids
(B) TYPE: amino acid
(D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:90:

| Asp | Ser | Trp | Met | Glu | Glu | Val | Ile | Lys | Ile | Cys | Gly | Arg | Glu | Leu | Val |
|---|---|---|---|---|---|---|---|---|---|---|---|---|---|---|---|
| 1 | | | | 5 | | | | | 10 | | | | | 15 | |

| Arg | Ala | Gln | Ile | Ala | Ile | Cys | Gly | Met | Ser | Thr | Trp | Ser | Lys | Arg | Ser |
|---|---|---|---|---|---|---|---|---|---|---|---|---|---|---|---|
| | | | 20 | | | | | 25 | | | | | 30 | | |

Leu (2) INFORMATION FOR SEQ ID NO:91:

(i) SEQUENCE CHARACTERISTICS:
(A) LENGTH: 24 amino acids
(B) TYPE: amino acid
(D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:91:

| Glu | Glu | Lys | Met | Gly | Thr | Ala | Lys | Lys | Cys | Cys | Ala | Ile | Gly | Cys | Ser |
|---|---|---|---|---|---|---|---|---|---|---|---|---|---|---|---|
| 1 | | | | 5 | | | | | 10 | | | | | 15 | |

| Thr | Glu | Asp | Phe | Arg | Met | Val | Cys |
|---|---|---|---|---|---|---|---|
| | | | 20 | | | | |

(2) INFORMATION FOR SEQ ID NO:92:

(i) SEQUENCE CHARACTERISTICS:
 (A) LENGTH: 40 amino acids
 (B) TYPE: amino acid
 (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:92:

| Arg | Pro | Asn | Trp | Glu | Glu | Arg | Ser | Arg | Leu | Cys | Gly | Arg | Asp | Leu | Ile |
|---|---|---|---|---|---|---|---|---|---|---|---|---|---|---|---|
| 1 | | | | 5 | | | | | 10 | | | | | 15 | |

| Arg | Ala | Phe | Ile | Tyr | Leu | Cys | Gly | Gly | Thr | Arg | Trp | Thr | Arg | Leu | Pro |
|---|---|---|---|---|---|---|---|---|---|---|---|---|---|---|---|
| | | | 20 | | | | | 25 | | | | | 30 | | |

| Asn | Phe | Gly | Asn | Tyr | Pro | Ile | Met |
|---|---|---|---|---|---|---|---|
| | | 35 | | | | | 40 |

(2) INFORMATION FOR SEQ ID NO:93:

(i) SEQUENCE CHARACTERISTICS:
 (A) LENGTH: 182 amino acids
 (B) TYPE: amino acid
 (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:93:

| Ser | Gly | Ile | Val | Pro | Thr | Leu | Gln | Asn | Ile | Val | Ser | Thr | Val | Asn | Leu |
|---|---|---|---|---|---|---|---|---|---|---|---|---|---|---|---|
| 1 | | | | 5 | | | | | 10 | | | | | 15 | |

| Asp | Cys | Lys | Leu | Asp | Leu | Lys | Ala | Ile | Ala | Leu | Gln | Ala | Arg | Asn | Ala |
|---|---|---|---|---|---|---|---|---|---|---|---|---|---|---|---|
| | | | 20 | | | | | 25 | | | | | 30 | | |

| Glu | Tyr | Asn | Pro | Lys | Arg | Phe | Ala | Ala | Val | Ile | Met | Arg | Ile | Arg | Glu |
|---|---|---|---|---|---|---|---|---|---|---|---|---|---|---|---|
| | | 35 | | | | | 40 | | | | | 45 | | | |

| Pro | Lys | Thr | Thr | Ala | Leu | Ile | Phe | Ala | Ser | Gly | Lys | Met | Val | Cys | Thr |
|---|---|---|---|---|---|---|---|---|---|---|---|---|---|---|---|
| | 50 | | | | | 55 | | | | | 60 | | | | |

| Gly | Ala | Lys | Ser | Glu | Asp | Phe | Ser | Lys | Met | Ala | Ala | Arg | Lys | Tyr | Ala |
|---|---|---|---|---|---|---|---|---|---|---|---|---|---|---|---|
| 65 | | | | | 70 | | | | | 75 | | | | | 80 |

| Arg | Ile | Val | Gln | Lys | Leu | Gly | Phe | Pro | Ala | Lys | Phe | Lys | Asp | Phe | Lys |
|---|---|---|---|---|---|---|---|---|---|---|---|---|---|---|---|
| | | | | 85 | | | | | 90 | | | | | 95 | |

| Ile | Gln | Asn | Ile | Val | Gly | Ser | Cys | Asp | Val | Lys | Phe | Pro | Ile | Arg | Leu |
|---|---|---|---|---|---|---|---|---|---|---|---|---|---|---|---|
| | | | 100 | | | | | 105 | | | | | 110 | | |

| Glu | Gly | Leu | Ala | Tyr | Ser | His | Ala | Ala | Phe | Ser | Ser | Tyr | Glu | Pro | Glu |
|---|---|---|---|---|---|---|---|---|---|---|---|---|---|---|---|
| | | | 115 | | | | | 120 | | | | | 125 | | |

| Leu | Phe | Pro | Gly | Leu | Ile | Tyr | Arg | Met | Lys | Val | Pro | Lys | Ile | Val | Leu |
|---|---|---|---|---|---|---|---|---|---|---|---|---|---|---|---|
| | | 130 | | | | | 135 | | | | | 140 | | | |

```
       Leu  Ile  Phe  Val  Ser  Gly  Lys  Ile  Val  Ile  Thr  Gly  Ala  Lys  Met  Arg
       145                 150                      155                           160

Asp  Glu  Thr  Tyr  Lys  Ala  Phe  Glu  Asn  Ile  Tyr  Pro  Val  Leu  Ser  Glu
                           165                      170                      175

Phe  Arg  Lys  Ile  Gln  Gln
                           180
```

( 2 ) INFORMATION FOR SEQ ID NO:94:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:94:

```
       Asn  Ser  Asn  Ser  Thr  Pro  Ile  Val  His  Leu  Lys  Gly  Asp  Ala  Asn  Thr
       1                   5                        10                            15

Leu  Lys  Cys  Leu  Arg  Tyr  Arg  Phe  Lys  Lys  His  Cys  Thr  Leu  Tyr  Thr
                      20                       25                       30

Ala  Val  Ser  Ser  Thr  Trp  His  Trp  Thr  Gly  His  Asn  Val  Lys  His  Lys
                      35                       40                       45

Ser  Ala  Ile  Val  Thr  Leu  Thr  Tyr  Asp  Ser  Glu  Trp  Gln  Arg  Asp  Gln
                 50                       55                       60

Phe  Leu  Ser  Gln  Val  Lys  Ile  Pro  Lys  Thr  Ile  Thr  Val  Ser  Thr  Gly
       65                       70                       75                            80

Phe  Met  Ser  Ile
```

( 2 ) INFORMATION FOR SEQ ID NO:95:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:95:

```
       Asn  Ser  Asn  Thr  Thr  Pro  Ile  Val  His  Leu  Lys  Gly  Asp  Ala  Asn  Thr
       1                   5                        10                            15

Leu  Lys  Cys  Leu  Arg  Tyr  Arg  Phe  Lys  Lys  His  Cys  Thr  Leu  Tyr  Thr
                      20                       25                       30

Ala  Val  Ser  Ser  Thr  Trp  His  Trp  Thr  Gly  His  Asn  Val  Lys  His  Lys
                      35                       40                       45

Ser  Ala  Ile  Val  Thr  Leu  Thr  Tyr  Asp  Ser  Glu  Trp  Gln  Arg  Asp  Gln
                 50                       55                       60

Phe  Leu  Ser  Gln  Val  Lys  Ile  Pro  Lys  Thr  Ile  Thr  Val  Ser  Thr  Gly
       65                       70                       75                            80

Phe  Met  Ser  Ile
```

( 2 ) INFORMATION FOR SEQ ID NO:96:

( i ) SEQUENCE CHARACTERISTICS:
        ( A ) LENGTH: 83 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:96:

```
Ser  Gly  Asn  Thr  Thr  Pro  Ile  Ile  His  Leu  Lys  Gly  Asp  Arg  Asn  Ser
1                   5                        10                       15

Leu  Lys  Cys  Leu  Arg  Tyr  Arg  Leu  Arg  Lys  His  Ser  Asp  His  Tyr  Arg
               20                      25                       30

Asp  Ile  Ser  Ser  Thr  Trp  His  Trp  Thr  Gly  Ala  Gly  Asn  Glu  Lys  Thr
               35                      40                       45

Gly  Ile  Leu  Thr  Val  Thr  Tyr  His  Ser  Glu  Thr  Gln  Arg  Thr  Lys  Phe
          50                      55                       60

Leu  Asn  Thr  Val  Ala  Ile  Pro  Asp  Ser  Val  Gln  Ile  Leu  Val  Gly  Tyr
65                       70                       75                       80

Met  Thr  Met
```

( 2 ) INFORMATION FOR SEQ ID NO:97:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:97:

```
Ser  Gly  Asn  Thr  Ala  Pro  Ile  Val  His  Leu  Lys  Gly  Glu  Ser  Asn  Ser
1                   5                        10                       15

Leu  Lys  Cys  Leu  Arg  Tyr  Arg  Leu  Lys  Pro  Tyr  Lys  Glu  Leu  Tyr  Ser
               20                      25                       30

Ser  Met  Ser  Ser  Thr  Trp  His  Trp  Thr  Ser  Asp  Asn  Lys  Asn  Ser  Lys
               35                      40                       45

Asn  Gly  Ile  Val  Thr  Val  Thr  Phe  Val  Thr  Glu  Gln  Gln  Gln  Gln  Met
          50                      55                       60

Phe  Leu  Gly  Thr  Val  Lys  Ile  Pro  Pro  Thr  Val  Gln  Ile  Ser  Thr  Gly
65                       70                       75                       80

Phe  Met  Thr  Leu
```

( 2 ) INFORMATION FOR SEQ ID NO:98:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:98:

Ser Gly Asn Thr Ser Cys Phe Ala Leu Ile Ser Gly Thr Ala Asn Gln
1               5                   10                  15

Val Lys Cys Tyr Arg Phe Arg Val Lys Lys Asn His Arg His Arg Tyr
            20                  25                  30

Glu Asn Cys Thr Thr Thr Trp Phe Thr Val Ala Asp Asn Gly Ala Glu
        35              40                  45

Arg Gln Gly Gln Ala Gln Ile Leu Ile Thr Phe Gly Ser Pro Ser Gln
        50              55                  60

Arg Gln Asp Phe Leu Lys His Val Pro Leu Pro Pro Gly Met Asn Ile
65                  70                  75                  80

Ser Gly Phe Thr Ala Ser Leu Asp Phe
                85

( 2 ) INFORMATION FOR SEQ ID NO:99:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:99:

Ser Asn Lys Lys Thr Thr Ala
1               5

( 2 ) INFORMATION FOR SEQ ID NO:100:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:100:

Asn Ser Asn Thr
1

( 2 ) INFORMATION FOR SEQ ID NO:101:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:101:

Ser Gly Asn Thr
1

( 2 ) INFORMATION FOR SEQ ID NO:102:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:102:

Ser Ser Gly Ser Ser Gly
1                   5

( 2 ) INFORMATION FOR SEQ ID NO:103:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:103:

Cys Tyr Pro Glu Ile Lys Asp Lys Glu Val Gln Arg Lys Arg
1               5                   10                  15

( 2 ) INFORMATION FOR SEQ ID NO:104:

( i ) SEQUENCE CHARACTERISTICS:
      ( A ) LENGTH: 66 amino acids
      ( B ) TYPE: amino acid
      ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:104:

Met Glu Gln Arg Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
                20                  25                  30

Ala Ile His Ala Gly Arg Lys Ile Phe Leu Thr Ile Asn Ala Asp Gly
            35                  40                  45

Ser Val Tyr Ala Glu Glu Val Lys Pro Phe Pro Ser Asn Lys Lys Thr
            50                  55                  60

Thr Ala
65

( 2 ) INFORMATION FOR SEQ ID NO:105:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:105:

Met Glu Gln Glu Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
        35                  40                  45

Ser Val Tyr Ala Glu Glu Val Lys Pro Phe Pro Ser Asn Lys Lys Thr
    50                  55                  60

Thr Ala
65

( 2 ) INFORMATION FOR SEQ ID NO:106:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:106:

Met Arg Gln Arg Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
        35                  40                  45

Ser Val Tyr Ala Glu Glu Val Lys Pro Phe Pro Ser Asn Lys Lys Thr
    50                  55                  60

Thr Ala
65

( 2 ) INFORMATION FOR SEQ ID NO:107:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:107:

| Ser | Thr | Lys | Lys | Lys | Pro | Leu | Thr | Gln | Glu | Gln | Leu | Glu | Asp | Ala | Arg |
|---|---|---|---|---|---|---|---|---|---|---|---|---|---|---|---|
| 1 | | | | 5 | | | | | 10 | | | | | 15 | |
| Arg | Leu | Lys | Ala | Ile | Tyr | Glu | Lys | Lys | Asn | Glu | Leu | Gly | Leu | Ser | |
| | | | 20 | | | | | 25 | | | | 30 | | | |
| Gln | Glu | Ser | Val | Ala | Asp | Lys | Met | Gly | Met | Gly | Gln | Ser | Gly | Val | Gly |
| | | 35 | | | | | 40 | | | | | 45 | | | |
| Ala | Leu | Phe | Asn | Gly | Ile | Asn | Ala | Leu | Asn | Ala | Tyr | Asn | Ala | Ala | Leu |
| | | 50 | | | | 55 | | | | | 60 | | | | |
| Leu | Ala | Lys | Ile | Leu | Lys | Val | Ser | Val | Glu | Glu | Phe | Ser | Pro | Ser | Ile |
| 65 | | | | | 70 | | | | | 75 | | | | | 80 |
| Ala | Arg | Glu | Ile | Tyr | Glu | Met | Tyr | Glu | Ala | Val | Ser | Met | Glu | Pro | Ser |
| | | | | 85 | | | | | 90 | | | | | 95 | |

( 2 ) INFORMATION FOR SEQ ID NO:108:

( i ) SEQUENCE CHARACTERISTICS:
( A ) LENGTH: 96 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:108:

| Ser | Thr | Lys | Lys | Lys | Pro | Leu | Thr | Gln | Glu | Gln | Leu | Glu | Asp | Ala | Arg |
|---|---|---|---|---|---|---|---|---|---|---|---|---|---|---|---|
| 1 | | | | 5 | | | | | 10 | | | | | 15 | |
| Arg | Leu | Lys | Ala | Ile | Tyr | Glu | Lys | Lys | Asn | Glu | Leu | Gly | Leu | Ser | |
| | | | 20 | | | | | 25 | | | | 30 | | | |
| Gln | Glu | Ser | Val | Ala | Asp | Lys | Met | Gly | Met | Gly | Gln | Ser | Gly | Val | Gly |
| | | 35 | | | | | 40 | | | | | 45 | | | |
| Ala | Leu | Phe | Asn | Gly | Ile | Asn | Ala | Leu | Asn | Ala | Tyr | Asn | Ala | Ala | Leu |
| | | 50 | | | | 55 | | | | | 60 | | | | |
| Leu | Ala | Lys | Ile | Leu | Lys | Val | Ser | Val | Glu | Glu | Phe | Ser | Pro | Ser | Ile |
| 65 | | | | | 70 | | | | | 75 | | | | | 80 |
| Ala | Arg | Glu | Ile | Tyr | Glu | Met | Cys | Glu | Ala | Val | Ser | Met | Glu | Pro | Ser |
| | | | | 85 | | | | | 90 | | | | | 95 | |

( 2 ) INFORMATION FOR SEQ ID NO:109:

( i ) SEQUENCE CHARACTERISTICS:
( A ) LENGTH: 180 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:109:

| Gly | Ile | Val | Glu | Gln | Cys | Cys | Thr | Ser | Ile | Cys | Ser | Leu | Tyr | Gln | Leu |
|---|---|---|---|---|---|---|---|---|---|---|---|---|---|---|---|

|   | 1 |   |   |   | 5 |   |   |   |   | 10 |   |   |   |   | 15 |
|---|---|---|---|---|---|---|---|---|---|---|---|---|---|---|---|
|   | Glu | Asn | Tyr | Cys | Asn | Met | Ser | Met | Glu | Gln | Arg | Ile | Thr | Leu | Lys | Asp |
|   |   |   |   | 20 |   |   |   |   | 25 |   |   |   |   | 30 |   |
|   | Tyr | Ala | Met | Arg | Phe | Gly | Gln | Thr | Lys | Thr | Ala | Lys | Asp | Leu | Gly | Val |
|   |   |   | 35 |   |   |   |   | 40 |   |   |   |   | 45 |   |   |
|   | Tyr | Gln | Ser | Ala | Ile | Asn | Lys | Ala | Ile | His | Ala | Gly | Arg | Lys | Ile | Phe |
|   |   | 50 |   |   |   |   | 55 |   |   |   |   | 60 |   |   |   |
|   | Leu | Thr | Ile | Asn | Ala | Asp | Gly | Ser | Val | Tyr | Ala | Glu | Glu | Val | Lys | Pro |
|   | 65 |   |   |   |   | 70 |   |   |   |   | 75 |   |   |   |   | 80 |
|   | Phe | Pro | Ser | Asn | Lys | Lys | Thr | Thr | Ala | Ser | Asn | Lys | Lys | Thr | Thr | Ala |
|   |   |   |   |   | 85 |   |   |   |   | 90 |   |   |   |   | 95 |   |
|   | Asn | Ser | Asn | Thr | Thr | Pro | Ile | Val | His | Leu | Lys | Gly | Asp | Ala | Asn | Thr |
|   |   |   |   | 100 |   |   |   |   | 105 |   |   |   |   | 110 |   |   |
|   | Leu | Lys | Cys | Leu | Arg | Tyr | Arg | Phe | Lys | Lys | His | Cys | Thr | Leu | Tyr | Thr |
|   |   |   | 115 |   |   |   |   | 120 |   |   |   |   | 125 |   |   |   |
|   | Ala | Val | Ser | Ser | Thr | Trp | His | Trp | Thr | Gly | His | Asn | Val | Lys | His | Lys |
|   |   | 130 |   |   |   |   | 135 |   |   |   |   | 140 |   |   |   |   |
|   | Ser | Ala | Ile | Val | Thr | Leu | Thr | Tyr | Asp | Ser | Glu | Trp | Gln | Arg | Asp | Gln |
|   | 145 |   |   |   |   | 150 |   |   |   |   | 155 |   |   |   |   | 160 |
|   | Phe | Leu | Ser | Gln | Val | Lys | Ile | Pro | Lys | Thr | Ile | Thr | Val | Ser | Thr | Gly |
|   |   |   |   |   | 165 |   |   |   |   | 170 |   |   |   |   | 175 |   |
|   | Phe | Met | Ser | Ile |   |   |   |   |   |   |   |   |   |   |   |   |
|   |   |   |   | 180 |   |   |   |   |   |   |   |   |   |   |   |   |

(2) INFORMATION FOR SEQ ID NO:110:

(i) SEQUENCE CHARACTERISTICS:
        (A) LENGTH: 113 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:110:

|   | Gly | Ile | Val | Glu | Gln | Cys | Cys | Thr | Ser | Ile | Cys | Ser | Leu | Tyr | Gln | Leu |
|---|---|---|---|---|---|---|---|---|---|---|---|---|---|---|---|---|
|   | 1 |   |   |   | 5 |   |   |   |   | 10 |   |   |   |   | 15 |   |
|   | Glu | Asn | Tyr | Cys | Asn | Met | Ser | Met | Glu | Gln | Arg | Ile | Thr | Leu | Lys | Asp |
|   |   |   |   | 20 |   |   |   |   | 25 |   |   |   |   | 30 |   |   |
|   | Tyr | Ala | Met | Arg | Phe | Gly | Gln | Thr | Lys | Thr | Ala | Lys | Asp | Leu | Gly | Val |
|   |   |   | 35 |   |   |   |   | 40 |   |   |   |   | 45 |   |   |   |
|   | Tyr | Gln | Ser | Ala | Ile | Asn | Lys | Ala | Ile | His | Ala | Gly | Arg | Lys | Ile | Phe |
|   |   | 50 |   |   |   |   | 55 |   |   |   |   | 60 |   |   |   |   |
|   | Leu | Thr | Ile | Asn | Ala | Asp | Gly | Ser | Val | Tyr | Ala | Glu | Glu | Val | Lys | Pro |
|   | 65 |   |   |   |   | 70 |   |   |   |   | 75 |   |   |   |   | 80 |
|   | Phe | Pro | Ser | Asn | Lys | Lys | Thr | Thr | Ala | Ser | Asn | Lys | Lys | Thr | Thr | Ala |
|   |   |   |   |   | 85 |   |   |   |   | 90 |   |   |   |   | 95 |   |
|   | Cys | Asp | Thr | Asp | Asp | Arg | His | Arg | Ile | Glu | Glu | Lys | Arg | Lys | Arg | Lys |
|   |   |   |   | 100 |   |   |   |   | 105 |   |   |   |   | 110 |   |   |
|   | Thr |   |   |   |   |   |   |   |   |   |   |   |   |   |   |   |

(2) INFORMATION FOR SEQ ID NO:111:

(i) SEQUENCE CHARACTERISTICS:

(A) LENGTH: 292 amino acids
(B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:111:

| Phe | Val | Asn | Gln | His | Leu | Cys | Gly | Ser | His | Leu | Val | Glu | Ala | Leu | Tyr |
|---|---|---|---|---|---|---|---|---|---|---|---|---|---|---|---|
| 1 | | | | 5 | | | | | 10 | | | | | 15 | |
| Leu | Val | Cys | Gly | Glu | Arg | Gly | Phe | Phe | Tyr | Thr | Pro | Lys | Thr | Met | Ser |
| | | | 20 | | | | | 25 | | | | | 30 | | |
| Met | Glu | Gln | Glu | Ile | Thr | Leu | Lys | Asp | Tyr | Ala | Met | Arg | Phe | Gly | Gln |
| | | | 35 | | | | 40 | | | | | 45 | | | |
| Thr | Lys | Thr | Ala | Lys | Asp | Leu | Gly | Val | Tyr | Gln | Ser | Ala | Ile | Asn | Lys |
| | 50 | | | | | 55 | | | | | 60 | | | | |
| Ala | Ile | His | Ala | Gly | Arg | Lys | Ile | Phe | Leu | Thr | Ile | Asn | Ala | Asp | Gly |
| 65 | | | | | 70 | | | | | 75 | | | | | 80 |
| Ser | Val | Tyr | Ala | Glu | Glu | Val | Lys | Pro | Phe | Pro | Ser | Asn | Lys | Lys | Thr |
| | | | | 85 | | | | | 90 | | | | | 95 | |
| Thr | Ala | Ser | Asn | Lys | Lys | Thr | Thr | Ala | Ser | Ser | Gly | Ser | Ser | Gly | Ser |
| | | | 100 | | | | | 105 | | | | | 110 | | |
| Gly | Ile | Val | Pro | Gln | Leu | Gln | Asn | Ile | Val | Ser | Thr | Val | Asn | Leu | Gly |
| | | | 115 | | | | 120 | | | | | 125 | | | |
| Cys | Lys | Leu | Asp | Leu | Lys | Thr | Ile | Ala | Leu | Arg | Ala | Arg | Asn | Ala | Glu |
| | 130 | | | | | 135 | | | | | 140 | | | | |
| Tyr | Asn | Pro | Lys | Arg | Phe | Ala | Ala | Val | Ile | Met | Arg | Ile | Arg | Glu | Pro |
| 145 | | | | | 150 | | | | | 155 | | | | | 160 |
| Arg | Thr | Thr | Ala | Leu | Ile | Phe | Ser | Ser | Gly | Lys | Met | Val | Cys | Thr | Gly |
| | | | | 165 | | | | | 170 | | | | | 175 | |
| Ala | Lys | Ser | Glu | Glu | Gln | Ser | Arg | Leu | Ala | Ala | Arg | Lys | Tyr | Ala | Arg |
| | | | | 180 | | | | | 185 | | | | | 190 | |
| Val | Val | Gln | Lys | Leu | Gly | Phe | Pro | Ala | Lys | Phe | Leu | Asp | Phe | Lys | Ile |
| | | | 195 | | | | | 200 | | | | | 205 | | |
| Gln | Asn | Met | Val | Gly | Ser | Cys | Asp | Val | Lys | Phe | Pro | Ile | Arg | Leu | Glu |
| | | 210 | | | | | 215 | | | | | 220 | | | |
| Gly | Leu | Val | Leu | Thr | His | Gln | Gln | Phe | Ser | Ser | Tyr | Glu | Pro | Glu | Leu |
| 225 | | | | | 230 | | | | | 235 | | | | | 240 |
| Phe | Pro | Gly | Leu | Ile | Tyr | Arg | Met | Ile | Lys | Pro | Arg | Ile | Val | Leu | Leu |
| | | | | 245 | | | | | 250 | | | | | 255 | |
| Ile | Phe | Val | Ser | Gly | Lys | Val | Val | Leu | Thr | Gly | Ala | Lys | Val | Arg | Ala |
| | | | 260 | | | | | 265 | | | | | 270 | | |
| Glu | Ile | Tyr | Glu | Ala | Phe | Glu | Asn | Ile | Tyr | Pro | Ile | Leu | Lys | Gly | Phe |
| | | 275 | | | | | 280 | | | | | 285 | | | |
| Arg | Lys | Thr | Thr | | | | | | | | | | | | |
| | 290 | | | | | | | | | | | | | | |

(2) INFORMATION FOR SEQ ID NO:112:

(i) SEQUENCE CHARACTERISTICS:
(A) LENGTH: 273 amino acids
(B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:112:

| Phe | Val | Asn | Gln | His | Leu | Cys | Gly | Ser | His | Leu | Val | Glu | Ala | Leu | Tyr |
|---|---|---|---|---|---|---|---|---|---|---|---|---|---|---|---|
| 1 | | | | 5 | | | | | 10 | | | | | 15 | |
| Leu | Val | Cys | Gly | Glu | Arg | Gly | Phe | Phe | Tyr | Thr | Pro | Lys | Thr | Met | Ser |
| | | | 20 | | | | | 25 | | | | | 30 | | |
| Met | Arg | Gln | Arg | Ile | Thr | Leu | Lys | Asp | Tyr | Ala | Met | Arg | Phe | Gly | Gln |
| | | | 35 | | | | 40 | | | | | 45 | | | |
| Thr | Lys | Thr | Ala | Lys | Asp | Leu | Gly | Val | Tyr | Gln | Ser | Ala | Ile | Asn | Lys |
| | 50 | | | | | 55 | | | | | 60 | | | | |
| Ala | Ile | His | Ala | Gly | Arg | Lys | Ile | Phe | Leu | Thr | Ile | Asn | Ala | Asp | Gly |
| 65 | | | | | 70 | | | | | 75 | | | | | 80 |
| Ser | Val | Tyr | Ala | Glu | Glu | Val | Lys | Pro | Phe | Pro | Ser | Asn | Lys | Lys | Thr |
| | | | | 85 | | | | | 90 | | | | | 95 | |
| Thr | Ala | Ser | Asn | Lys | Lys | Thr | Thr | Ala | Gly | Asp | Pro | Gly | Lys | Lys | Lys |
| | | | | 100 | | | | 105 | | | | | 110 | | |
| Gln | His | Ile | Cys | His | Ile | Gln | Gly | Cys | Gly | Lys | Val | Tyr | Gly | Lys | Thr |
| | | 115 | | | | | 120 | | | | | 125 | | | |
| Ser | His | Leu | Arg | Ala | His | Leu | Arg | Trp | His | Thr | Gly | Glu | Arg | Pro | Phe |
| | 130 | | | | | 135 | | | | | 140 | | | | |
| Met | Cys | Thr | Trp | Ser | Tyr | Cys | Gly | Lys | Arg | Phe | Thr | Arg | Ser | Asp | Glu |
| 145 | | | | | 150 | | | | | 155 | | | | | 160 |
| Leu | Gln | Arg | His | Lys | Arg | Thr | His | Thr | Gly | Glu | Lys | Lys | Phe | Ala | Cys |
| | | | | 165 | | | | | 170 | | | | | 175 | |
| Pro | Glu | Cys | Pro | Lys | Arg | Phe | Met | Arg | Ser | Asp | His | Leu | Ser | Lys | His |
| | | | 180 | | | | | 185 | | | | | 190 | | |
| Ile | Lys | Thr | His | Gln | Asn | Lys | Lys | Gly | Gly | Pro | Gly | Val | Ala | Leu | Ser |
| | | 195 | | | | | 200 | | | | | 205 | | | |
| Val | Gly | Thr | Leu | Pro | Leu | Asp | Ser | Gly | Ala | Gly | Ser | Glu | Gly | Ser | Gly |
| | 210 | | | | | 215 | | | | | 220 | | | | |
| Thr | Ala | Thr | Pro | Ser | Ala | Leu | Ile | Thr | Thr | Asn | Met | Val | Ala | Met | Glu |
| 225 | | | | | 230 | | | | | 235 | | | | | 240 |
| Ala | Ile | Cys | Pro | Glu | Gly | Ile | Ala | Arg | Leu | Ala | Asn | Ser | Gly | Ile | Asn |
| | | | | 245 | | | | | 250 | | | | | 255 | |
| Val | Met | Gln | Val | Ala | Asp | Leu | Gln | Ser | Ile | Asn | Ile | Ser | Gly | Asn | Gly |
| | | | 260 | | | | | 265 | | | | | 270 | | |
| Phe | | | | | | | | | | | | | | | |

(2) INFORMATION FOR SEQ ID NO:113:

(i) SEQUENCE CHARACTERISTICS:
(A) LENGTH: 421 amino acids
(B) TYPE: amino acid
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:113:

-continued

```
Gln Leu Tyr Ser Ala Leu Ala Asn Lys Cys Cys His Val Gly Cys Ile
1               5                   10                  15

Lys Arg Ser Leu Ala Arg Phe Cys Met Ser Met Arg Gln Arg Ile Thr
            20              25              30

Leu Lys Asp Tyr Ala Met Arg Phe Gly Gln Thr Lys Thr Ala Lys Asp
            35              40              45

Leu Gly Val Tyr Gln Ser Ala Ile Asn Lys Ala Ile His Ala Gly Arg
            50              55              60

Lys Ile Phe Leu Thr Ile Asn Ala Asp Gly Ser Val Tyr Ala Glu Glu
65              70              75                          80

Val Lys Pro Phe Pro Ser Asn Lys Lys Thr Ala Ser Asn Lys Lys
                85              90              95

Thr Thr Ala Met Ala Asp Asp Pro Tyr Gly Thr Gly Gln Met Phe
            100             105             110

His Leu Asn Thr Ala Leu Thr His Ser Ile Phe Asn Ala Glu Leu Tyr
            115             120             125

Ser Pro Glu Ile Pro Leu Ser Thr Asp Gly Pro Tyr Leu Gln Ile Leu
    130             135             140

Glu Gln Pro Lys Gln Arg Gly Phe Arg Phe Arg Tyr Val Cys Glu Gly
145                 150             155                     160

Pro Ser His Gly Gly Leu Pro Gly Ala Ser Ser Glu Lys Asn Lys Lys
                165             170             175

Ser Tyr Pro Gln Val Lys Ile Cys Asn Tyr Val Gly Pro Ala Lys Val
            180             185             190

Ile Val Gln Leu Val Thr Asn Gly Lys Asn Ile His Leu His Ala His
        195             200             205

Ser Leu Val Gly Lys His Cys Glu Asp Gly Val Cys Thr Val Thr Ala
    210             215             220

Gly Pro Lys Asp Met Val Val Gly Phe Ala Asn Leu Gly Ile Leu His
225             230             235                         240

Val Thr Lys Lys Lys Val Phe Glu Thr Leu Glu Ala Arg Met Thr Glu
                245             250             255

Ala Cys Ile Arg Gly Tyr Asn Pro Gly Leu Leu Val His Ser Asp Leu
            260             265             270

Ala Tyr Leu Gln Ala Glu Gly Gly Asp Arg Gln Leu Thr Asp Arg
            275             280             285

Glu Lys Glu Ile Ile Arg Gln Ala Ala Val Gln Gln Thr Lys Glu Met
    290             295             300

Asp Leu Ser Val Val Arg Leu Met Phe Thr Ala Phe Leu Pro Asp Ser
305             310             315                         320

Thr Gly Ser Phe Thr Arg Arg Leu Glu Pro Val Val Ser Asp Ala Ile
            325             330             335

Tyr Asp Ser Lys Ala Pro Asn Ala Ser Asn Leu Lys Ile Val Arg Met
            340             345             350

Asp Arg Thr Ala Gly Cys Val Thr Gly Gly Glu Glu Ile Tyr Leu Leu
        355             360             365

Cys Asp Lys Val Gln Lys Asp Asp Ile Gln Ile Arg Phe Tyr Glu Glu
    370             375             380

Glu Glu Asn Gly Gly Val Trp Glu Gly Phe Gly Asp Phe Ser Pro Thr
385             390             395                         400

Asp Val His Arg Gln Phe Ala Ile Val Phe Lys Thr Pro Lys Tyr Lys
            405             410             415

Asp Val Asn Ile Thr
            420
```

(2) INFORMATION FOR SEQ ID NO:114:

(i) SEQUENCE CHARACTERISTICS:
        (A) LENGTH: 391 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:114:

```
Met Arg Gln Arg Ile Thr Leu Lys Asp Tyr Ala Met Arg Phe Gly Gln
1               5                   10                  15

Thr Lys Thr Ala Lys Asp Leu Gly Val Tyr Gln Ser Ala Ile Asn Lys
            20                  25                  30

Ala Ile His Ala Gly Arg Lys Ile Phe Leu Thr Ile Asn Ala Asp Gly
        35                  40                  45

Ser Val Tyr Ala Glu Glu Val Lys Pro Phe Pro Ser Asn Lys Lys Thr
    50                  55                  60

Thr Ala Met Ala Glu Asp Asp Pro Tyr Leu Gly Arg Pro Glu Gln Met
65                  70                  75                  80

Phe His Leu Asp Pro Ser Leu Thr His Thr Ile Phe Asn Pro Glu Val
                85                  90                  95

Phe Gln Pro Gln Met Ala Leu Pro Thr Ala Asp Gly Pro Tyr Leu Gln
            100                 105                 110

Ile Leu Glu Gln Pro Lys Gln Arg Gly Phe Arg Phe Arg Tyr Val Cys
            115                 120                 125

Glu Gly Pro Ser His Gly Gly Leu Pro Gly Ala Ser Ser Glu Lys Asn
        130                 135                 140

Lys Lys Ser Tyr Pro Gln Val Lys Ile Cys Asn Tyr Val Gly Pro Ala
145                 150                 155                 160

Lys Val Ile Val Gln Leu Val Thr Asn Gly Lys Asn Ile His Leu His
                165                 170                 175

Ala His Ser Leu Val Gly Lys His Cys Glu Asp Gly Ile Cys Thr Val
            180                 185                 190

Thr Ala Gly Pro Glu Asp Cys Val His Gly Phe Ala Asn Leu Gly Ile
        195                 200                 205

Leu His Val Thr Lys Lys Lys Val Phe Glu Thr Leu Glu Ala Arg Met
    210                 215                 220

Thr Glu Ala Cys Ile Arg Gly Tyr Asn Pro Gly Leu Leu Val His Pro
225                 230                 235                 240

Asp Leu Ala Tyr Leu Gln Ala Glu Gly Gly Gly Asp Arg Gln Leu Gly
                245                 250                 255

Asp Arg Glu Lys Glu Leu Ile Arg Gln Ala Ala Leu Gln Gln Thr Lys
            260                 265                 270

Glu Met Asp Leu Ser Val Val Arg Leu Met Phe Thr Ala Phe Leu Pro
        275                 280                 285

Asp Ser Thr Gly Ser Phe Thr Arg Arg Leu Glu Pro Val Val Ser Asp
    290                 295                 300

Ala Ile Tyr Asp Ser Lys Ala Pro Asn Ala Ser Asn Leu Lys Ile Val
305                 310                 315                 320

Arg Met Asp Arg Thr Ala Gly Cys Val Thr Gly Gly Glu Glu Ile Tyr
```

-continued

|     |     |     |     | 325 |     |     |     | 330 |     |     |     | 335 |     |     |
| --- | --- | --- | --- | --- | --- | --- | --- | --- | --- | --- | --- | --- | --- | --- |
| Leu | Leu | Cys | Asp | Lys | Val | Gln | Lys | Asp | Ile | Gln | Ile | Arg | Phe | Tyr |
|     |     |     | 340 |     |     |     | 345 |     |     |     | 350 |     |     |     |
| Glu | Glu | Glu | Glu | Asn | Gly | Gly | Val | Trp | Glu | Gly | Phe | Gly | Asp | Phe | Ser |
|     |     | 355 |     |     |     | 360 |     |     |     | 365 |     |     |     |     |
| Pro | Thr | Asp | Val | His | Arg | Gln | Phe | Ala | Ile | Val | Phe | Lys | Thr | Pro | Lys |
|     | 370 |     |     |     |     | 375 |     |     |     | 380 |     |     |     |     |
| Tyr | Lys | Asp | Ile | Asn | Ile | Thr |
| 385 |     |     |     |     | 390 |     |

(2) INFORMATION FOR SEQ ID NO:115:

(i) SEQUENCE CHARACTERISTICS:
        (A) LENGTH: 391 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:115:

| Met | Glu | Gln | Glu | Ile | Thr | Leu | Lys | Asp | Tyr | Ala | Met | Arg | Phe | Gly | Gln |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Thr | Lys | Thr | Ala | Lys | Asp | Leu | Gly | Val | Tyr | Gln | Ser | Ala | Ile | Asn | Lys |
|     |     |     | 20  |     |     |     |     | 25  |     |     |     |     | 30  |     |     |
| Ala | Ile | His | Ala | Gly | Arg | Lys | Ile | Phe | Leu | Thr | Ile | Asn | Ala | Asp | Gly |
|     |     |     | 35  |     |     |     |     | 40  |     |     |     |     | 45  |     |     |
| Ser | Val | Tyr | Ala | Glu | Glu | Val | Lys | Pro | Phe | Pro | Ser | Asn | Lys | Lys | Thr |
|     | 50  |     |     |     |     | 55  |     |     |     |     | 60  |     |     |     |     |
| Thr | Ala | Met | Ala | Glu | Asp | Pro | Tyr | Leu | Gly | Arg | Pro | Glu | Gln | Met |
| 65  |     |     |     |     | 70  |     |     |     |     | 75  |     |     |     | 80  |
| Phe | His | Leu | Asp | Pro | Ser | Leu | Thr | His | Thr | Ile | Phe | Asn | Pro | Glu | Val |
|     |     |     |     | 85  |     |     |     |     | 90  |     |     |     |     | 95  |     |
| Phe | Gln | Pro | Gln | Met | Ala | Leu | Pro | Thr | Ala | Asp | Gly | Pro | Tyr | Leu | Gln |
|     |     |     |     | 100 |     |     |     |     | 105 |     |     |     |     | 110 |     |
| Ile | Leu | Glu | Gln | Pro | Lys | Gln | Arg | Gly | Phe | Arg | Phe | Arg | Tyr | Val | Cys |
|     |     |     | 115 |     |     |     |     | 120 |     |     |     |     | 125 |     |     |
| Glu | Gly | Pro | Ser | His | Gly | Gly | Leu | Pro | Gly | Ala | Ser | Ser | Glu | Lys | Asn |
|     |     | 130 |     |     |     |     | 135 |     |     |     |     | 140 |     |     |     |
| Lys | Lys | Ser | Tyr | Pro | Gln | Val | Lys | Ile | Cys | Asn | Tyr | Val | Gly | Pro | Ala |
| 145 |     |     |     |     | 150 |     |     |     |     | 155 |     |     |     |     | 160 |
| Lys | Val | Ile | Val | Gln | Leu | Val | Thr | Asn | Gly | Lys | Asn | Ile | His | Leu | His |
|     |     |     |     | 165 |     |     |     |     | 170 |     |     |     |     | 175 |     |
| Ala | His | Ser | Leu | Val | Gly | Lys | His | Cys | Glu | Asp | Gly | Ile | Cys | Thr | Val |
|     |     |     |     | 180 |     |     |     |     | 185 |     |     |     |     | 190 |     |
| Thr | Ala | Gly | Pro | Glu | Asp | Cys | Val | His | Gly | Phe | Ala | Asn | Leu | Gly | Ile |
|     |     |     | 195 |     |     |     |     | 200 |     |     |     |     | 205 |     |     |
| Leu | His | Val | Thr | Lys | Lys | Lys | Val | Phe | Glu | Thr | Leu | Glu | Ala | Arg | Met |
|     |     | 210 |     |     |     |     | 215 |     |     |     |     | 220 |     |     |     |
| Thr | Glu | Ala | Cys | Ile | Arg | Gly | Tyr | Asn | Pro | Gly | Leu | Leu | Val | His | Pro |
| 225 |     |     |     |     | 230 |     |     |     |     | 235 |     |     |     |     | 240 |
| Asp | Leu | Ala | Tyr | Leu | Gln | Ala | Glu | Gly | Gly | Gly | Asp | Arg | Gln | Leu | Gly |
|     |     |     |     | 245 |     |     |     |     | 250 |     |     |     |     | 255 |     |

|     |     |     |     |     |     |     |     |     |     |     |     |     |     |     |
|---|---|---|---|---|---|---|---|---|---|---|---|---|---|---|
| Asp | Arg | Glu | Lys<br>260 | Glu | Leu | Ile | Arg | Gln<br>265 | Ala | Ala | Leu | Gln | Gln<br>270 | Thr | Lys |
| Glu<br>275 | Met | Asp | Leu | Ser | Val | Val | Arg<br>280 | Leu | Met | Phe | Thr | Ala<br>285 | Phe | Leu | Pro |
| Asp | Ser<br>290 | Thr | Gly | Ser | Phe | Thr<br>295 | Arg | Arg | Leu | Glu | Pro<br>300 | Val | Val | Ser | Asp |
| Ala<br>305 | Ile | Tyr | Asp | Ser | Lys<br>310 | Ala | Pro | Asn | Ala | Ser<br>315 | Asn | Leu | Lys | Ile | Val<br>320 |
| Arg | Met | Asp | Arg | Thr<br>325 | Ala | Gly | Cys | Val | Thr<br>330 | Gly | Gly | Glu | Glu | Ile<br>335 | Tyr |
| Leu | Leu | Cys | Asp<br>340 | Lys | Val | Gln | Lys | Asp<br>345 | Asp | Ile | Gln | Ile | Arg<br>350 | Phe | Tyr |
| Glu | Glu | Glu<br>355 | Glu | Asn | Gly | Gly | Val<br>360 | Trp | Glu | Gly | Phe | Gly<br>365 | Asp | Phe | Ser |
| Pro | Thr<br>370 | Asp | Val | His | Arg | Gln<br>375 | Phe | Ala | Ile | Val | Phe<br>380 | Lys | Thr | Pro | Lys |
| Tyr<br>385 | Lys | Asp | Ile | Asn<br>390 | Thr |

( 2 ) INFORMATION FOR SEQ ID NO:116:

( i ) SEQUENCE CHARACTERISTICS:
( A ) LENGTH: 241 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:116:

|     |     |     |     |     |     |     |     |     |     |     |     |     |     |     |
|---|---|---|---|---|---|---|---|---|---|---|---|---|---|---|
| Met<br>1 | Arg | Gln | Arg | Ile<br>5 | Thr | Leu | Lys | Asp | Tyr<br>10 | Ala | Met | Arg | Phe | Gly<br>15 | Gln |
| Thr | Lys | Thr | Ala<br>20 | Lys | Asp | Leu | Gly | Val<br>25 | Tyr | Gln | Ser | Ala | Ile<br>30 | Asn | Lys |
| Ala | Ile | His<br>35 | Ala | Gly | Arg | Lys | Ile<br>40 | Phe | Leu | Thr | Ile | Asn<br>45 | Ala | Asp | Gly |
| Ser | Val<br>50 | Tyr | Ala | Glu | Glu | Val<br>55 | Lys | Pro | Phe | Pro | Ser<br>60 | Asn | Lys | Lys | Thr |
| Thr<br>65 | Ala | Ser | Asn | Lys | Lys<br>70 | Thr | Thr | Ala | Gly | Asp<br>75 | Pro | Gly | Lys | Lys | Lys<br>80 |
| Gln | His | Ile | Cys | His<br>85 | Ile | Gln | Gly | Cys | Gly<br>90 | Lys | Val | Tyr | Gly | Lys<br>95 | Thr |
| Ser | His | Leu | Arg<br>100 | Ala | His | Leu | Arg | Trp<br>105 | His | Thr | Gly | Glu | Arg<br>110 | Pro | Phe |
| Met | Cys | Thr<br>115 | Trp | Ser | Tyr | Cys | Gly<br>120 | Lys | Arg | Phe | Thr | Arg<br>125 | Ser | Asp | Glu |
| Leu | Gln<br>130 | Arg | His | Lys | Arg | Thr<br>135 | His | Thr | Gly | Glu | Lys<br>140 | Lys | Phe | Ala | Cys |
| Pro<br>145 | Glu | Cys | Pro | Lys | Arg<br>150 | Phe | Met | Arg | Ser | Asp<br>155 | His | Leu | Ser | Lys | His<br>160 |
| Ile | Lys | Thr | His | Gln<br>165 | Asn | Lys | Lys | Gly | Gly<br>170 | Pro | Gly | Val | Ala | Leu<br>175 | Ser |
| Val | Gly | Thr | Leu<br>180 | Pro | Leu | Asp | Ser | Gly<br>185 | Ala | Gly | Ser | Glu | Gly<br>190 | Ser | Gly |

-continued

```
Thr Ala Thr Pro Ser Ala Leu Ile Thr Thr Asn Met Val Ala Met Glu
    195                 200                 205
Ala Ile Cys Pro Glu Gly Ile Ala Arg Leu Ala Asn Ser Gly Ile Asn
    210             215                 220
Val Met Gln Val Ala Asp Leu Gln Ser Ile Asn Ile Ser Gly Asn Gly
225                 230                 235                 240
Phe
```

( 2 ) INFORMATION FOR SEQ ID NO:117:

( i ) SEQUENCE CHARACTERISTICS:
      ( A ) LENGTH: 10 base pairs
      ( B ) TYPE: nucleic acid
      ( C ) STRANDEDNESS: both
      ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:117:

GGGAMTNYCC                                                                 10